US008569300B2

(12) United States Patent
Borchardt et al.

(10) Patent No.: US 8,569,300 B2
(45) Date of Patent: Oct. 29, 2013

(54) SUBSTITUTED TETRAZOLO[1,5-A]PYRAZINE INHIBITORS OF HISTAMINE RECEPTORS FOR THE TREATMENT OF DISEASE

(75) Inventors: Allen Borchardt, San Diego, CA (US); Robert Davis, Carlsbad, CA (US); Stewart A. Noble, San Diego, CA (US)

(73) Assignee: Kalypsys Inc., La Jolla, CA (US)

( * ) Notice: Subject to any disclaimer, the term of this patent is extended or adjusted under 35 U.S.C. 154(b) by 159 days.

(21) Appl. No.: 13/044,661

(22) Filed: Mar. 10, 2011

(65) Prior Publication Data

US 2011/0237565 A1 Sep. 29, 2011

Related U.S. Application Data

(60) Provisional application No. 61/312,615, filed on Mar. 10, 2010.

(51) Int. Cl.
*A61K 31/495* (2006.01)

(52) U.S. Cl.
USPC ........... 514/249; 544/350; 544/359; 548/557; 548/953; 549/59

(58) Field of Classification Search
USPC ........... 514/249; 544/350, 359; 548/557, 953; 549/59
See application file for complete search history.

(56) References Cited

U.S. PATENT DOCUMENTS

| 2008/0139572 A1 | 6/2008 | Wang et al. |
| 2010/0120741 A1 | 5/2010 | Borchardt et al. |
| 2011/0237599 A1 | 9/2011 | Borchardt et al. |

FOREIGN PATENT DOCUMENTS

| WO | 2004022060 A2 | 3/2004 |
| WO | 2008031556 A2 | 3/2008 |
| WO | 2009089547 A1 | 7/2009 |
| WO | 2009098320 A2 | 8/2009 |
| WO | 2010030785 A2 | 3/2010 |
| WO | 2011112687 A1 | 3/2011 |
| WO | 2011075591 A1 | 6/2011 |
| WO | 2011089400 A1 | 7/2011 |

OTHER PUBLICATIONS

Conalty, ML et al., Anticancer agents—XII. Pyridazine and Benzodiazine derivatives, Proceedings of the Royal Irish Academy, Section B: Biological, Geological and Chemical Science (1976), 76(10), 151-63.
Kim, Ho Sik et al., Synthesis of tetrazolo[1,5-a]quinoxalines with antimicrobial activity, Journal of the Korean Chemical Society (2001), 45(4), 325-333 CODEN: JKCSEZ; ISSN: 1017-2548.
International Search Report of International Publication No. WO 2010/030785 A2 entitled "Heterocyclic Inhibitors of Histamine Receptors for the Treatment of Disease", Borchardt, A.J. et al., Date May 10, 2010.
Written Opinion of the International Searching Authority of International Publication No. WO2010030785 A2 entitled "Heterocyclic Inhibitors of Histamine Receptors for the Treatment of Disease", Borchardt, A.J. et al., Date May 10, 2010.
International Preliminary Report on Patentability of International Publication No. WO2010030785 A2 entitled "Heterocyclic Inhibitors of Histamine Receptors for the Treatment of Disease", Borchardt, A.J. et al., Date Mar. 24, 2011.
European Search Report of EPO Publication No. EP 2324029 entitled "Heterocyclic Inhibitors of Histamine Receptors for the Treatment of Disease", Borchardt, A.J. et al., Date Aug. 17, 2011.
Response of Smaggasgale, G.H., Patent Agent, Dated Feb. 29, 2012 to International Search Report of International Publication No. EP 2324029 entitled "Heterocyclic Inhibitors of Histamine Receptors for the Treatment of Disease", Borchardt, A.J. et al., Date Feb. 29, 2012.
International Search Report and Written Opinion of the ISA of International publication No. WO2011112766A2 entitled "Heterocyclic Inhibitors of Histamine Receptors for the Treatment of Disease", Borchardt, A.J. et al., Date Sep. 15, 2011.
Smits R. A. et al., Major advances in the developments of histamine H4 receptor legands, Drug Discovery Today, vol. 14, No. 15/16, Aug. 2009.

*Primary Examiner* — Douglas M Willis
(74) *Attorney, Agent, or Firm* — Dennis A. Bennett; Cynthia Hathaway

(57) ABSTRACT

The present invention relates to substituted tetrazolo[1,5-a]pyrazine compounds for Formula IX:

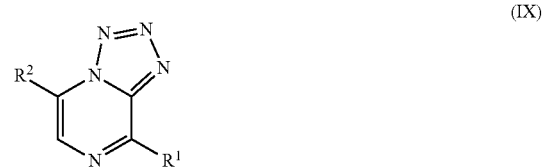

as well as pharmaceutical compositions thereof, which may be useful as inhibitors of H4R for the treatment or prevention of inflammatory, autoimmune, allergic, and ocular diseases.

17 Claims, No Drawings

SUBSTITUTED TETRAZOLO[1,5-A]PYRAZINE INHIBITORS OF HISTAMINE RECEPTORS FOR THE TREATMENT OF DISEASE

CROSS REFERENCE TO RELATED APPLICATIONS

This application claims the benefit of U.S. Provisional Applications No. 61/312,615, filed Mar. 10, 2010 the disclosure of which is hereby incorporated by reference as if written herein in its entirety.

Disclosed herein are new heterocyclic compounds and compositions and their application as pharmaceuticals for the treatment of disease. Methods of inhibition of histamine receptor activity in a human or animal subject are also provided for the treatment of allergic diseases, inflammation, asthma, rhinitis, chronic obstructive pulmonary disease, conjunctivitis, rheumatoid arthritis, and general and localized pruritis.

Histamine, a low molecular weight biogenic amine, is a potent chemical mediator of normal and pathological physiology. Histamine functions as a secreted signal in immune and inflammatory responses, as well as a neurotransmitter. The functions of histamine are mediated through 4 distinct cell surface receptors ($H_1R$, $H_2R$, $H_3R$ and $H_4R$). Histamine receptors vary in expression, signaling, function and histamine affinity, and therefore have different potential therapeutic applications (Zhang M, Thurmond R L, and Dunford P J *Pharmacology & Therapeutics*. 2007).

All 4 histamine receptors are G protein-coupled receptors (GPCRs). Upon histamine or other agonist binding, they activate distinct signaling pathways through different heterotrimeric G proteins. The $H_1R$ couples to the $G_q$ family of G proteins, whose primary signaling cascade induces second messenger calcium mobilization from intracellular stores, followed by multiple downstream effects. $H_1R$ can also increase cyclic GMP (cGMP) production and activate NFκB, a potent, positive transcriptional regulator of inflammation. The $H_2R$ couples to the $G_s$ family of G proteins and increases cyclic AMP (cAMP) formation by stimulating adenylate cyclase, although it can also induce calcium mobilization in some cell types. The $H_3R$ mediates its function through $G_{i/o}$ proteins and decreases cAMP formation by inhibiting adenylate cyclase. Like other $G_{i/o}$-coupled receptors, $H_3R$ also activates the mitogen-activated protein/extracellular-signal regulated protein (MAP/ERK) kinase pathway. $H_4R$ has also been demonstrated to couple to $G_{i/o}$ proteins, with canonical inhibition of cAMP formation and MAP kinase activation. However, $H_4R$ also couples to calcium mobilization in certain cell types. In fact, $H_4R$ signaling in mast cells is primarily through calcium mobilization with little to no impact on cAMP formation.

The $H_1R$ is expressed in many cell types, including endothelial cells, most smooth muscle cells, cardiac muscle, central nervous system (CNS) neurons, and lymphocytes. $H_1R$ signaling causes smooth muscle contraction (including bronchoconstriction), vasodilation, and increased vascular permeability, hallmarks of allergic and other immediate hypersensitivity reactions. In the CNS, $H_1R$ activation is associated with wakefulness. Its activation is also associated with pruritus and nociception in skin and mucosal tissues. For many years, the anti-allergic and anti-inflammatory activities of $H_1R$ antagonists have been utilized to treat acute and chronic allergic disorders and other histamine-mediated pathologies, such as itch and hives.

The $H_2R$ is expressed similarly to the $H_1R$, and can also be found in gastric parietal cells and neutrophils. $H_2R$ is best known for its central role in gastric acid secretion but has also been reported to be involved in increased vascular permeability and airway mucus production. Antagonists of $H_2R$ are widely used in treating peptic ulcers and gastroesophageal reflux disease. These drugs are also used extensively to reduce the risk of gastrointestinal (GI) bleeding associated with severe upper GI ulcers and GI stress in the inpatient setting.

The $H_3R$ is primarily found in the CNS and peripheral nerves innervating cardiac, bronchial, and GI tissue. $H_3R$ signaling regulates the release of multiple neurotransmitters, such as acetylcholine, dopamine, serotonin, and histamine itself (where it acts as a CNS autoreceptor). In the CNS, $H_3R$ participates in the processes of cognition, memory, sleep, and feeding behaviors. $H_3R$ antagonists may be used potentially for treating cognition disorders (such as Alzheimer's disease), sleep and wakefulness disorders, attention disorders, and metabolic disorders (especially related to obesity).

Existence of the $H_4R$ was predicted in the early 1990s, but its cloning by multiple groups was not reported until 2000. In contrast to the other histamine receptors, the $H_4R$ has a distinctly selective expression profile in bone marrow and on certain types of hematopoietic cells. $H_4R$ signaling modulates the function of mast cells, eosinophils, dendritic cells, and subsets of T cells. The $H_4R$ appears to control multiple behaviors of these cells, such as activation, migration, and cytokine and chemokine production (Zhang M, Thurmond R L, and Dunford P J *Pharmacology & Therapeutics*. 2007).

Of the 4 known histamine receptors, $H_1R$, $H_2R$ and $H_4R$ have been shown clearly to affect inflammation and other immune responses and are proposed therapeutic targets for treating immune and inflammatory disorders (Jutel et al., 2002; Akdis & Simons, 2006). The $H_1R$ was the first described histamine receptor, and ligands targeting this receptor were initially developed in the 1930s and in widespread use by the 1940s. Common $H_1R$ antagonist drugs currently approved for use include systemic agents such as diphenhydramine (Benadryl, also used topically), cetirizine (Zyrtec), fexofenadine (Allegra), loratadine (Claritin) and desloratadine (Clarinex), and topical agents such as olopatadine (Patanol, Pataday, Patanase), ketotifen, azelastine (Optivar, Astelin) and epinastine (Elestat). Traditional uses have included allergic diseases and reactions such as asthma, rhinitis, and other chronic obstructive pulmonary disorders, ocular disorders such as allergic conjunctivitis, and pruritus of varying etiologies.

However, $H_1$ receptor antagonists have certain deficiencies as therapeutic agents in the treatment of diseases where histamine is an important mediator. First, their effects are often only moderate and reduce allergic symptoms by only 40 to 50%. In particular, $H_1$ receptor antagonists, especially systemic agents, have little to no effect in relieving nasal congestion. In allergic asthma, despite the fact that histamine levels rapidly increase in the airways and in plasma (correlating with disease severity), $H_1$ receptor antagonists have largely failed as a therapeutic strategy, though some effect is seen with administration during the priming phase as opposed to the challenge phase (Thurmond R L et al., *Nat Rev Drug Discov*, 2008, 7:41-53). Additionally, although the efficacy of $H_1$ receptor antagonists against pruritus in acute urticarias, associated with hives and insect stings, and in chronic idiopathic urticaria is well proven, $H_1R$ antagonists are mostly ineffective in the treatment of atopic dermatitis-associated pruritus, with the only modest benefits derived from some first-generation compounds likely a consequence of their sedative properties (Sharpe, G. R. & Shuster, S. *Br. I Dermatol.* 1993, 129:575-9). Finally, sedation caused by H₁R antagonists that cross the blood-brain barrier, among other side effects, limits the utility of many H₁R antagonists in diseases for which they would otherwise be efficacious. These deficiencies render H₁R antagonists amenable to replacement by or supplementation with other agents.

Consequently, attention has focused on the more recently discovered H₄ receptor as a therapeutic target. Given the ability of H₄R to modulate the cellular function of eosinophils, mast cells, dendritic cells and T cells (M. Zhang et al., *Pharmacol Ther* 2007), it is natural to speculate that the H₄R may be involved in various inflammatory diseases, and that H₄R antagonists would have therapeutic potential (Jutel et al., 2006). Indeed, both in vitro and in vivo evidence has been demonstrated for the utility of H₄R antagonists as anti-inflammatory agents in inflammatory bowel disease (IBD) (Sander L E et al., *Gut* 2006; 55:498-504). The finding that H₄ receptor antagonists inhibit histamine-induced migration of mast cells and eosinophils in vitro and in vivo, both of which are important effector cells in the allergic response, raises the possibility that this class of compounds could reduce the allergic hyper-responsiveness developed upon repeated exposure to antigens, which is characterized by an increase in the number of mast cells and other inflammatory cells in the nasal and bronchial mucosa (Fung-Leung W P et al., Curr Opin Inves Drugs, 2004 5:11 1174-1182). In contrast to some of the H₁R antagonists, H₄R antagonists given during the allergen challenge phase of a mouse model of asthma are equally effective to those given during sensitization (Thurmond R L et al., *Nat Rev Drug Discov,* 2008, 7:41-53). In two recent mouse studies, a selective H₄R agonist was shown to induce itch, whereas these responses, and those of histamine, were blocked by pretreatment with H₄R antagonists. Similarly, histamine or H₄ receptor agonist-induced itch was markedly attenuated in H4 receptor-deficient animals (Dunford, P. J. et al., *J. Allergy Clin. Immunol,* 2007, 119:176-183). The presence of the H₄R in nasal tissue was first discovered by Nakaya et al. (Nakaya, M. et al., *Ann Otol Rhinol Laryngol,* 2004, 113: 552-557). In addition, a more recent finding showed that there is a significant increase in the level of H₄R in human nasal polyp tissue taken from patients with chronic rhinosinusitis (infection of the nose and nasal cavities) when compared to normal nasal mucosa. Jókűti et al. suggest that the administration of H₄R antagonists might be a new way to treat nasal polyps and chronic rhinosinusitis. The administration of H₄R antagonists may prevent the accumulation of eosinophils as a result of impaired cell chemotaxis toward polypous tissue (Jókűti, A. et al., *Cell Biol Int,* 2007, 31: 1367). Although scientific data on the role of the H₄R in rhinitis is limited, at present, it is the only indication for which an H₄R inverse agonist (CZC-13788) is reported to be in preclinical development (Hale, R. A. et al., *Drug News Perspect,* 2007, 20: 593-600).

Current research efforts include both a focus on H₄R selective agents and an alternate path toward dual H₁R/H₄R agents. Johnson & Johnson have developed a well-characterized H₄R antagonist, JNJ-7777120, which is 1000-fold selective over H₁, H₂, and H₃ receptors, and equipotent across human and several nonhuman species. An exemplary H₁R/H₄R dual agent has yet to publish as of the time of this writing, and the ideal proportion of H₁R versus H₄R antagonism is a nascent topic of debate. Nevertheless, the concept of dual activity via a single agent is well-precedented, and the design of multiply active ligands is a current topic in pharmaceutical discovery (Morphy R and Rankovic Z, *J Med. Chem.* 2005; 48(21):6523-43). Additional reports have shown potential for H₄R antagonists, or potentially, H₁R/H₄R dual antagonists, in the treatment of metabolic disorders such as obesity (Jorgensen E et al., *Neuroendocrinology.* 2007; 86(3):210-4), vascular or cardiovascular diseases such as atherosclerosis (Tanihide A et al., *TCM* 2006: 16(8): 280-4), inflammation and pain (Coruzzi G et al., *Eur J. Pharmacol.* 2007 Jun. 1; 563(1-3):240-4), rheumatoid arthritis (Grzybowska-Kowalczyk A et al., *Inflamm Res.* 2007 April; 56 Suppl 1:S59-60) and other inflammatory and autoimmune diseases including systemic lupus erythematosus (Zhang M, Thurmond R L, and Dunford P J *Pharmacology & Therapeutics.* 2007). What is clear is that a need still exists in the art for improved and varied antihistamines for the treatment of disease, and that compounds with H₄R and/or H₁R/H₄R antagonist activity may fill this need.

Histamine is reportedly implicated in allergic rhinitis by acting on three HR subtypes, the H₁R, H₃R and H₄R. For many years, the classical application of H₁R antagonists (antihistamines) has been the treatment of allergic rhinitis. H₁R antagonists relieve edema and vasoconstriction, both important symptoms of the disease, but these drugs do not affect the underlying inflammatory responses. After the discovery of the H₃R and H₄R subtypes, the traditional role for H₁R antagonists in rhinitis has been reappraised. It has been shown that the H₃R agonist (R)-α-methyl-histamine can induce the dilatation of nasal blood vessels and that this effect can be counteracted by the H₃R antagonist/H₄R agonist clobenpropit (Taylor-Clark, T., et al, *Pulm Pharm Ther,* 2008, 21: 455-460). Although a role for the H₄R cannot be ruled out, this H₃R antagonist-mediated mechanism in nasal decongestion has certainly caught the attention of scientists from Pfizer Inc. Recently, patient recruitment started for a Phase II clinical trial to test a H₃R antagonist (PF-03654746, unpublished structure) as a novel nasal decongestant in patients with seasonal allergic rhinitis. A dual target approach is being pursued by GSK that is currently recruiting patients to test a systemic H₁/H₃ antagonist (GSK835726, unpublished structure) for seasonal allergic rhinitis in a Phase I clinical trial. A second Phase I trial with another H₁/H₃ antagonist (GSK1004723, unpublished structure) for intranasal administration to treat rhinitis has recently been completed. With these compounds, the mode of action of the classical H₁R antagonist is combined with the potential clinical benefit of added nasal decongestion by H₃R blockade. The synergistic role of the H₁R and H₃R has been demonstrated in vivo in experiments performed at Schering-Plough. In view of the role of the H₄R in allergic rhinitis, other potential treatment paradigms may also be considered, such as combining H₁/H₄, H₃/H₄ or even H₁/H₃/H₄ antagonists/inverse agonist activity in the same molecule.

DETAILED DESCRIPTION OF THE INVENTION

Novel compounds and pharmaceutical compositions, certain of which have been found to inhibit the histamine type-4 receptor (H₄R) have been discovered, together with methods of synthesizing and using the compounds including methods for the treatment of histamine receptor-mediated diseases in a patient by administering the compounds.

Provided herein are compounds of structural Formula (I), or a salt thereof, wherein,

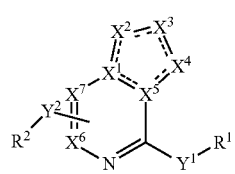

(I)

the ring comprising $X^1$-$X^5$ is aromatic;
$X^1$ and $X^5$ are independently chosen from C, CH and N;
$X^2$ is chosen from [C($R^6$)($R^7$)], $NR^8$, O and S;
$X^3$ is chosen from [C($R^9$)($R^{10}$)], $NR^{11}$, O and S;
$X^4$ is chosen from [C($R^{12}$)($R^{13}$)], $NR^{14}$, O and S;
$X^6$ is chosen from $CR^{18}$ and N;
$X^7$ is chosen from $CR^{19}$ and N;
$Y^1$ is chosen from a bond, lower alkyl, lower alkoxy, $OR^{15}$, $NR^{16}R^{17}$, and lower aminoalkyl;
$Y^2$ is chosen from a bond, lower alkyl, lower alkoxy, $OR^{20}$, $NR^{21}R^{22}$, S, C(O)NH$_2$, C(O)NHR$_{23}$, C(O)NR$_{23}$R$_{24}$ and lower aminoalkyl;
$R^1$ is selected from the group consisting of:
aryl, heterocycloalkyl, cycloalkyl, and heteroaryl, any of which may be optionally substituted, when $Y^1$ is a bond; and
null, when $Y^1$ is chosen from $OR^{15}$, $NR^{16}R^{17}$, lower alkyl, lower alkoxy, or lower aminoalkyl;
$R^2$ is chosen from alkyl, alkenyl, alkynyl, aryl, cycloalkyl, heterocycloalkyl, and heteroaryl, any of which may be optionally substituted;
$R^6$, $R^7$, $R^9$, $R^{10}$, $R^{12}$, $R^{13}$, $R^{18}$, and $R^{19}$ are independently chosen from null, hydrogen, alkyl, alkenyl, alkynyl, heteroalkyl, alkoxy, halogen, haloalkyl, perhaloalkyl, amino, aminoalkyl, amido, carboxyl, acyl, hydroxy, cyano, nitro, aryl, arylalkyl, cycloalkyl, cycloalkylalkyl, heterocycloalkyl, heterocycloalkylalkyl, heteroaryl, and heteroarylalkyl, any of which may be optionally substituted;
$R^8$, $R^{11}$, and $R^{14}$ are independently chosen from null, hydrogen, alkyl, heteroalkyl, alkoxy, haloalkyl, perhaloalkyl, aminoalkyl, C-amido, carboxyl, acyl, hydroxy, aryl, arylalkyl, cycloalkyl, cycloalkylalkyl, heterocycloalkyl, heterocycloalkylalkyl, heteroaryl, and heteroarylalkyl, any of which may be optionally substituted;
$R^{15}$, $R^{16}$, $R^{20}$, and $R^{21}$ are independently chosen from aminoalkyl, alkylaminoalkyl, aryl, arylalkyl, cycloalkyl, cycloalkylalkyl, ether, heterocycloalkyl, lower alkylaminoheterocycloalkyl, heterocycloalkylalkyl, heteroaryl, and heteroarylalkyl, any of which may be optionally substituted;
$R^{17}$ and $R^{22}$ are independently chosen from hydrogen, aminoalkyl, alkylaminoalkyl aryl, arylalkyl, cycloalkyl, cycloalkylalkyl, ether, heterocycloalkyl, lower alkylaminoheterocycloalkyl, heterocycloalkylalkyl, heteroaryl, and heteroarylalkyl, any of which may be optionally substituted; and
$R_{23}$ and $R_{24}$ are independently chosen from hydrogen, alkyl, alkenyl, alkynyl, heteroalkyl, alkoxy, halogen, haloalkyl, perhaloalkyl, perhaloalkoxy, amino, aminoalkyl, amido, carboxyl, acyl, hydroxy, cyano, nitro, aryl, arylalkyl, cycloalkyl, cycloalkylalkyl, heterocycloalkyl, heterocycloalkylalkyl, heteroaryl, and heteroarylalkyl, any of which may be optionally substituted.

Certain compounds disclosed herein may possess useful histamine receptor inhibitory activity, and may be used in the treatment or prophylaxis of a disease or condition in which $H_4R$ plays an active role. Thus, in broad aspect, certain embodiments also provide pharmaceutical compositions comprising one or more compounds disclosed herein together with a pharmaceutically acceptable carrier, as well as methods of making and using the compounds and compositions. Certain embodiments provide methods for inhibiting $H_4R$. Other embodiments provide methods for treating a $H_4R$-mediated disorder in a patient in need of such treatment, comprising administering to said patient a therapeutically effective amount of a compound or composition according to the present invention. Also provided is the use of certain compounds disclosed herein for use in the manufacture of a medicament for the treatment of a disease or condition ameliorated by the inhibition of $H_4R$.

In certain embodiments provided herein, at least two of $X^1$-$X^7$ are ring heteroatoms.

In certain embodiments provided herein,
$X^7$ is N;
$X^6$ is $CR^{18}$; and
$Y^1$ and $Y^2$ are each independently a bond.

Provided herein are compounds of structural Formula (II), or a salt thereof, wherein,

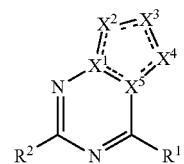

(II)

$X^1$ and $X^5$ are independently chosen from C and N;
$X^2$ is chosen from [C($R^6$)($R^7$)], and $NR^8$;
$X^3$ is chosen from [C($R^9$)($R^{10}$)], and $NR^{11}$;
$X^4$ is chosen from [C($R^{12}$)($R^{13}$)], and $NR^{14}$;
$R^1$ is chosen from aryl, heterocycloalkyl, cycloalkyl, and heteroaryl, any of which may be optionally substituted;
$R^2$ is chosen from alkyl, alkenyl, alkynyl, aryl, cycloalkyl, heterocycloalkyl and heteroaryl, any of which may be optionally substituted;
$R^6$, $R^7$, $R^9$, $R^{10}$, $R^{12}$, and $R^{13}$ are independently chosen from null, hydrogen, alkyl, alkenyl, alkynyl, heteroalkyl, alkoxy, halogen, haloalkyl, perhaloalkyl, amino, aminoalkyl, amido, carboxyl, acyl, hydroxy, cyano, nitro, aryl, arylalkyl, cycloalkyl, cycloalkylalkyl, heterocycloalkyl, heterocycloalkylalkyl, heteroaryl, and heteroarylalkyl, any of which may be optionally substituted; and
$R^8$, $R^{11}$, and $R^{14}$ are independently chosen from null, hydrogen, alkyl, heteroalkyl, alkoxy, haloalkyl, perhaloalkyl, aminoalkyl, C-amido, carboxyl, acyl, hydroxy, aryl, arylalkyl, cycloalkyl, cycloalkylalkyl, heterocycloalkyl, heterocycloalkylalkyl, heteroaryl, and heteroarylalkyl, any of which may be optionally substituted.

In certain embodiments provided herein,
$X^7$ is $CR^{19}$;
$X^6$ is N; and
$Y^1$ and $Y^2$ are each independently a bond.

Provided herein are compounds of structural Formula (III), or a salt thereof, wherein,

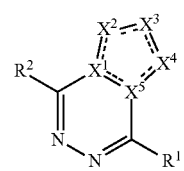

(III)

$X^1$ and $X^5$ are independently chosen from C and N;
$X^2$ is chosen from [C($R^6$)($R^7$)], and $NR^8$;
$X^3$ is chosen from [C($R^9$)($R^{10}$)], and $NR^{11}$;
$X^4$ is chosen from [C($R^{12}$)($R^{13}$)], and $NR^{14}$;
$R^1$ is chosen from aryl, heterocycloalkyl, cycloalkyl, and heteroaryl, any of which may be optionally substituted;
$R^2$ is chosen from alkyl, alkenyl, alkynyl, aryl, cycloalkyl, heterocycloalkyl and heteroaryl, any of which may be optionally substituted;

$R^6$, $R^7$, $R^9$, $R^{10}$, $R^{12}$, and $R^{13}$ are independently chosen from null, hydrogen, alkyl, alkenyl, alkynyl, heteroalkyl, alkoxy, halogen, haloalkyl, perhaloalkyl, amino, aminoalkyl, amido, carboxyl, acyl, hydroxy, cyano, nitro, aryl, arylalkyl, cycloalkyl, cycloalkylalkyl, heterocycloalkyl, heterocycloalkylalkyl, heteroaryl, and heteroarylalkyl, any of which may be optionally substituted; and $R^8$, $R^{11}$, and $R^{14}$ are independently chosen from null, hydrogen, alkyl, heteroalkyl, alkoxy, haloalkyl, perhaloalkyl, aminoalkyl, C-amido, carboxyl, acyl, hydroxy, aryl, arylalkyl, cycloalkyl, cycloalkylalkyl, heterocycloalkyl, heterocycloalkylalkyl, heteroaryl, and heteroarylalkyl, any of which may be optionally substituted.

In certain embodiments provided herein, $X^7$ is $CR^{19}$;

$X^6$ is $CR^{18}$; and $Y^1$ and $Y^2$ are each independently a bond.

Provided herein are compounds of structural Formula (IV), or a salt thereof, wherein,

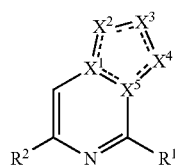

(IV)

$X^1$ and $X^5$ are independently chosen from C and N;

$X^2$ is chosen from $[C(R^6)(R^7)]$, and $NR^8$;

$X^3$ is chosen from $[C(R^9)(R^{10})]$, and $NR^{11}$;

$X^4$ is chosen from $[C(R^{12})(R^{13})]$, and $NR^{14}$;

$R^1$ is chosen from aryl, heterocycloalkyl, cycloalkyl, and heteroaryl, any of which may be optionally substituted;

$R^2$ is chosen from alkyl, alkenyl, alkynyl, aryl, cycloalkyl, heterocycloalkyl and heteroaryl, any of which may be optionally substituted;

$R^6$, $R^7$, $R^9$, $R^{10}$, $R^{12}$, and $R^{13}$ are independently chosen from null, hydrogen, alkyl, alkenyl, alkynyl, heteroalkyl, alkoxy, halogen, haloalkyl, perhaloalkyl, amino, aminoalkyl, amido, carboxyl, acyl, hydroxy, cyano, nitro, aryl, arylalkyl, cycloalkyl, cycloalkylalkyl, heterocycloalkyl, heterocycloalkylalkyl, heteroaryl, and heteroarylalkyl, any of which may be optionally substituted; and $R^8$, $R^{11}$, and $R^{14}$ are independently chosen from null, hydrogen, alkyl, heteroalkyl, alkoxy, haloalkyl, perhaloalkyl, aminoalkyl, C-amido, carboxyl, acyl, hydroxy, aryl, arylalkyl, cycloalkyl, cycloalkylalkyl, heterocycloalkyl, heterocycloalkylalkyl, heteroaryl, and heteroarylalkyl, any of which may be optionally substituted.

In certain embodiments, $X^3$ is chosen from $[C(R^9)(R^{10})]$, and $NR^{11}$;

$R^{10}$ is chosen from null, hydrogen, and lower alkyl; and $R^{18}$ and $R^{19}$ are independently chosen from null, lower alkyl, and hydrogen.

Provided herein are compounds of structural Formula (V), or a salt thereof, wherein,

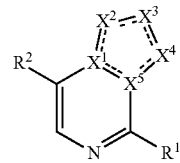

(V)

$X^1$ and $X^5$ are independently chosen from C and N;

$X^2$ is chosen from $[C(R^6)(R^7)]$, and $NR^8$;

$X^3$ is chosen from $[C(R^9)(R^{10})]$, and $NR^{11}$;

$X^4$ is chosen from $[C(R^{12})(R^{13})]$, and $NR^{14}$;

$R^1$ is chosen from aryl, heterocycloalkyl, cycloalkyl, and heteroaryl, any of which may be optionally substituted;

$R^2$ is chosen from alkyl, alkenyl, alkynyl, aryl, cycloalkyl, heterocycloalkyl and heteroaryl, any of which may be optionally substituted;

$R^6$, $R^7$, $R^9$, $R^{10}$, $R^{12}$, and $R^{13}$ are independently chosen from null, hydrogen, alkyl, alkenyl, alkynyl, heteroalkyl, alkoxy, halogen, haloalkyl, perhaloalkyl, amino, aminoalkyl, amido, carboxyl, acyl, hydroxy, cyano, nitro, aryl, arylalkyl, cycloalkyl, cycloalkylalkyl, heterocycloalkyl, heterocycloalkylalkyl, heteroaryl, and heteroarylalkyl, any of which may be optionally substituted; and $R^8$, $R^{11}$, and $R^{14}$ are independently chosen from null, hydrogen, alkyl, heteroalkyl, alkoxy, haloalkyl, perhaloalkyl, aminoalkyl, C-amido, carboxyl, acyl, hydroxy, aryl, arylalkyl, cycloalkyl, cycloalkylalkyl, heterocycloalkyl, heterocycloalkylalkyl, heteroaryl, and heteroarylalkyl, any of which may be optionally substituted.

In certain embodiments, compounds have structural formula (V):

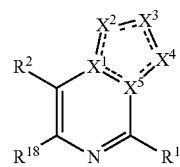

(V)

or a salt thereof, wherein:

$X^1$ and $X^5$ are independently chosen from C and N;

$X^2$ is chosen from $[C(R^6)(R^7)]$, $NR^8$, O and S;

$X^3$ is chosen from $[C(R^9)(R^{10})]$, and $NR^{11}$;

$X^4$ is chosen from $[C(R^{12})(R^{13})]$, $NR^{14}$, O and S;

$R^1$ is chosen from aryl, heterocycloalkyl, cycloalkyl, and heteroaryl, any of which may be optionally substituted;

$R^2$ is chosen from aryl, cycloalkyl, heterocycloalkyl, and heteroaryl, any of which may be optionally substituted;

$R^6$, $R^7$, $R^9$, $R^{12}$, and $R^{13}$ are independently chosen from null, hydrogen, alkyl, alkynyl, heteroalkyl, alkoxy, halogen, haloalkyl, perhaloalkyl, amino, aminoalkyl, amido, carboxyl, acyl, hydroxy, cyano, nitro, aryl, arylalkyl, cycloalkyl, cycloalkylalkyl, heterocycloalkyl, heterocycloalkylalkyl, heteroaryl, and heteroarylalkyl, any of which may be optionally substituted;

$R^{10}$ is chosen from null, hydrogen, and lower alkyl;

$R^8$, $R^{11}$, and $R^{14}$ are independently chosen from null, hydrogen, alkyl, heteroalkyl, alkoxy, haloalkyl, perhaloalkyl, aminoalkyl, C-amido, carboxyl, acyl, hydroxy, aryl, arylalkyl, cycloalkyl, cycloalkylalkyl, heterocycloalkyl, heterocycloalkylalkyl, heteroaryl, and heteroarylalkyl, any of which may be optionally substituted; and $R^{18}$ is chosen from lower alkyl and hydrogen.

In certain embodiments:

R$^1$ is chosen from phenyl, monocyclic 4- to 7-membered heterocycloalkyl, monocyclic 4- to 7-membered cycloalkyl, and monocyclic 5- to 6-membered heteroaryl, any of which may be optionally substituted;

R$^2$ is chosen from phenyl, monocyclic 5- to 7-membered cycloalkyl, monocyclic 5- to 7-membered heterocycloalkyl, monocyclic 5- to 6-membered heteroaryl, and heteroarylalkyl any of which may be optionally substituted.

In certain embodiments, R$^6$, R$^8$, R$^{11}$, R$^{12}$, R$^{13}$, and R$^{14}$ are independently chosen from null and hydrogen.

In certain embodiments, compounds of Formula I have a structure chosen from:

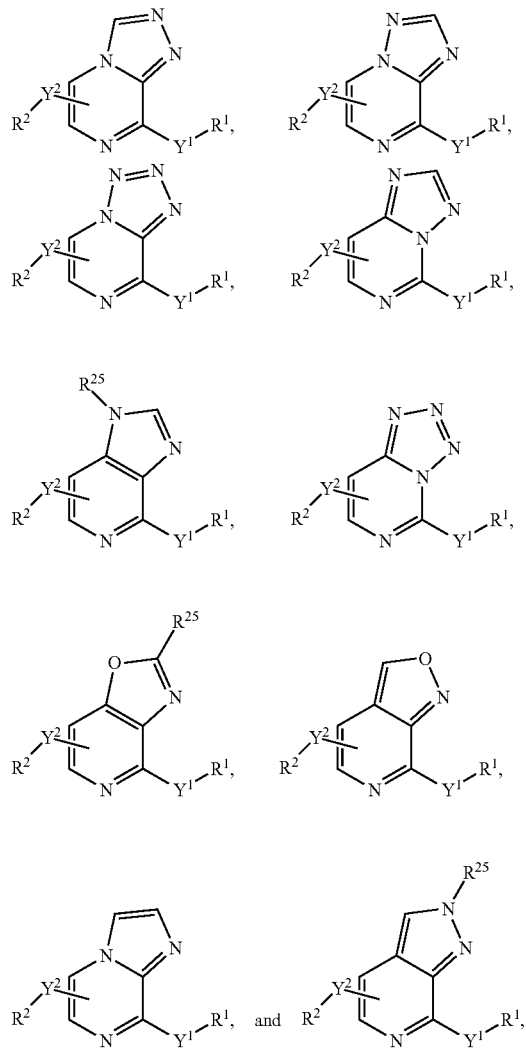

wherein:

R$^{25}$ is chosen from hydrogen, alkyl, alkenyl, alkynyl, heteroalkyl, alkoxy, halogen, haloalkyl, perhaloalkyl, perhaloalkoxy, amino, aminoalkyl, amido, carboxyl, acyl, hydroxy, cyano, nitro, aryl, arylalkyl, cycloalkyl, cycloalkylalkyl, heterocycloalkyl, heterocycloalkylalkyl, heteroaryl, and heteroarylalkyl, any of which may be optionally substituted; and all other groups are as disclosed in Formula I.

In certain embodiments, compounds of Formula I have a structure chosen from:

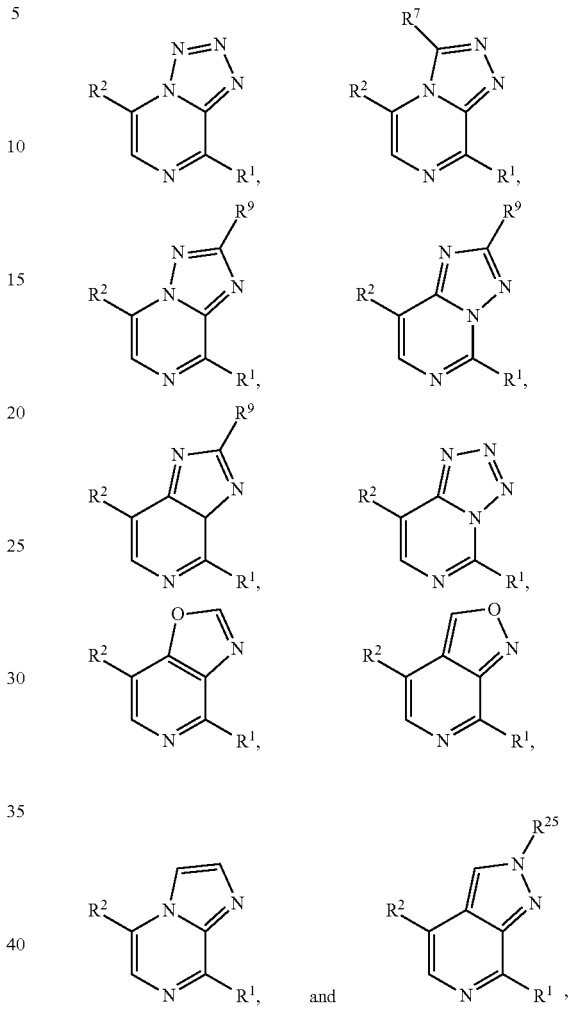

wherein:

R$^1$ is chosen from phenyl, monocyclic 4- to 7-membered heterocycloalkyl, monocyclic 4- to 7-membered cycloalkyl, and monocyclic 5- to 6-membered heteroaryl, any of which may be optionally substituted;

R$^2$ is chosen from alkyl, monocyclic cycloalkyl, monocyclic heterocycloalkyl and monocyclic heteroaryl, any of which may be optionally substituted;

R$^7$ and R$^9$ are independently chosen from null, hydrogen, alkyl, alkynyl, heteroalkyl, alkoxy, halogen, haloalkyl, perhaloalkyl, amino, aminoalkyl, amido, carboxyl, acyl, hydroxy, cyano, nitro, aryl, arylalkyl, cycloalkyl, cycloalkylalkyl, heterocycloalkyl, heterocycloalkylalkyl, heteroaryl, and heteroarylalkyl, any of which may be optionally substituted; and R$^{25}$ is chosen from hydrogen, alkyl, alkenyl, alkynyl, heteroalkyl, alkoxy, halogen, haloalkyl, perhaloalkyl, perhaloalkoxy, amino, aminoalkyl, amido, carboxyl, acyl, hydroxy, cyano, nitro, aryl, arylalkyl, cycloalkyl, cycloalkylalkyl, heterocycloalkyl, heterocycloalkylalkyl, heteroaryl, and heteroarylalkyl, any of which may be optionally substituted.

In certain embodiments, compounds of Formula I have a structure chosen from:

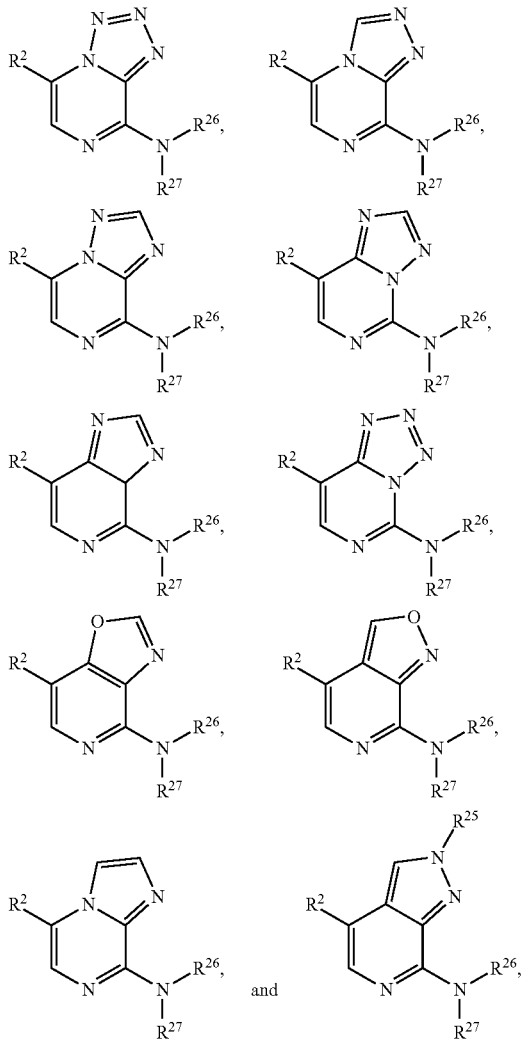

wherein

R² is chosen from alkyl, monocyclic cycloalkyl, monocyclic heterocycloalkyl and monocyclic heteroaryl, any of which may be optionally substituted;

R²⁵ is chosen from hydrogen, alkyl, alkenyl, alkynyl, heteroalkyl, alkoxy, halogen, haloalkyl, perhaloalkyl, perhaloalkoxy, amino, aminoalkyl, amido, carboxyl, acyl, hydroxy, cyano, nitro, aryl, arylalkyl, cycloalkyl, cycloalkylalkyl, heterocycloalkyl, heterocycloalkylalkyl, heteroaryl, and heteroarylalkyl, any of which may be optionally substituted; and R²⁶ and R²⁷ are independently chosen from hydrogen, alkyl, alkenyl, alkynyl, heteroalkyl, alkoxy, halogen, haloalkyl, perhaloalkyl, amino, aminoalkyl, amido, acyl, hydroxy, cyano, nitro, aryl, arylalkyl, cycloalkyl, cycloalkylalkyl, heterocycloalkyl, heterocycloalkylalkyl, heteroaryl, and heteroarylalkyl, any of which may be optionally substituted; or R²⁶ and R²⁷ together with the nitrogen to which they are attached may combine to form heterocycloalkyl or heteroaryl, either of which is attached through a ring nitrogen to the core and either of which may be optionally substituted.

In certain embodiments, compounds of Formula I have a structure chosen from:

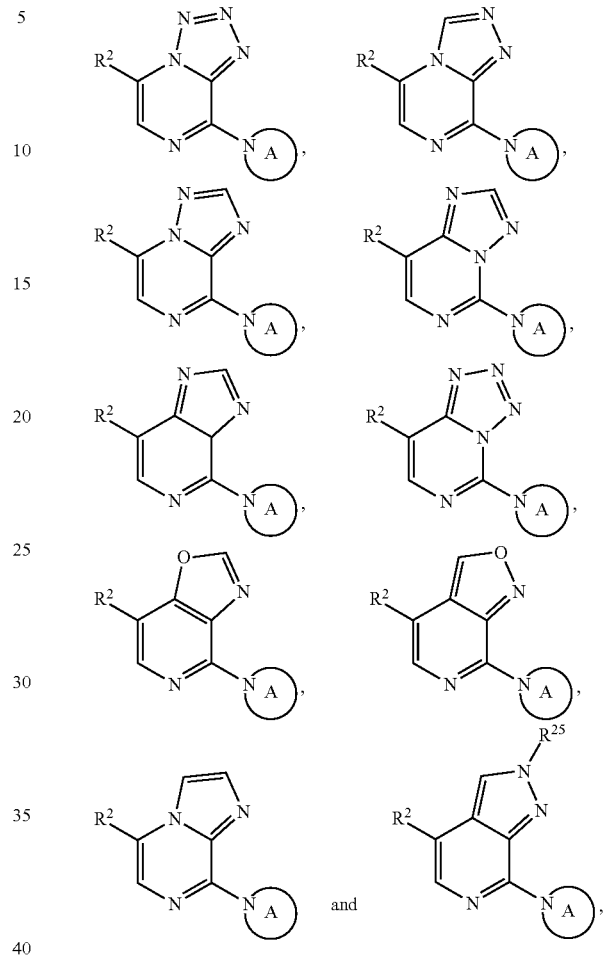

wherein

A is chosen from a monocyclic heterocycloalkyl and a monocyclic heteroaryl, either of which is attached through a ring nitrogen to the core and either of which may be optionally substituted;

R² is chosen from alkyl, phenyl, monocyclic cycloalkyl, monocyclic heterocycloalkyl and monocyclic heteroaryl, any of which may be optionally substituted; and R²⁵ is chosen from hydrogen, alkyl, alkenyl, alkynyl, heteroalkyl, alkoxy, halogen, haloalkyl, perhaloalkyl, perhaloalkoxy, amino, aminoalkyl, amido, carboxyl, acyl, hydroxy, cyano, nitro, aryl, arylalkyl, cycloalkyl, cycloalkylalkyl, heterocycloalkyl, heterocycloalkylalkyl, heteroaryl, and heteroarylalkyl, any of which may be optionally substituted.

In certain embodiments, A is four- to seven-membered.

In certain embodiments, R²⁵ is chosen from hydrogen and methyl.

In certain embodiments:

X² is chosen from [C(R⁶)(R⁷)], and NR⁸;

X⁴ is chosen from [C(R¹²)(R¹³)], and NR¹⁴;

R² is chosen from monocyclic 5- to 7-membered heterocycloalkyl, phenyl, and monocyclic 5- to 6-membered heteroaryl, any of which may be optionally substituted; and R¹⁸ is chosen from methyl and hydrogen.

In certain embodiments, R² is chosen from phenyl, furan, thiophene, pyrrole, pyrroline, pyrrolidine, oxazole, thiazole, imidazole, pyrazole, imidazoline, imidazolidine, pyrazoline, pyrazolidine, isoxazole, isothiazole, oxadiazole, thiadiazole, triazole, pyran, pyridine, piperidine, morpholine, thiomorpholine, piperazine, pyridazine, pyrimidine, and pyrazine.

In certain embodiments, $R^1$ is optionally substituted monocyclic 4- to 7-membered heterocycloalkyl.

In certain embodiments,
$X^1$ is C;
$X^2$ is $NR^8$;
$X^4$ is $NR^{14}$;
$X^5$ is N; and
$R^9$ is chosen from null, hydrogen, alkyl, alkoxy, halogen, haloalkyl, acyl perhaloalkyl, amino, aminoalkyl, hydroxy, cyano, any of which may be optionally substituted.

Provided herein are compounds of structural Formula (VI):

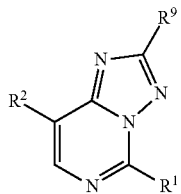

(VI)

or a salt thereof, wherein:
$R^1$ is optionally substituted monocyclic 4- to 7-membered heterocycloalkyl; and
$R^2$ is chosen from monocyclic 5- to 7-membered heterocycloalkyl, phenyl, and monocyclic 5- to 6-membered heteroaryl, any of which may be optionally substituted; and
$R^9$ is chosen from null, hydrogen, and lower alkyl, In certain embodiments,
$X^1$ is N;
$X^2$ is chosen from $[C(R^6)(R^7)]$, and $NR^8$;
$X^4$ is $NR^{14}$;
$X^5$ is C;
$R^1$ is chosen from phenyl, monocyclic 4- to 7-membered heterocycloalkyl, monocyclic 4- to 7-membered cycloalkyl, and monocyclic 5- to 6-membered heteroaryl, any of which may be optionally substituted;
$R^1$ is optionally substituted monocyclic 4- to 7-membered heterocycloalkyl; and
$R^2$ is chosen from monocyclic 5- to 7-membered heterocycloalkyl, phenyl, and monocyclic 5- to 6-membered heteroaryl, either of which may be optionally substituted.

Also provided herein are compounds of structural Formula (VII):

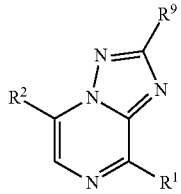

(VII)

or a salt thereof, wherein:
$R^1$ is chosen from phenyl, monocyclic 4- to 7-membered heterocycloalkyl, monocyclic 4- to 7-membered cycloalkyl, and monocyclic 5- to 6-membered heteroaryl, any of which may be optionally substituted;

$R^2$ is chosen from phenyl, furan, thiophene, pyrrole, pyrroline, pyrrolidine, oxazole, thiazole, imidazole, pyrazole, imidazoline, imidazolidine, pyrazoline, pyrazolidine, isoxazole, isothiazole, oxadiazole, thiadiazole, triazole, pyran, pyridine, piperidine, morpholine, thiomorpholine, piperazine, pyridazine, pyrimidine, and pyrazine, any of which may be optionally substituted; and
$R^9$ is chosen from hydrogen, lower alkyl, lower alkoxy, halogen, lower haloalkyl, lower amino, lower aminoalkyl, hydroxy, cyano, any of which may be optionally substituted.

In certain embodiments,
$R^1$ is chosen from piperazine and azetidine, either of which may be optionally substituted with one to three substituents chosen from lower alkyl and lower amino;
$R^2$ is chosen from phenyl, furan, thiophene, and thiazole, any of which may be optionally substituted with one to three substituents chosen from halogen, lower alkyl, lower haloalkyl, lower alkoxy, lower haloalkoxy, cyano, lower amino, hydroxy, and nitro.

Also provided herein are compounds of structural Formula (VIII):

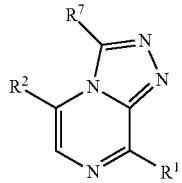

(VIII)

or a salt thereof, wherein:
$R^1$ is optionally substituted monocyclic 4- to 7-membered heterocycloalkyl;
$R^2$ is chosen from monocyclic 5- to 7-membered heterocycloalkyl, phenyl, and monocyclic 5- to 6-membered heteroaryl, either of which may be optionally substituted with one to three substituents chosen from halogen, lower alkyl, lower haloalkyl, lower alkoxy, lower haloalkoxy, cyano, lower amino, hydroxy, and nitro; and
$R^7$ is chosen from hydrogen, alkyl, alkoxy, halogen, haloalkyl, perhaloalkyl, amino, aminoalkyl, hydroxy, cyano, any of which may be optionally substituted.

Also provided herein are compounds of structural Formula (IX)

(IX)

or a salt thereof, wherein:
$R^1$ is optionally substituted monocyclic 4- to 7-membered heterocycloalkyl; and
$R^2$ is chosen from monocyclic 5- to 7-membered heterocycloalkyl, phenyl and monocyclic 5- to 6-membered heteroaryl, either of which may be optionally substituted with one to three substituents chosen from halogen, lower alkyl, lower haloalkyl, lower alkoxy, lower haloalkoxy, cyano, lower amino, hydroxy, and nitro.

Also provided herein are compounds of structural Formula (X)

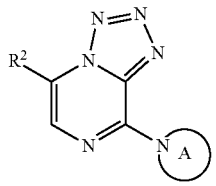

or a salt thereof, wherein:

A is chosen from a monocyclic 4- to 7-membered heterocycloalkyl and a monocyclic 5- to 6-membered heteroaryl, either of which is attached through a ring nitrogen to the core and either of which may be optionally substituted; and $R^2$ is chosen from phenyl, furan, thiophene, pyrrole, pyrroline, pyrrolidine, oxazole, thiazole, imidazole, pyrazole, imidazoline, imidazolidine, pyrazoline, pyrazolidine, isoxazole, isothiazole, oxadiazole, thiadiazole, triazole, pyran, pyridine, piperidine, morpholine, thiomorpholine, piperazine, pyridazine, pyrimidine, and pyrazine, any of which may be optionally substituted.

Also provided herein are compounds of structural Formula (XI)

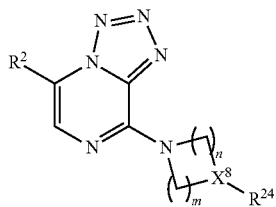

or a salt thereof, wherein:

$X^8$ is chosen from CH and N;

m and n are each an integer chosen from 1 and 2;

$R^2$ is chosen from phenyl, furan, thiophene, and thiazole, any of which may be optionally substituted with one to three substituents chosen from halogen, lower alkyl, lower haloalkyl, lower alkoxy, lower haloalkoxy, cyano, lower amino, hydroxy, and nitro; and $R^{24}$ is chosen from hydrogen, amino, and lower alkyl.

In certain embodiments, $X^8$ is CH;

m and n are each 1; and $R^{24}$ is chosen from hydrogen, amino, and lower alkyl.

In certain embodiments, $R^{24}$ is amino.

In certain embodiments, $R^{24}$ is $NHCH_3$.

In certain embodiments, $X^8$ is N;

m and n are each 2; and $R^{24}$ is chosen from hydrogen and lower alkyl.

In certain embodiments, $R^{24}$ is chosen from hydrogen and methyl.

In certain embodiments, $R^{24}$ is methyl.

In certain embodiments provided herein, $R^2$ is chosen from phenyl, furan, thiophene, pyrrole, pyrroline, pyrrolidine, oxazole, thiazole, imidazole, pyrazole, imidazoline, imidazolidine, pyrazoline, pyrazolidine, isoxazole, isothiazole, oxadiazole, thiadiazole, triazole, pyran, pyridine, piperidine, morpholine, thiomorpholine, piperazine, pyridazine, pyrimidine, and pyrazine.

Also provided herein is a pharmaceutical composition comprising a compound as recited herein together with a pharmaceutically acceptable carrier.

Also provided herein is a pharmaceutical composition comprising:
a. a compound as recited herein;
b. another therapeutic agent; and
c. one or more pharmaceutically acceptable carriers or adjuvants.

In certain embodiments, the other therapeutic agent is an $H_1R$ antagonist.

In certain embodiments, the $H_1R$ antagonist is chosen from acrivastine, alcaftadine, antazoline, azelastine, bromazine, brompheniramine, cetirizine, chlorpheniramine, clemastine, desloratidine, diphenhydramine, diphenylpyraline, ebastine, emedastine, epinastine, fexofenadine, hydroxyzine, ketotifen, levocabastine, levocetirizine, loratidine, methdilazine, mizolastine, promethazine, olopatadine, and triprolidine.

In certain embodiments, the other therapeutic agent is an $H_3R$ antagonist.

In certain embodiments, the other therapeutic agents are an $H_3R$ antagonist and an $H_1R$ antagonist.

In certain embodiments, the other therapeutic agent is an intranasal corticosteroid.

In certain embodiments, the intranasal corticosteroid is chosen from fluticasone, budesonide, beclomethasone, mometasone and ciclesonide.

Also provided herein is a method of treatment of an $H_4R$-mediated disease comprising the administration, to a patient in need thereof, of a therapeutically effective amount of a compound as recited herein.

In certain embodiments provided herein, said treatment is systemic.

In certain embodiments, said administration is topical.

In certain embodiments, said disease is chosen from an inflammatory disease, an autoimmune disease, an allergic disorder, and an ocular disorder.

In certain embodiments, disease is chosen from pruritus, eczema, atopic dermatitis, asthma, chronic obstructive pulmonary disease (COPD), allergic rhinitis, non-allergic rhinitis, rhinosinusitis, nasal inflammation, nasal congestion, sinus congestion, otic inflammation dry eye, ocular inflammation, allergic conjunctivitis, vernal conjunctivitis, vernal keratoconjunctivitis, and giant papillary conjunctivitis.

In certain embodiments, said topical administration is to the skin.

In certain embodiments, said topical administration is to the eye.

In certain embodiments, said topical administration is intranasal, otic or by inhalation.

Also provided herein is a method of inhibition of $H_4R$ comprising contacting $H_4R$ with a compound as recited herein.

In certain embodiments, the contacting of $H_4R$ with a compound as disclosed herein causes inhibition which is noncompetitive with histamine.

Also provided herein is a method of treatment of the pain or inflammation resulting from cataract surgery, comprising delivering to a patient in need of such treatment with a therapeutically effective amount of a compound as recited herein.

Also provided herein is a method of treatment of an $H_4R$-mediated disease comprising the administration of:
a therapeutically effective amount of a compound as recited herein; and
another therapeutic agent.

Also provided herein is a method for achieving an effect in a patient comprising the administration of a therapeutically effective amount of a compound as recited herein to a patient, wherein the effect is chosen from reduction in the number of mast cells, inhibition of inflammatory cell (e.g., granulocytes including eosinophils, basophils, and neutrophils, mast cells, lymphocytes, and dendritic cells) migration optionally to the nasal mucosa, the ear, the eye, or the wound site, reduction in inflammatory markers, reduction in inflammatory cytokines, reduction in scratching, relief of symptoms and/or signs of nasal congestion from allergic and non-allergic causes, decreased watering or redness of the eyes, and reduction in ocular pain.

Also provided herein is a compound as recited herein for use as a medicament.

Also provided herein is a compound as recited herein for use in the manufacture of a medicament for the prevention or treatment of a disease or condition ameliorated by the inhibition of $H_4R$.

As used herein, the terms below have the meanings indicated.

When ranges of values are disclosed, and the notation "from $n_1$ ... to $n_2$" is used, where $n_1$ and $n_2$ are the numbers, then unless otherwise specified, this notation is intended to include the numbers themselves and the range between them. This range may be integral or continuous between and including the end values. By way of example, the range "from 2 to 6 carbons" is intended to include two, three, four, five, and six carbons, since carbons come in integer units. Compare, by way of example, the range "from 1 to 3 μM (micromolar)," which is intended to include 1 μM, 3 μM, and everything in between to any number of significant figures (e.g., 1.255 μM, 2.1 μM, 2.9999 μM, etc.).

The term "about," as used herein, is intended to qualify the numerical values which it modifies, denoting such a value as variable within a margin of error. When no particular margin of error, such as a standard deviation to a mean value given in a chart or table of data, is recited, the term "about" should be understood to mean that range which would encompass the recited value and the range which would be included by rounding up or down to that figure as well, taking into account significant figures.

The term "acyl," as used herein, alone or in combination, refers to a carbonyl attached to an alkenyl, alkyl, aryl, cycloalkyl, heteroaryl, heterocycle, or any other moiety where the atom attached to the carbonyl is carbon. An "acetyl" group refers to a —C(O)CH₃ group. An "alkylcarbonyl" or "alkanoyl" group refers to an alkyl group attached to the parent molecular moiety through a carbonyl group. Examples of such groups include methylcarbonyl and ethylcarbonyl. Examples of acyl groups include formyl, alkanoyl and aroyl.

The term "alkenyl," as used herein, alone or in combination, refers to a straight-chain or branched-chain hydrocarbon group having one or more double bonds and containing from 2 to 20 carbon atoms. In certain embodiments, said alkenyl will comprise from 2 to 6 carbon atoms. The term "alkenylene" refers to a carbon-carbon double bond system attached at two or more positions such as ethenylene [(—CH═CH—), (—C::C—)]. Examples of suitable alkenyl groups include ethenyl, propenyl, 2-methylpropenyl, 1,4-butadienyl and the like. Unless otherwise specified, the term "alkenyl" may include "alkenylene" groups.

The term "alkoxy," as used herein, alone or in combination, refers to an alkyl ether group, wherein the term alkyl is as defined below. Examples of suitable alkyl ether groups include methoxy, ethoxy, n-propoxy, isopropoxy, n-butoxy, iso-butoxy, sec-butoxy, tert-butoxy, and the like.

The term "alkyl," as used herein, alone or in combination, refers to a straight-chain or branched-chain alkyl group containing from 1 to 20 carbon atoms. In certain embodiments, said alkyl group will comprise from 1 to 10 carbon atoms. In further embodiments, said alkyl group will comprise from 1 to 6 carbon atoms. Alkyl groups may be optionally substituted as defined herein. Examples of alkyl groups include methyl, ethyl, n-propyl, isopropyl, n-butyl, isobutyl, sec-butyl, tert-butyl, pentyl, iso-amyl, hexyl, octyl, noyl and the like. The term "alkylene," as used herein, alone or in combination, refers to a saturated aliphatic group derived from a straight or branched chain saturated hydrocarbon attached at two or more positions, such as methylene (—CH₂—). Unless otherwise specified, the term "alkyl" may include "alkylene" groups.

The term "alkylamino," as used herein, alone or in combination, refers to an alkyl group attached to the parent molecular moiety through an amino group. Suitable alkylamino groups may be mono- or dialkylated, forming groups such as, for example, N-methylamino, N-ethylamino, N,N-dimethylamino, N,N-ethylmethylamino and the like.

The term "alkylidene," as used herein, alone or in combination, refers to an alkenyl group in which one carbon atom of the carbon-carbon double bond belongs to the moiety to which the alkenyl group is attached.

The term "alkylthio," as used herein, alone or in combination, refers to an alkyl thioether (R—S—) group wherein the term alkyl is as defined above and wherein the sulfur may be singly or doubly oxidized. Examples of suitable alkyl thioether groups include methylthio, ethylthio, n-propylthio, isopropylthio, n-butylthio, iso-butylthio, sec-butylthio, tert-butylthio, methanesulfonyl, ethanesulfinyl, and the like.

The term "alkynyl," as used herein, alone or in combination, refers to a straight-chain or branched chain hydrocarbon group having one or more triple bonds and containing from 2 to 20 carbon atoms. In certain embodiments, said alkynyl group comprises from 2 to 6 carbon atoms. In further embodiments, said alkynyl group comprises from 2 to 4 carbon atoms. The term "alkynylene" refers to a carbon-carbon triple bond attached at two positions such as ethynylene (—C:::C—, —C≡C—). Examples of alkynyl groups include ethynyl, propynyl, hydroxypropynyl, butyn-1-yl, butyn-2-yl, pentyn-1-yl, 3-methylbutyn-1-yl, hexyn-2-yl, and the like. Unless otherwise specified, the term "alkynyl" may include "alkynylene" groups.

The terms "amido" and "carbamoyl," as used herein, alone or in combination, refer to an amino group as described below attached to the parent molecular moiety through a carbonyl group, or vice versa. The term "C-amido" as used herein, alone or in combination, refers to a —C(═O)—NR₂ group with R as defined herein. The term "N-amido" as used herein, alone or in combination, refers to a RC(═O)NH— group, with R as defined herein. The term "acylamino" as used herein, alone or in combination, embraces an acyl group attached to the parent moiety through an amino group. An example of an "acylamino" group is acetylamino (CH₃C(O)NH—).

The term "amino," as used herein, alone or in combination, refers to —NRR', wherein R and R' are independently chosen from hydrogen, alkyl, acyl, heteroalkyl, aryl, cycloalkyl, heteroaryl, and heterocycloalkyl, any of which may themselves be optionally substituted. Additionally, R and R' may combine to form heterocycloalkyl, either of which may be optionally substituted.

The term "aryl," as used herein, alone or in combination, means a carbocyclic aromatic system containing one, two or three rings wherein such polycyclic ring systems are fused together. The term "aryl" embraces aromatic groups such as phenyl, naphthyl, anthracenyl, and phenanthryl.

The term "arylalkenyl" or "aralkenyl," as used herein, alone or in combination, refers to an aryl group attached to the parent molecular moiety through an alkenyl group.

The term "arylalkoxy" or "aralkoxy," as used herein, alone or in combination, refers to an aryl group attached to the parent molecular moiety through an alkoxy group.

The term "arylalkyl" or "aralkyl," as used herein, alone or in combination, refers to an aryl group attached to the parent molecular moiety through an alkyl group.

The term "arylalkynyl" or "aralkynyl," as used herein, alone or in combination, refers to an aryl group attached to the parent molecular moiety through an alkynyl group.

The term "arylalkanoyl" or "aralkanoyl" or "aroyl," as used herein, alone or in combination, refers to an acyl group derived from an aryl-substituted alkanecarboxylic acid such as benzoyl, naphthoyl, phenylacetyl, 3-phenylpropionyl (hydrocinnamoyl), 4-phenylbutyryl, (2-naphthyl)acetyl, 4-chlorohydrocinnamoyl, and the like.

The term aryloxy as used herein, alone or in combination, refers to an aryl group attached to the parent molecular moiety through an oxy.

The terms "benzo" and "benz," as used herein, alone or in combination, refer to the divalent group $C_6H_4=$ derived from benzene. Examples include benzothiophene and benzimidazole.

The term "carbamate," as used herein, alone or in combination, refers to an ester of carbamic acid (—NHCOO—) which may be attached to the parent molecular moiety from either the nitrogen or acid end, and which may be optionally substituted as defined herein.

The term "O-carbamyl" as used herein, alone or in combination, refers to a —OC(O)NRR' group, with R and R' as defined herein.

The term "N-carbamyl" as used herein, alone or in combination, refers to a ROC(O)NR'— group, with R and R' as defined herein.

The term "carbonyl," as used herein, when alone includes formyl [—C(O)H] and in combination is a —C(O)— group.

The term "carboxyl" or "carboxy," as used herein, refers to —C(O)OH or the corresponding "carboxylate" anion, such as is in a carboxylic acid salt. An "O-carboxy" group refers to a RC(O)O— group, where R is as defined herein. A "C-carboxy" group refers to a —C(O)OR groups where R is as defined herein.

The term "cyano," as used herein, alone or in combination, refers to —CN.

The term "cycloalkyl," or, alternatively, "carbocycle," as used herein, alone or in combination, refers to a saturated or partially saturated monocyclic, bicyclic or tricyclic alkyl group wherein each cyclic moiety contains from 3 to 12 carbon atom ring members and which may optionally be a benzo fused ring system which is optionally substituted as defined herein. In certain embodiments, said cycloalkyl will comprise from 5 to 7 carbon atoms. Examples of such cycloalkyl groups include cyclopropyl, cyclobutyl, cyclopentyl, cyclohexyl, cycloheptyl, tetrahydronaphthyl, indanyl, octahydronaphthyl, 2,3-dihydro-1H-indenyl, adamantyl and the like. "Bicyclic" and "tricyclic" as used herein are intended to include both fused ring systems, such as decahydronaphthalene, octahydronaphthalene as well as the multicyclic (multicentered) saturated or partially unsaturated type. The latter type of isomer is exemplified in general by bicyclo[1,1,1]pentane, camphor, adamantane, and bicyclo[3,2,1]octane.

The term "ester," as used herein, alone or in combination, refers to a carboxy group bridging two moieties linked at carbon atoms.

The term "ether," as used herein, alone or in combination, refers to an oxy group bridging two moieties linked at carbon atoms.

The term "halo," or "halogen," as used herein, alone or in combination, refers to fluorine, chlorine, bromine, or iodine.

The term "haloalkoxy," as used herein, alone or in combination, refers to a haloalkyl group attached to the parent molecular moiety through an oxygen atom.

The term "haloalkyl," as used herein, alone or in combination, refers to an alkyl group having the meaning as defined above wherein one or more hydrogens are replaced with a halogen. Specifically embraced are monohaloalkyl, dihaloalkyl and polyhaloalkyl groups. A monohaloalkyl group, for one example, may have an iodo, bromo, chloro or fluoro atom within the group. Dihalo and polyhaloalkyl groups may have two or more of the same halo atoms or a combination of different halo groups. Examples of haloalkyl groups include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Haloalkylene" refers to a haloalkyl group attached at two or more positions. Examples include fluoromethylene (—CFH—), difluoromethylene (—CF$_2$—), chloromethylene (—CHCl—) and the like.

The term "heteroalkyl," as used herein, alone or in combination, refers to a stable straight or branched chain, or cyclic hydrocarbon group, or combinations thereof, fully saturated or containing from 1 to 3 degrees of unsaturation, consisting of the stated number of carbon atoms and from one to three heteroatoms chosen from O, N, and S, and wherein the nitrogen and sulfur atoms may optionally be oxidized and the nitrogen heteroatom may optionally be quaternized. The heteroatom(s) O, N and S may be placed at any interior position of the heteroalkyl group. Up to two heteroatoms may be consecutive, such as, for example, —CH$_2$—NH—OCH$_3$.

The term "heteroaryl," as used herein, alone or in combination, refers to a 3 to 7 membered unsaturated heteromonocyclic ring, or a fused monocyclic, bicyclic, or tricyclic ring system in which at least one of the fused rings is aromatic, which contains at least one atom chosen from O, S, and N. In certain embodiments, said heteroaryl will comprise from 5 to 7 carbon atoms. The term also embraces fused polycyclic groups wherein heterocyclic rings are fused with aryl rings, wherein heteroaryl rings are fused with other heteroaryl rings, wherein heteroaryl rings are fused with heterocycloalkyl rings, or wherein heteroaryl rings are fused with cycloalkyl rings. Examples of heteroaryl groups include pyrrolyl, pyrrolinyl, imidazolyl, pyrazolyl, pyridyl, pyrimidinyl, pyrazinyl, pyridazinyl, triazolyl, pyranyl, furyl, thienyl, oxazolyl, isoxazolyl, oxadiazolyl, thiazolyl, thiadiazolyl, isothiazolyl, indolyl, isoindolyl, indolizinyl, benzimidazolyl, quinolyl, isoquinolyl, quinoxalinyl, quinazolinyl, indazolyl, benzotriazolyl, benzodioxolyl, benzopyranyl, benzoxazolyl, benzoxadiazolyl, benzothiazolyl, benzothiadiazolyl, benzofuryl, benzothienyl, chromonyl, coumarinyl, benzopyranyl, tetrahydroquinolinyl, tetrazolopyridazinyl, tetrahydroisoquinolinyl, thienopyridinyl, furopyridinyl, pyrrolopyridinyl and the like. Exemplary tricyclic heterocyclic groups include carbazolyl, benzidolyl, phenanthrolinyl, dibenzofuranyl, acridinyl, phenanthridinyl, xanthenyl and the like.

The terms "heterocycloalkyl" and, interchangeably, "heterocycle," as used herein, alone or in combination, each refer to a saturated, partially unsaturated, or fully unsaturated monocyclic, bicyclic, or tricyclic heterocyclic group containing at least one heteroatom as a ring member, wherein each said heteroatom may be independently chosen from nitrogen, oxygen, and sulfur. In certain embodiments, said heterocycloalkyl will comprise from 1 to 4 heteroatoms as ring members. In further embodiments, said heterocycloalkyl will comprise from 1 to 2 heteroatoms as ring members. In certain embodiments, said heterocycloalkyl will comprise from 3 to 8 ring members in each ring. In further embodiments, said heterocycloalkyl will comprise from 3 to 7 ring members in each ring. In yet further embodiments, said heterocycloalkyl will comprise from 5 to 6 ring members in each ring.

"Heterocycloalkyl" and "heterocycle" are intended to include sulfones, sulfoxides, N-oxides of tertiary nitrogen ring members, and carbocyclic fused and benzo fused ring systems; additionally, both terms also include systems where a heterocycle ring is fused to an aryl group, as defined herein, or an additional heterocycle group. Examples of heterocycle groups include aziridinyl, azetidinyl, 1,3-benzodioxolyl, dihydroisoindolyl, dihydroisoquinolinyl, dihydrocinnolinyl, dihydrobenzodioxinyl, dihydro[1,3]oxazolo[4,5-b]pyridinyl, benzothiazolyl, dihydroindolyl, dihy-dropyridinyl, 1,3-dioxanyl, 1,4-dioxanyl, 1,3-dioxolanyl, isoindolinyl, morpholinyl, piperazinyl, pyrrolidinyl, tetrahydropyridinyl, piperidinyl, thiomorpholinyl, and the like. The heterocycle groups may be optionally substituted unless specifically prohibited.

The term "hydrazinyl" as used herein, alone or in combination, refers to two amino groups joined by a single bond, i.e., —N—N—.

The term "hydroxy," as used herein, alone or in combination, refers to —OH.

The term "hydroxyalkyl," as used herein, alone or in combination, refers to a hydroxy group attached to the parent molecular moiety through an alkyl group.

The term "imino," as used herein, alone or in combination, refers to =N—.

The term "iminohydroxy," as used herein, alone or in combination, refers to =N(OH) and =N—O—.

The phrase "in the main chain" refers to the longest contiguous or adjacent chain of carbon atoms starting at the point of attachment of a group to the compounds of any one of the formulas disclosed herein.

The term "isocyanato" refers to a —NCO group.

The term "isothiocyanato" refers to a —NCS group.

The phrase "linear chain of atoms" refers to the longest straight chain of atoms independently selected from carbon, nitrogen, oxygen and sulfur.

The term "lower," as used herein, alone or in a combination, where not otherwise specifically defined, means containing from 1 to and including 6 carbon atoms.

The term "lower aryl," as used herein, alone or in combination, means phenyl or naphthyl, which may be optionally substituted as provided.

The term "lower heteroalkyl," as used herein, alone or in combination, refers to a stable straight or branched chain, or cyclic hydrocarbon group, or combinations thereof, fully saturated or containing from 1 to 3 degrees of unsaturation, consisting of one to six atoms in which one to three may be heteroatoms chosen from O, N, and S, and the remaining atoms are carbon. The nitrogen and sulfur atoms may optionally be oxidized and the nitrogen heteroatom may optionally be quaternized. The heteroatom(s) O, N and S may be placed at any interior or terminal position of the heteroalkyl group. Up to two heteroatoms may be consecutive, such as, for example, —CH$_2$—NH—OCH$_3$.

The term "lower heteroaryl," as used herein, alone or in combination, means either 1) monocyclic heteroaryl comprising five or six ring members, of which between one and four said members may be heteroatoms chosen from O, S, and N, or 2) bicyclic heteroaryl, wherein each of the fused rings comprises five or six ring members, comprising between them one to four heteroatoms chosen from O, S, and N.

The term "lower cycloalkyl," as used herein, alone or in combination, means a monocyclic cycloalkyl having between three and six ring members. Lower cycloalkyls may be unsaturated. Examples of lower cycloalkyl include cyclopropyl, cyclobutyl, cyclopentyl, and cyclohexyl.

The term "lower heterocycloalkyl," as used herein, alone or in combination, means a monocyclic heterocycloalkyl having between three and six ring members, of which between one and four may be heteroatoms chosen from O, S, and N. Examples of lower heterocycloalkyls include pyrrolidinyl, imidazolidinyl, pyrazolidinyl, piperidinyl, piperazinyl, and morpholinyl. Lower heterocycloalkyls may be unsaturated.

The term "lower amino," as used herein, alone or in combination, refers to —NRR', wherein R and R' are independently chosen from hydrogen, lower alkyl, and lower heteroalkyl, any of which may be optionally substituted. Additionally, the R and R' of a lower amino group may combine to form a five- or six-membered heterocycloalkyl, either of which may be optionally substituted.

The term "mercaptyl" as used herein, alone or in combination, refers to an RS— group, where R is as defined herein.

The term "nitro," as used herein, alone or in combination, refers to —NO$_2$.

The terms "oxy" or "oxa," as used herein, alone or in combination, refer to —O—.

The term "oxo," as used herein, alone or in combination, refers to =O.

The term "perhaloalkoxy" refers to an alkoxy group where all of the hydrogen atoms are replaced by halogen atoms.

The term "perhaloalkyl" as used herein, alone or in combination, refers to an alkyl group where all of the hydrogen atoms are replaced by halogen atoms.

The terms "sulfonate," "sulfonic acid," and "sulfonic," as used herein, alone or in combination, refer to the —SO$_3$H group and its anion as the sulfonic acid is used in salt formation.

The term "sulfanyl," as used herein, alone or in combination, refers to —S—.

The term "sulfinyl," as used herein, alone or in combination, refers to —S(O)—.

The term "sulfonyl," as used herein, alone or in combination, refers to —S(O)$_2$—.

The term "N-sulfonamido" refers to a RS(=O)$_2$NR'— group with R and R' as defined herein.

The term "S-sulfonamido" refers to a —S(=O)$_2$NRR', group, with R and R' as defined herein.

The terms "thia" and "thio," as used herein, alone or in combination, refer to a —S— group or an ether wherein the oxygen is replaced with sulfur. The oxidized derivatives of the thio group, namely sulfinyl and sulfonyl, are included in the definition of thia and thio.

The term "thiol," as used herein, alone or in combination, refers to an —SH group.

The term "thiocarbonyl," as used herein, when alone includes thioformyl —C(S)H and in combination is a —C(S)— group.

The term "N-thiocarbamyl" refers to an ROC(S)NR'— group, with R and R' as defined herein.

The term "O-thiocarbamyl" refers to a —OC(S)NRR' group with R and R' as defined herein.

The term "thiocyanato" refers to a —CNS group.

Any definition herein may be used in combination with any other definition to describe a composite structural group. By convention, the trailing element of any such definition is that which attaches to the parent moiety. For example, the composite group alkylamido would represent an alkyl group attached to the parent molecule through an amido group, and the term alkoxyalkyl would represent an alkoxy group attached to the parent molecule through an alkyl group.

When a group is defined to be "null," what is meant is that said group is absent.

The term "optionally substituted" means the anteceding group may be substituted or unsubstituted. When substituted, the substituents of an "optionally substituted" group may include, without limitation, one or more substituents independently selected from the following groups or a particular designated set of groups, alone or in combination: lower alkyl, lower alkenyl, lower alkynyl, lower alkanoyl, lower heteroalkyl, lower heterocycloalkyl, lower haloalkyl, lower haloalkenyl, lower haloalkynyl, lower perhaloalkyl, lower perhaloalkoxy, lower cycloalkyl, phenyl, aryl, aryloxy, lower alkoxy, lower haloalkoxy, oxo, lower acyloxy, carbonyl, carboxyl, lower alkylcarbonyl, lower carboxyester, lower carboxamido, cyano, hydrogen, halogen, hydroxy, amino, lower alkylamino, arylamino, amido, nitro, thiol, lower alkylthio, lower haloalkylthio, lower perhaloalkylthio, arylthio, sulfonate, sulfonic acid, trisubstituted silyl, $N_3$, SH, $SCH_3$, $C(O)CH_3$, $CO_2CH_3$, $CO_2H$, pyridinyl, thiophene, furanyl, lower carbamate, and lower urea. Two substituents may be joined together to form a fused five-, six-, or seven-membered carbocyclic or heterocyclic ring consisting of zero to three heteroatoms, for example forming methylenedioxy or ethylenedioxy. An optionally substituted group may be unsubstituted (e.g., $—CH_2CH_3$), fully substituted (e.g., $—CF_2CF_3$), monosubstituted (e.g., $—CH_2CH_2F$) or substituted at a level anywhere in-between fully substituted and monosubstituted (e.g., $—CH_2CF_3$). Where substituents are recited without qualification as to substitution, both substituted and unsubstituted forms are encompassed. Where a substituent is qualified as "substituted," the substituted form is specifically intended. Additionally, different sets of optional substituents to a particular moiety may be defined as needed; in these cases, the optional substitution will be as defined, often immediately following the phrase, "optionally substituted with."

The term R or the term R', appearing by itself and without a number designation, unless otherwise defined, refers to a moiety chosen from hydrogen, alkyl, cycloalkyl, heteroalkyl, aryl, heteroaryl and heterocycloalkyl, any of which may be optionally substituted. Such R and R' groups should be understood to be optionally substituted as defined herein. Whether an R group has a number designation or not, every R group, including R, R' and R'' where n=(1, 2, 3, . . . n), every substituent, and every term should be understood to be independent of every other in terms of selection from a group. Should any variable, substituent, or term (e.g. aryl, heterocycle, R, etc.) occur more than one time in a formula or generic structure, its definition at each occurrence is independent of the definition at every other occurrence. Those of skill in the art will further recognize that certain groups may be attached to a parent molecule or may occupy a position in a chain of elements from either end as written. Thus, by way of example only, an unsymmetrical group such as —C(O)N(R)— may be attached to the parent moiety at either the carbon or the nitrogen.

Asymmetric centers exist in the compounds disclosed herein. These centers are designated by the symbols "R" or "S," depending on the configuration of substituents around the chiral carbon atom. It should be understood that the invention encompasses all stereochemical isomeric forms, including diastereomeric, enantiomeric, and epimeric forms, as well as d-isomers and l-isomers, and mixtures thereof. Individual stereoisomers of compounds can be prepared synthetically from commercially available starting materials which contain chiral centers or by preparation of mixtures of enantiomeric products followed by separation such as conversion to a mixture of diastereomers followed by separation or recrystallization, chromatographic techniques, direct separation of enantiomers on chiral chromatographic columns, or any other appropriate method known in the art. Starting compounds of particular stereochemistry are either commercially available or can be made and resolved by techniques known in the art. Additionally, the compounds disclosed herein may exist as geometric isomers. The present invention includes all cis, trans, syn, anti, entgegen (E), and zusammen (Z) isomers as well as the appropriate mixtures thereof. Additionally, compounds may exist as tautomers; all tautomeric isomers are provided by this invention. Additionally, the compounds disclosed herein can exist in unsolvated as well as solvated forms with pharmaceutically acceptable solvents such as water, ethanol, and the like. In general, the solvated forms are considered equivalent to the unsolvated forms.

The term "bond" refers to a covalent linkage between two atoms, or two moieties when the atoms joined by the bond are considered to be part of larger substructure. A bond may be single, double, or triple unless otherwise specified. A dashed line between two atoms in a drawing of a molecule indicates that an additional bond may be present or absent at that position.

The term "disease" as used herein is intended to be generally synonymous, and is used interchangeably with, the terms "disorder" and "condition" (as in medical condition), in that all reflect an abnormal condition of the human or animal body or of one of its parts that impairs normal functioning, is typically manifested by distinguishing signs and symptoms, and causes the human or animal to have a reduced duration or quality of life.

The term "combination therapy" means the administration of two or more therapeutic agents to treat a therapeutic condition or disorder described in the present disclosure. Such administration encompasses co-administration of these therapeutic agents in a substantially simultaneous manner, such as in a single capsule having a fixed ratio of active ingredients or in multiple, separate capsules for each active ingredient. In addition, such administration also encompasses use of each type of therapeutic agent in a sequential manner. In either case, the treatment regimen will provide beneficial effects of the drug combination in treating the conditions or disorders described herein.

The term "inhibition" (and by extension, "inhibitor") as used herein encompasses all forms of functional protein (enzyme, kinase, receptor, channel, etc., for example) inhibition, including neutral antagonism, inverse agonism, competitive inhibition, and non-competitive inhibition (such as allosteric inhibition). Inhibition may be phrased in terms of an $IC_{50}$, defined below. Compounds disclosed herein may be $H_4R$ allosteric antagonists that are non competitive with histamine. Additionally, compounds disclosed herein may be agonists in one species and antagonists in another. Methods are known in the art, and are disclosed herein and can be adapted by those of skill in the art, to ascertain whether a compound is, for example, a suitable $H_4R$ antagonist in a species of interest.

In certain embodiments, "$H_1R$ inhibitor" is used herein to refer to a compound that exhibits an $IC_{50}$ with respect to the histamine type-1 receptor of no more than about 100 μM and more typically not more than about 50 μM, as measured in the in vitro histamine receptor cell-based assays described generally hereinbelow.

Similarly, "$H_3R$ inhibitor" is used herein to refer to a compound that exhibits an $IC_{50}$ with respect to the histamine type-3 receptor of no more than about 100 μM and more typically not more than about 50 μM, as measured in the in vitro histamine receptor cell-based assays described generally hereinbelow.

Also similarly, "$H_4R$ inhibitor" is used herein to refer to a compound that exhibits an $IC_{50}$ with respect to the histamine type-4 receptor of no more than about 100 μM and more typically not more than about 50 μM, as measured in the in vitro histamine receptor cell-based assays described generally hereinbelow.

A "$H_1/H_4$ inhibitor" is used herein to refer to a compound that exhibits an $IC_{50}$ with respect to both the histamine type-1 receptor and the histamine type-4 receptor of no more than about 100 μM and more typically not more than about 50 μM, as measured in the in vitro histamine receptor cell-based assays described generally hereinbelow; the amount of inhibition need not be equivalent at each receptor, but should not be negligible.

In certain embodiments, such as, for example, in the case of an in vitro ligand-binding assay protocol, "$IC_{50}$" is that concentration of compound which is required to displace a natural ligand or reference standard to a half-maximal level. In other embodiments, such as, for example, in the case of certain cellular or in vivo protocols which have a functional readout, "$IC_{50}$" is that concentration of compound which reduces the activity of a functional protein (e.g., $H_1R$ and/or $H_4R$) to a half-maximal level. In either of these scenarios, the term "$EC_{50}$" may also be used. In vitro or in vivo, "$EC_{50}$" refers to the concentration of a compound required to achieve half of the maximal effect in an assay or protocol, typically as compared to a reference standard.

Certain compounds disclosed herein have been discovered to exhibit inhibitory activity against $H_4R$. In certain embodiments, compounds will exhibit an $IC_{50}$ with respect to $H_4R$ of no more than about 10 μM; in further embodiments, compounds will exhibit an $IC_{50}$ with respect to $H_4R$ of no more than about 5 μM; in yet further embodiments, compounds will exhibit an $IC_{50}$ with respect to $H_4R$ of not more than about 1 μM; in yet further embodiments, compounds will exhibit an $IC_{50}$ with respect to $H_4R$ of not more than about 200 nM, as measured in an $H_4R$ assay such as that described herein.

The phrase "therapeutically effective" is intended to qualify the amount of active ingredients used in the treatment of a disease or disorder. This amount will achieve the goal of reducing or eliminating the said disease or disorder.

The term "therapeutically acceptable" refers to those compounds (or salts, prodrugs, tautomers, zwitterionic forms, etc.) which are suitable for use in contact with the tissues of patients without undue toxicity, irritation, and allergic response, are commensurate with a reasonable benefit/risk ratio, and are effective for their intended use.

As used herein, reference to "treatment" of a patient is intended to include prophylaxis. The term "patient" means all mammals including humans. Examples of patients include humans, cows, dogs, cats, goats, sheep, pigs, and rabbits. Preferably, the patient is a human.

The term "prodrug" refers to a compound that is made more active in vivo. Certain compounds disclosed herein may also exist as prodrugs, as described in *Hydrolysis in Drug and Prodrug Metabolism: Chemistry, Biochemistry, and Enzymology* (Testa, Bernard and Mayer, Joachim M. Wiley-VHCA, Zurich, Switzerland 2003). Prodrugs of the compounds described herein are structurally modified forms of the compound that readily undergo chemical changes under physiological conditions to provide the compound. Additionally, prodrugs can be converted to the compound by chemical or biochemical methods in an ex vivo environment. For example, prodrugs can be slowly converted to a compound when placed in a transdermal patch reservoir with a suitable enzyme or chemical reagent. Prodrugs are often useful because, in some situations, they may be easier to administer than the compound, or parent drug. They may, for instance, be bioavailable by oral administration whereas the parent drug is not. The prodrug may also have improved solubility in pharmaceutical compositions over the parent drug. A wide variety of prodrug derivatives are known in the art, such as those that rely on hydrolytic cleavage or oxidative activation of the prodrug. An example, without limitation, of a prodrug would be a compound which is administered as an ester (the "prodrug"), but then is metabolically hydrolyzed to the carboxylic acid, the active entity. Additional examples include peptidyl derivatives of a compound.

The compounds disclosed herein can exist as therapeutically acceptable salts. The present invention includes compounds listed above in the form of salts, including acid addition salts. Suitable salts include those formed with both organic and inorganic acids. Such acid addition salts will normally be pharmaceutically acceptable. However, salts of non-pharmaceutically acceptable salts may be of utility in the preparation and purification of the compound in question. Basic addition salts may also be formed and be pharmaceutically acceptable. For a more complete discussion of the preparation and selection of salts, refer to *Pharmaceutical Salts: Properties, Selection, and Use* (Stahl, P. Heinrich. Wiley-VCHA, Zurich, Switzerland, 2002).

The term "therapeutically acceptable salt," as used herein, represents salts or zwitterionic forms of the compounds disclosed herein which are water or oil-soluble or dispersible and therapeutically acceptable as defined herein. The salts can be prepared during the final isolation and purification of the compounds or separately by reacting the appropriate compound in the form of the free base with a suitable acid. Representative acid addition salts include acetate, adipate, alginate, L-ascorbate, aspartate, benzoate, benzenesulfonate (besylate), bisulfate, butyrate, camphorate, camphorsulfonate, citrate, digluconate, formate, fumarate, gentisate, glutarate, glycerophosphate, glycolate, hemisulfate, heptanoate, hexanoate, hippurate, hydrochloride, hydrobromide, hydroiodide, 2-hydroxyethansulfonate (isethionate), lactate, maleate, malonate, DL-mandelate, mesitylenesulfonate, methanesulfonate, naphthylenesulfonate, nicotinate, 2-naphthalenesulfonate, oxalate, pamoate, pectinate, persulfate, 3-phenylproprionate, phosphonate, picrate, pivalate, propionate, pyroglutamate, succinate, sulfonate, tartrate, L-tartrate, trichloroacetate, trifluoroacetate, phosphate, glutamate, bicarbonate, para-toluenesulfonate (p-tosylate), and undecanoate. Also, basic groups in the compounds disclosed herein can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. Examples of acids which can be employed to form therapeutically acceptable addition salts include inorganic acids such as hydrochloric, hydrobromic, sulfuric, and phosphoric, and organic acids such as oxalic, maleic, succinic, and citric. Salts can also be formed by coordination of the compounds with an alkali metal or alkaline earth ion. Hence, the present invention contemplates sodium, potassium, magnesium, and calcium salts of the compounds disclosed herein, and the like.

Basic addition salts can be prepared during the final isolation and purification of the compounds by reacting a carboxy group with a suitable base such as the hydroxide, carbonate, or bicarbonate of a metal cation or with ammonia or an organic primary, secondary, or tertiary amine. The cations of therapeutically acceptable salts include lithium, sodium, potassium, calcium, magnesium, and aluminum, as well as nontoxic quaternary amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine, and N,N-dibenzylethylenediamine. Other representative organic amines useful for the formation of base addition salts include ethylenediamine, ethanolamine, diethanolamine, piperidine, and piperazine.

While it may be possible for the compounds of the subject invention to be administered as the raw chemical, it is also possible to present them as a pharmaceutical formulation. Accordingly, provided herein are pharmaceutical formulations which comprise one or more of certain compounds disclosed herein, or one or more pharmaceutically acceptable salts, esters, prodrugs, amides, or solvates thereof, together with one or more pharmaceutically acceptable carriers thereof and optionally one or more other therapeutic ingredients. The carrier(s) must be "acceptable" in the sense of being compatible with the other ingredients of the formulation and not deleterious to the recipient thereof. Proper formulation is dependent upon the route of administration chosen. Any of the well-known techniques, carriers, and excipients may be used as suitable and as understood in the art; e.g., in Remington's Pharmaceutical Sciences. The pharmaceutical compositions disclosed herein may be manufactured in any manner known in the art, e.g., by means of conventional mixing, dissolving, granulating, dragee-making, levigating, emulsifying, encapsulating, entrapping or compression processes.

The formulations include those suitable for oral, parenteral (including subcutaneous, intradermal, intramuscular, intravenous, intraarticular, and intramedullary), intraperitoneal, transmucosal, transdermal, rectal and topical (including dermal, buccal, sublingual, ocular, intranasal, and intraocular) administration although the most suitable route may depend upon for example the condition and disorder of the recipient. The formulations may conveniently be presented in unit dosage form and may be prepared by any of the methods well known in the art of pharmacy. Typically, these methods include the step of bringing into association a compound of the subject invention or a pharmaceutically acceptable salt, ester, amide, prodrug or solvate thereof ("active ingredient") with the carrier which constitutes one or more accessory ingredients. In general, the formulations are prepared by uniformly and intimately bringing into association the active ingredient with liquid carriers or finely divided solid carriers or both and then, if necessary, shaping the product into the desired formulation.

Formulations of the compounds disclosed herein suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

Pharmaceutical preparations which can be used orally include tablets, push-fit capsules made of gelatin, as well as soft, sealed capsules made of gelatin and a plasticizer, such as glycerol or sorbitol. Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface active or dispersing agents. Molded tablets may be made by molding in a suitable machine a mixture of the powdered compound moistened with an inert liquid diluent. The tablets may optionally be coated or scored and may be formulated so as to provide slow or controlled release of the active ingredient therein. All formulations for oral administration should be in dosages suitable for such administration. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Examples of fillers or diluents for use in oral pharmaceutical formulations such as capsules and tablets include, without limitation, lactose, mannitol, xylitol, dextrose, sucrose, sorbitol, compressible sugar, microcrystalline cellulose (MCC), powdered cellulose, cornstarch, pregelatinized starch, dextrates, dextran, dextrin, dextrose, maltodextrin, calcium carbonate, dibasic calcium phosphate, tribasic calcium phosphate, calcium sulfate, magnesium carbonate, magnesium oxide, poloxamers such as polyethylene oxide, and hydroxypropyl methyl cellulose. Fillers may have complexed solvent molecules, such as in the case where the lactose used is lactose monohydrate. Fillers may also be proprietary, such in the case of the filler PROSOLV® (available from JRS Pharma). PROSOLV is a proprietary, optionally high-density, silicified microcrystalline cellulose composed of 98% microcrystalline cellulose and 2% colloidal silicon dioxide. Silicification of the microcrystalline cellulose is achieved by a patented process, resulting in an intimate association between the colloidal silicon dioxide and microcrystalline cellulose. ProSolv comes in different grades based on particle size, and is a white or almost white, fine or granular powder, practically insoluble in water, acetone, ethanol, toluene and dilute acids and in a 50 g/l solution of sodium hydroxide.

Examples of disintegrants for use in oral pharmaceutical formulations such as capsules and tablets include, without limitation, sodium starch glycolate, sodium carboxymethyl cellulose, calcium carboxymethyl cellulose, croscarmellose sodium, povidone, crospovidone (polyvinylpolypyrrolidone), methyl cellulose, microcrystalline cellulose, powdered cellulose, low-substituted hydroxy propyl cellulose, starch, pregelatinized starch, and sodium alginate.

Additionally, glidants and lubricants may be used in oral pharmaceutical formulations to ensure an even blend of excipients upon mixing. Examples of lubricants include, without limitation, calcium stearate, glyceryl monostearate, glyceryl palmitostearate, hydrogenated vegetable oil, light mineral oil, magnesium stearate, mineral oil, polyethylene glycol, sodium benzoate, sodium lauryl sulfate, sodium stearyl fumarate, stearic acid, talc, and zinc stearate. Examples of glidants include, without limitation, silicon dioxide ($SiO_2$), talc cornstarch, and poloxamers. Poloxamers (or LUTROL®, available from the BASF Corporation) are A-B-A block copolymers in which the A segment is a hydrophilic polyethylene glycol homopolymer and the B segment is hydrophobic polypropylene glycol homopolymer.

Examples of tablet binders include, without limitation, acacia, alginic acid, carbomer, carboxymethyl cellulose sodium, dextrin, ethylcellulose, gelatin, guar gum, hydrogenated vegetable oil, hydroxyethyl cellulose, hydroxypropyl cellulose, hydroxypropylmethyl cellulose, copolyvidone, methyl cellulose, liquid glucose, maltodextrin, polymethacrylates, povidone, pregelatinized starch, sodium alginate, starch, sucrose, tragacanth, and zein.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. The formulations may be presented in unit-dose or multi-dose containers, for example sealed ampoules and vials, and may be stored in powder form or in a freeze-dried (lyophilized) condition requiring only the addition of the sterile liquid carrier, for example, saline or sterile pyrogen-free water, immediately prior to use. Extemporaneous injection solutions and suspensions may be prepared from sterile powders, granules and tablets of the kind previously described.

Formulations for parenteral administration include aqueous and non-aqueous (oily) sterile injection solutions of the active compounds which may contain antioxidants, buffers, bacteriostats and solutes which render the formulation isotonic with the blood of the intended recipient; and aqueous and non-aqueous sterile suspensions which may include suspending agents and thickening agents. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example, as an emulsion in an acceptable oil) or ion exchange resins, or as sparingly soluble derivatives, for example, as a sparingly soluble salt.

For buccal or sublingual administration, the compositions may take the form of tablets, lozenges, pastilles, or gels formulated in conventional manner. Such compositions may comprise the active ingredient in a flavored basis such as sucrose and acacia or tragacanth.

The compounds may also be formulated in rectal compositions such as suppositories or retention enemas, e.g., containing conventional suppository bases such as cocoa butter, polyethylene glycol, or other glycerides.

Certain compounds disclosed herein may be administered topically, that is by non-systemic administration. This includes the application of a compound disclosed herein externally to the epidermis or the buccal cavity and the instillation of such a compound into the ear, eye and nose, such that the compound does not significantly enter the blood stream. In contrast, systemic administration refers to oral, intravenous, intraperitoneal and intramuscular administration.

Formulations suitable for topical administration include liquid or semi-liquid preparations suitable for penetration through the skin to the site of inflammation such as gels, liniments, lotions, creams, ointments or pastes, and drops suitable for administration to the eye, ear or nose. The active ingredient for topical administration may comprise, for example, from 0.001% to 10% w/w (by weight) of the formulation. In certain embodiments, the active ingredient may comprise as much as 10% w/w. In other embodiments, it may comprise less than 5% w/w. In certain embodiments, the active ingredient may comprise from 2% w/w to 5% w/w. In other embodiments, it may comprise from 0.1% to 2% w/w of the formulation.

Topical ophthalmic, otic, and nasal formulations of the present invention may comprise excipients in addition to the active ingredient. Excipients commonly used in such formulations include, but are not limited to, tonicity agents, preservatives, chelating agents, buffering agents, and surfactants. Other excipients comprise solubilizing agents, stabilizing agents, comfort-enhancing agents, polymers, emollients, pH-adjusting agents and/or lubricants. Any of a variety of excipients may be used in formulations of the present invention including water, mixtures of water and water-miscible solvents, such as C1-C7-alkanols, vegetable oils or mineral oils comprising from 0.5 to 5% non-toxic water-soluble polymers, natural products, such as alginates, pectins, tragacanth, karaya gum, guar gum, xanthan gum, carrageenin, agar and acacia, starch derivatives, such as starch acetate and hydroxypropyl starch, and also other synthetic products such as polyvinyl alcohol, polyvinylpyrrolidone, polyvinyl methyl ether, polyethylene oxide, preferably cross-linked polyacrylic acid and mixtures of those products. The concentration of the excipient is, typically, from 1 to 100,000 times the concentration of the active ingredient. In preferred embodiments, the excipients to be included in the formulations are typically selected on the basis of their inertness towards the active ingredient component of the formulations.

Relative to ophthalmic, otic, and nasal formulations, suitable tonicity-adjusting agents include, but are not limited to, mannitol, dextrose, sodium chloride, glycerin, sorbitol and the like. Suitable buffering agents include, but are not limited to, phosphates, citrates, borates, acetates and the like. Suitable surfactants include, but are not limited to, ionic and nonionic surfactants (though nonionic surfactants are preferred), polysorbate 80, RLM 100, POE 20 cetylstearyl ethers such as Procol® CS20 and poloxamers such as Pluronic® F68. Formulations may contain substances which increase the viscosity of the solution or suspension, such as sodium carboxymethyl cellulose, hypromellose, micro crystalline cellulose, sorbitol, or dextran. Optionally, the formulation may also contain suitable stabilizers or agents which increase the solubility of the compounds to allow for the preparation of highly concentrated solutions, including but not limited to ethanol, benzyl alcohol, polyethylene glycol, phenylethyl alcohol and glycerin.

The formulations set forth herein may comprise one or more preservatives. Examples of such preservatives include benzalkonium chloride, p-hydroxybenzoic acid ester, sodium perborate, sodium chlorite, alcohols such as chlorobutanol, benzyl alcohol or phenyl ethanol, guanidine derivatives such as polyhexamethylene biguanide, sodium perborate, polyquarternium-1, amino alcohols such as AMP-95, or sorbic acid. In certain embodiments, the formulation may be self-preserved so that no preservation agent is required.

For ophulmic, otic, or nasal administration, the formulation may be a solution, a suspension, or a gel. In preferred aspects, the formulations are for topical application to the eye, or ear are in aqueous solution or suspension in the form of drops. Formulations for topical application to the nose in aqueous solution or suspension are in the form of drops, spray or aerosol. The term "aqueous" typically denotes an aqueous formulation wherein the formulation is >50%, more preferably >75% and in particular >90% by weight water. These drops may be delivered from a single dose ampoule which may preferably be sterile and thus render bacteriostatic components of the formulation unnecessary. Alternatively, the drops may be delivered from a multi-dose bottle which may preferably comprise a device which extracts any preservative from the formulation as it is delivered, such devices being known in the art. Solution and suspension formulations may be nasally administered using a nebulizer. Intranasal delivery as a solution, suspension or dry powder may also facilitated by propellant-based aerosol systems, which include but are not limited to hydrofluoroalkane-based propellants. Alternatively the active pharmaceutical ingredient may be delivered in the form of a dry powder.

For ophthalmic disorders, components of the invention may be delivered to the eye as a concentrated gel or a similar vehicle, or as dissolvable inserts that are placed beneath the eyelids.

The formulations of the present invention that are adapted for topical administration to the eye are preferably isotonic, or slightly hypotonic in order to combat any hypertonicity of tears caused by evaporation and/or disease. This may require a tonicity agent to bring the osmolality of the formulation to a level at or near 210-320 milliosmoles per kilogram (mOsm/kg). The formulations of the present invention generally have an osmolality in the range of 220-320 mOsm/kg, and preferably have an osmolality in the range of 235-300 mOsm/kg. The ophthalmic formulations will generally be formulated as sterile aqueous solutions.

In certain ophthalmic embodiments, the compositions of the present invention are formulated with one or more tear substitutes. A variety of tear substitutes are known in the art and include, but are not limited to: monomeric polyols, such as, glycerol, propylene glycol, and ethylene glycol; polymeric polyols such as polyethylene glycol; cellulose esters such hydroxypropylmethyl cellulose, carboxy methylcellulose sodium and hydroxy propylcellulose; dextrans such as dextran 70; vinyl polymers, such as polyvinyl alcohol; and carbomers, such as carbomer 934P, carbomer 941, carbomer 940 and carbomer 974P. Certain formulations of the present invention may be used with contact lenses or other ophthalmic products.

Preferred formulations are prepared using a buffering system that maintains the formulation at a pH of about 4.5 to a pH of about 8. A most preferred formulation pH is from 5.5 to 7.5.

In particular embodiments, a formulation of the present invention is administered once a day. However, the formulations may also be formulated for administration at any frequency of administration, including once a week, once every 5 days, once every 3 days, once every 2 days, twice a day, three times a day, four times a day, five times a day, six times a day, eight times a day, every hour, or any greater frequency. Such dosing frequency is also maintained for a varying duration of time depending on the therapeutic regimen. The duration of a particular therapeutic regimen may vary from one-time dosing to a regimen that extends for months or years. The formulations are administered at varying dosages, but typical dosages are one to two drops at each administration, or a comparable amount of a gel or other formulation. One of ordinary skill in the art would be familiar with determining a therapeutic regimen for a specific indication.

Gels for topical or transdermal administration may comprise, generally, a mixture of volatile solvents, nonvolatile solvents, and water. In certain embodiments, the volatile solvent component of the buffered solvent system may include lower (C1-C6) alkyl alcohols, lower alkyl glycols and lower glycol polymers. In further embodiments, the volatile solvent is ethanol. The volatile solvent component is thought to act as a penetration enhancer, while also producing a cooling effect on the skin as it evaporates. The nonvolatile solvent portion of the buffered solvent system is selected from lower alkylene glycols and lower glycol polymers. In certain embodiments, propylene glycol is used. The nonvolatile solvent slows the evaporation of the volatile solvent and reduces the vapor pressure of the buffered solvent system. The amount of this nonvolatile solvent component, as with the volatile solvent, is determined by the pharmaceutical compound or drug being used. When too little of the nonvolatile solvent is in the system, the pharmaceutical compound may crystallize due to evaporation of volatile solvent, while an excess may result in a lack of bioavailability due to poor release of drug from solvent mixture. The buffer component of the buffered solvent system may be selected from any buffer commonly used in the art; in certain embodiments, water is used. A common ratio of ingredients is about 20% of the nonvolatile solvent, about 40% of the volatile solvent, and about 40% water. There are several optional ingredients which can be added to the topical composition. These include, but are not limited to, chelators and gelling agents. Appropriate gelling agents can include, but are not limited to, semisynthetic cellulose derivatives (such as hydroxypropylmethylcellulose) and synthetic polymers, galactomannan polymers (such as guar and derivatives thereof) and cosmetic agents.

Lotions include those suitable for application to the skin or eye. An eye lotion may comprise a sterile aqueous solution optionally containing a bactericide and may be prepared by methods similar to those for the preparation of drops. Lotions or liniments for application to the skin may also include an agent to hasten drying and to cool the skin, such as an alcohol or acetone, and/or a moisturizer such as glycerol or an oil such as castor oil or arachis oil.

Creams, ointments or pastes are semi-solid formulations of the active ingredient for external application. They may be made by mixing the active ingredient in finely-divided or powdered form, alone or in solution or suspension in an aqueous or non-aqueous fluid, with the aid of suitable machinery, with a greasy or non-greasy base. The base may comprise hydrocarbons such as hard, soft or liquid paraffin, glycerol, beeswax, a metallic soap; a mucilage; an oil of natural origin such as almond, corn, arachis, castor or olive oil; wool fat or its derivatives or a fatty acid such as stearic or oleic acid together with an alcohol such as propylene glycol or a macrogel. The formulation may incorporate any suitable surface active agent such as an anionic, cationic or non-ionic surfactant such as a sorbitan ester or a polyoxyethylene derivative thereof. Suspending agents such as natural gums, cellulose derivatives or inorganic materials such as silicaceous silicas, and other ingredients such as lanolin, may also be included.

Drops or sprays may comprise sterile aqueous or oily solutions or suspensions and may be prepared by dissolving the active ingredient in a suitable aqueous solution of a bactericidal and/or fungicidal agent and/or any other suitable preservative, and, in certain embodiments, including a surface active agent. The resulting solution may then be clarified by filtration, transferred to a suitable container which is then sealed and sterilized by autoclaving or maintaining at 98-100° C. for half an hour. Alternatively, the solution may be sterilized by filtration and transferred to the container by an aseptic technique. Examples of bactericidal and fungicidal agents suitable for inclusion in the drops are phenylmercuric nitrate or acetate (0.002%), benzalkonium chloride (0.01%) and chlorhexidine acetate (0.01%). Suitable solvents for the preparation of an oily solution include glycerol, diluted alcohol and propylene glycol.

Formulations for topical administration in the mouth, for example buccally or sublingually, include lozenges comprising the active ingredient in a flavored basis such as sucrose and acacia or tragacanth, and pastilles comprising the active ingredient in a basis such as gelatin and glycerin or sucrose and acacia.

For administration by inhalation, compounds may be conveniently delivered from an insufflator, nebulizer pressurized packs or other convenient means of delivering an aerosol spray. Pressurized packs may comprise a suitable propellant such as hydrofluoroalkane, dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Alternatively, for administration by inhalation or insufflation, the compounds according to the invention may take the form of a dry powder composition, for example a powder mix of the compound and a suitable powder base such as lactose or starch. The powder composition may be presented in unit dosage form, in for example, capsules, cartridges, gelatin or blister packs from which the powder may be administered with the aid of an inhalator or insufflator.

Preferred unit dosage formulations are those containing an effective dose, as herein below recited, or an appropriate fraction thereof, of the active ingredient.

It should be understood that in addition to the ingredients particularly mentioned above, the formulations described above may include other agents conventional in the art having regard to the type of formulation in question, for example those suitable for oral or intranasal administration may include flavoring agents.

Compounds may be administered orally or via injection at a dose of from 0.1 to 500 mg/kg per day. The dose range for adult humans is generally from 5 mg to 2 g/day. Tablets or other forms of presentation provided in discrete units may conveniently contain an amount of one or more compounds which is effective at such dosage or as a multiple of the same, for instance, units containing 5 mg to 500 mg, usually around 10 mg to 200 mg.

The amount of active ingredient that may be combined with the carrier materials to produce a single dosage form will vary depending upon the host treated and the particular mode of administration.

The compounds can be administered in various modes, e.g. orally, topically, or by injection. The precise amount of compound administered to a patient will be the responsibility of the attendant physician. The specific dose level for any particular patient will depend upon a variety of factors including the activity of the specific compound employed, the age, body weight, general health, sex, diets, time of administration, route of administration, rate of excretion, drug combination, the precise disorder being treated, and the severity of the indication or condition being treated. Also, the route of administration may vary depending on the condition and its severity.

In certain instances, it may be appropriate to administer at least one of the compounds described herein (or a pharmaceutically acceptable salt, ester, or prodrug thereof) in combination with another therapeutic agent. By way of example only, if one of the side effects experienced by a patient upon receiving one of the compounds herein is hypertension, then it may be appropriate to administer an anti-hypertensive agent in combination with the initial therapeutic agent. Or, by way of example only, the therapeutic effectiveness of one of the compounds described herein may be enhanced by administration of an adjuvant (i.e., by itself the adjuvant may only have minimal therapeutic benefit, but in combination with another therapeutic agent, the overall therapeutic benefit to the patient is enhanced). Or, by way of example only, the benefit of experienced by a patient may be increased by administering one of the compounds described herein with another therapeutic agent (which also includes a therapeutic regimen) that also has therapeutic benefit. By way of example only, in a treatment for diabetes involving administration of one of the compounds described herein, increased therapeutic benefit may result by also providing the patient with another therapeutic agent for diabetes. In any case, regardless of the disease, disorder or condition being treated, the overall benefit experienced by the patient may simply be additive of the two therapeutic agents or the patient may experience a synergistic benefit.

Non-limiting examples of possible combination therapies include use of certain compounds of the invention with $H_1R$ antagonists, $H_3R$ antagonists and/or intranasal corticosteroids. Specific, non-limiting examples of possible combination therapies include use of certain compounds of the invention with $H_1R$ antagonists such as acrivastine, alcaftadine, antazoline, azelastine, bromazine, brompheniramine, cetirizine, chlorpheniramine, clemastine, desloratidine, diphenhydramine, diphenylpyraline, ebastine, emedastine, epinastine, fexofenadine, hydroxyzine, ketotifen, levocabastine, levocetirizine, loratidine, methdilazine, mizolastine, promethazine, olopatadine, and triprolidine, or intranasal corticosteroids such as fluticasone, budesonide, beclomethasone, mometasone, triamcinolone, and ciclesonide.

In any case, the multiple therapeutic agents (at least one of which is a compound disclosed herein) may be administered in any order or even simultaneously. If simultaneously, the multiple therapeutic agents may be provided in a single, unified form, or in multiple forms (by way of example only, either as a single pill or as two separate pills). One of the therapeutic agents may be given in multiple doses, or both may be given as multiple doses. If not simultaneous, the timing between the multiple doses may be any duration of time ranging from a few minutes to four weeks.

Thus, in another aspect, certain embodiments provide methods for treating $H_4R$-mediated disorders in a human or animal subject in need of such treatment comprising administering to said subject an amount of a compound disclosed herein effective to reduce or prevent said disorder in the subject, in combination with at least one additional agent for the treatment of said disorder that is known in the art. In a related aspect, certain embodiments provide therapeutic compositions comprising at least one compound disclosed herein in combination with one or more additional agents for the treatment of $H_4R$-mediated disorders.

Specific diseases to be treated by the compounds, compositions, and methods disclosed herein include inflammation and related diseases, including autoimmune diseases. The compounds are useful to treat arthritis, including but not limited to rheumatoid arthritis, spondyloarthropathies, gouty arthritis, osteoarthritis, systemic lupus erythematosus, juvenile arthritis, acute rheumatic arthritis, enteropathic arthritis, neuropathic arthritis, psoriatic arthritis, and pyogenic arthritis. The compounds are also useful in treating osteoporosis and other related bone disorders. These compounds can also be used to treat gastrointestinal conditions such as reflux esophagitis, diarrhea, inflammatory bowel disease, Crohn's disease, gastritis, irritable bowel syndrome and ulcerative colitis. The compounds may also be used in the treatment of upper respiratory inflammation, such as, but not limited to, seasonal allergic rhinitis, non-seasonal allergic rhinitis, acute non-allergic rhinitis, chronic non-allergic rhinitis, Sampter's triad, non-allergic rhinitis with eosinophilia syndrome, nasal polyposis, atrophic rhinitis, hypertrophic rhinitis, membranous rhinitis, vasomotor rhinitis, rhinosinusitis, chronic rhinopharyngitis, rhinorrhea, occupational rhinitis, hormonal rhinitis, drug-induced rhinitis, gustatory rhinitis, as well as pulmonary inflammation, such as that associated with viral infections and cystic fibrosis. In addition, compounds disclosed herein are also useful in organ transplant patients either alone or in combination with conventional immunomodulators.

Moreover, compounds disclosed herein may be used in the treatment of tendonitis, bursitis, skin-related conditions such as psoriasis, allergic dermatitis, atopic dermatitis and other variants of eczema, allergic contact dermatitis, irritant contact dermatitis, seborrhoeic eczema, nummular eczematous dermatitis, autosensitization dermatitis, Lichen Simplex Chronicus, dyshidrotic dermatitis, neurodermatitis, stasis dermatitis, generalized ordinary urticaria, acute allergic urticaria, chronic allergic urticaria, autoimmune urticaria, chronic idiopathic urticaria, drug-induced urticaria, cholinergic urticaria, chronic cold urticaria, dermatographic urticaria, solar urticaria, urticaria pigmentosa, mastocytosis, acute or chronic pruritis associated with skin-localized or systemic diseases and disorders, such as pancreatitis, hepatitis, burns, sunburn, and vitiligo.

Further, the compounds disclosed herein can be used to treat respiratory diseases, including therapeutic methods of use in medicine for preventing and treating a respiratory disease or condition including: asthmatic conditions including allergen-induced asthma, exercise-induced asthma, pollution-induced asthma, cold-induced asthma, and viral-induced-asthma; chronic obstructive pulmonary diseases including chronic bronchitis with normal airflow, chronic bronchitis with airway obstruction (chronic obstructive bronchitis), emphysema, asthmatic bronchitis, and bullous disease; and other pulmonary diseases involving inflammation including bronchioectasis cystic fibrosis, pigeon fancier's disease, farmer's lung, acute respiratory distress syndrome, pneumonia, aspiration or inhalation injury, fat embolism in the lung, acidosis inflammation of the lung, acute pulmonary edema, acute mountain sickness, acute pulmonary hypertension, persistent pulmonary hypertension of the newborn, perinatal aspiration syndrome, hyaline membrane disease, acute pulmonary thromboembolism, heparin-protamine reactions, sepsis, status asthamticus and hypoxia.

The compounds disclosed herein are also useful in treating tissue damage in such diseases as vascular diseases, periarteritis nodosa, thyroiditis, sclerodoma, rheumatic fever, type I diabetes, neuromuscular junction disease including myasthenia gravis, white matter disease including multiple sclerosis, sarcoidosis, nephritis, nephrotic syndrome, Behcet's syndrome, polymyositis, gingivitis, periodontis, hypersensitivity, and swelling occurring after injury.

The compounds disclosed herein can be used in the treatment of otic diseases and otic allergic disorders, including eustachian tube itching.

The compounds disclosed herein can be used in the treatment of ophthalmic diseases, such as ophthalmic allergic disorders, including allergic conjunctivitis, vernal conjunctivitis, vernal keratoconjunctivitis, and giant papillary conjunctivitis, dry eye, glaucoma, glaucomatous retinopathy, diabetic retinopathy, retinal ganglion degeneration, ocular ischemia, retinitis, retinopathies, uveitis, ocular photophobia, and of inflammation and pain associated with acute injury to the eye tissue. The compounds can also be used to treat post-operative inflammation or pain as from ophthalmic surgery such as cataract surgery and refractive surgery. In preferred embodiments, the compounds of the present invention are used to treat an allergic eye disease chosen from allergic conjunctivitis; vernal conjunctivitis; vernal keratoconjunctivitis; and giant papillary conjunctivitis.

Compounds disclosed herein are useful in treating patients with inflammatory pain such as reflex sympathetic dystrophy/causalgia (nerve injury), peripheral neuropathy (including diabetic neuropathy), and entrapment neuropathy (carpel tunnel syndrome). The compounds are also useful in the treatment of pain associated with acute herpes zoster (shingles), postherpetic neuralgia (PHN), and associated pain syndromes such as ocular pain. Pain indications include, but are not limited to, pain resulting from dermal injuries and pain-related disorders such as tactile allodynia and hyperalgesia. The pain may be somatogenic (either nociceptive or neuropathic), acute and/or chronic.

The present compounds may also be used in co-therapies, partially or completely, in place of other conventional anti-inflammatory therapies, such as together with steroids, NSAIDs, COX-2 selective inhibitors, 5-lipoxygenase inhibitors, $LTB_4$ antagonists and $LTA_4$ hydrolase inhibitors. The compounds disclosed herein may also be used to prevent tissue damage when therapeutically combined with antibacterial or antiviral agents.

Besides being useful for human treatment, certain compounds and formulations disclosed herein may also be useful for veterinary treatment of companion animals, exotic animals and farm animals, including mammals, rodents, and the like. More preferred animals include horses, dogs, and cats.

All references, patents or applications, U.S. or foreign, cited in the application are hereby incorporated by reference as if written herein in their entireties. Where any inconsistencies arise, material literally disclosed herein controls.

METHODS FOR PREPARING COMPOUNDS AND EXAMPLES

The following schemes can be used to practice the present invention. A person skilled in the art may adapt the Schemes to synthesis of compounds other than those they may specifically depict. The invention is further illustrated by the following examples, which may be made my methods known in the art and/or as shown below.

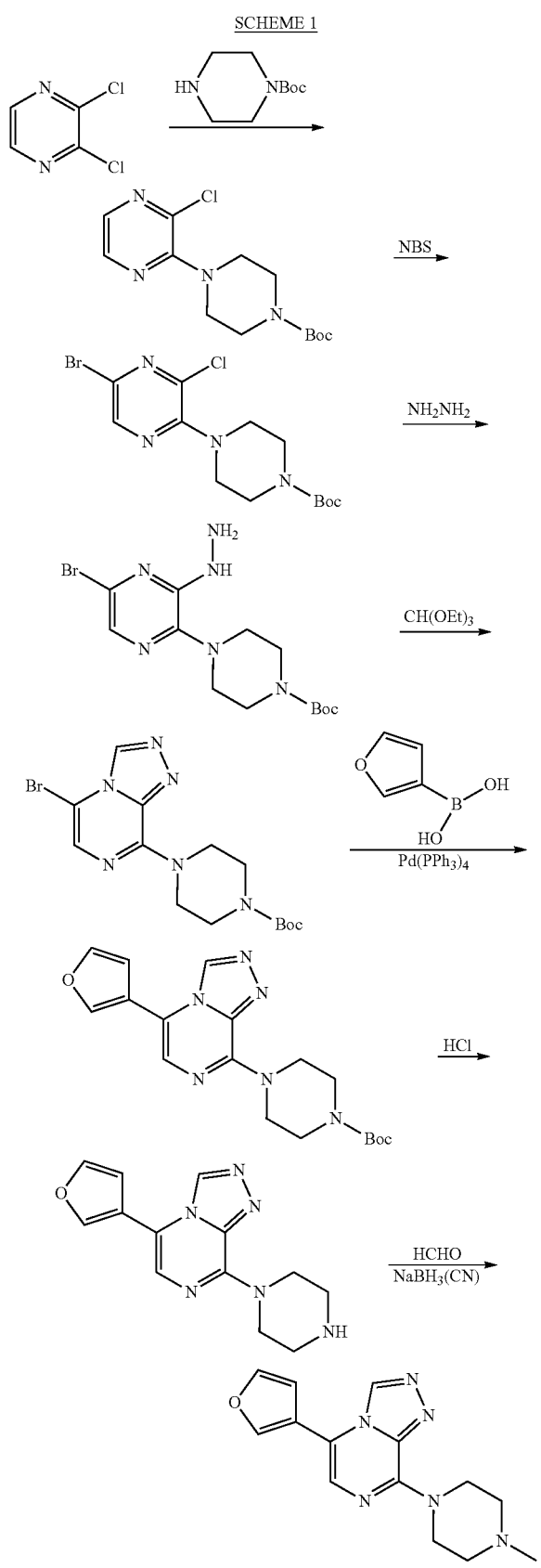

SCHEME 1

Example 1

5-(Furan-3-yl)-8-(4-methylpiperazin-1-yl)-[1,2,4]triazolo[4,3-a]pyrazine

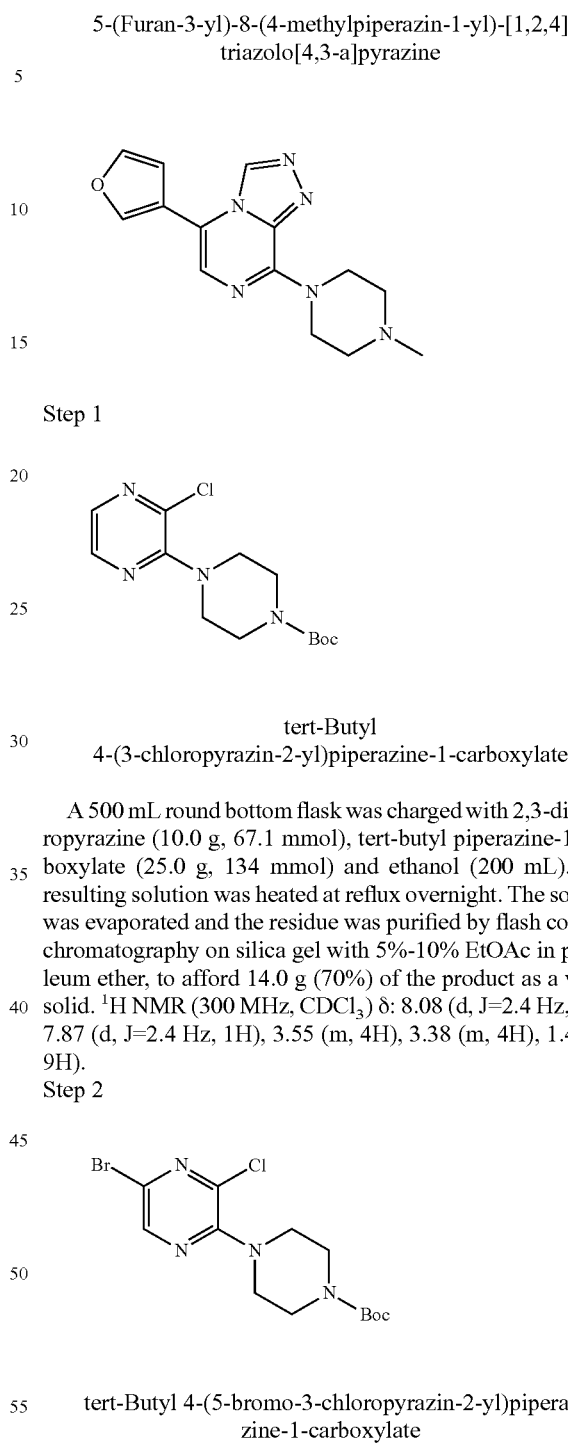

Step 1 tert-Butyl 4-(3-chloropyrazin-2-yl)piperazine-1-carboxylate

A 500 mL round bottom flask was charged with 2,3-dichloropyrazine (10.0 g, 67.1 mmol), tert-butyl piperazine-1-carboxylate (25.0 g, 134 mmol) and ethanol (200 mL). The resulting solution was heated at reflux overnight. The solvent was evaporated and the residue was purified by flash column chromatography on silica gel with 5%-10% EtOAc in petroleum ether, to afford 14.0 g (70%) of the product as a white solid. $^1$H NMR (300 MHz, CDCl$_3$) δ: 8.08 (d, J=2.4 Hz, 1H), 7.87 (d, J=2.4 Hz, 1H), 3.55 (m, 4H), 3.38 (m, 4H), 1.45 (s, 9H).

Step 2 tert-Butyl 4-(5-bromo-3-chloropyrazin-2-yl)piperazine-1-carboxylate

A 500 mL round bottom flask was charged with tert-butyl 4-(3-chloropyrazin-2-yl)piperazine-1-carboxylate (13.5 g, 45.3 mmol), N-bromosuccinimide (10.48 g, 58.9 mmol) and CHCl$_3$ (150 mL). The resulting mixture was stirred at 20° C. overnight and it became a clear solution. The solvent was evaporated and the residue was purified by flash column chromatography on silica gel with 0-10% EtOAc in petroleum ether, to afford 16.1 g (94%) of the product as a white solid. $^1$H NMR (300 MHz, CDCl$_3$) δ: 8.18 (s, 1H), 3.57 (m, 4H), 3.39 (m, 4H), 1.48 (s, 9H).

Step 3

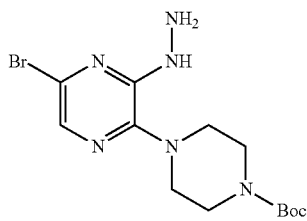

tert-Butyl 4-(5-bromo-3-hydrazinylpyrazin-2-yl)piperazine-1-carboxylate

A 500 mL 3-necked round bottom flask was charged with tert-butyl 4-(5-bromo-3-chloropyrazin-2-yl)piperazine-1-carboxylate (16.1 g, 42.6 mmol), hydrazine hydrate (4.2 mL, 85.2 mmol) and ethanol (200 mL). The resulting solution was refluxed overnight. TLC indicated an incomplete conversion. The solvent was evaporated and the residue was purified by flash column chromatography on silica gel with 10% EtOAc in petroleum ether then 2% methanol in dichloromethane, to afford 5.8 g (47%) of the product as a yellow solid. MS m/z: 373 (M+H$^+$).

Step 4

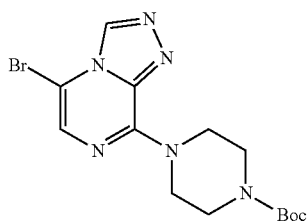 [SMILES: CC(C)(C)OC(=O)N1CCN(c2ncc(Br)n3cnnc23)CC1]

tert-Butyl 4-(5-bromo-[1,2,4]triazolo[4,3-a]pyrazin-8-yl)piperazine-1-carboxylate A 50 mL round bottom flask was charged with tert-butyl 4-(5-bromo-3-hydrazinylpyrazin-2-yl)piperazine-1-carboxylate (5.8 g, 20 mmol) and triethyl orthoformate (60 mL). The resulting solution was heated at 130° C. for 3 h. TLC indicated a complete conversion. The solvent was evaporated and the residue was purified by flash column chromatography on silica gel with 2% methanol in dichloromethane, to afford 5.3 g (69%) of the product as a yellow solid. MS m/z: 383 (M+H$^+$).

Step 5

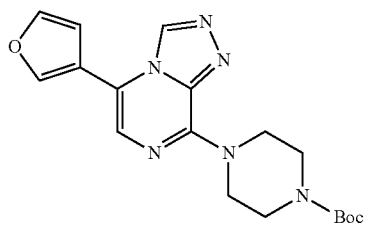 [SMILES: CC(C)(C)OC(=O)N1CCN(c2ncc(-c3ccoc3)n3cnnc23)CC1]

tert-Butyl 4-(5-(furan-3-yl)-[1,2,4]triazolo[4,3-a]pyrazin-8-yl)piperazine-1-carboxylate A 50 mL round bottom flask was charged with tert-butyl 4-(5-bromo-[1,2,4]triazolo[4,3-a]pyrazin-8-yl)piperazine-1-carboxylate (800 mg, 2.08 mmol), furan-3-ylboronic acid (349 mg, 3.12 mmol), Pd(PPh$_3$)$_4$ (240 mg, 0.312 mmol), Cs$_2$CO$_3$ (1.00 g, 3.12 mmol), 1,4-dioxane (11 mL) and water (4 mL). The resulting mixture was heated under N$_2$ at 100° C. overnight. Work-up: the reaction mixture was filtered. The filter cake was washed with EtOAc (10 mL) and the filtrate was extracted with more EtOAc (10 mL×3). The combined organic solutions were washed with brine, dried over anhydrous Na$_2$SO$_4$, and concentrated in vacuo. The residue was purified by flash column chromatography on silica gel with 2% methanol in dichloromethane, to afford 0.75 g (97%) of the product as a yellow solid. MS m/z: 371 (M+H$^+$).

Step 6

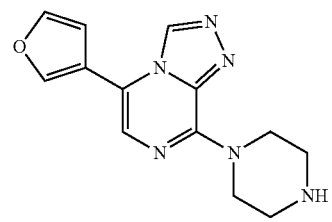 [SMILES: c1cc(-c2cnc(N3CCNCC3)c3nncn23)co1]

5-(Furan-3-yl)-8-(piperazin-1-yl)-[1,2,4]triazolo[4,3-a]pyrazine

A 50 mL round bottom flask was charged with tert-butyl 4-(5-(furan-3-yl)-[1,2,4]triazolo[4,3-a]pyrazin-8-yl)piperazine-1-carboxylate (500 mg, 1.35 mmol), dichloromethane (1 mL) and 2 M methanolic HCl (10 mL). The resulting solution was stirred at 20° C. overnight. The precipitate was collected by filtration, washed with methanol (10 mL), and dried, to afford 0.27 g (55%) of the HCl salt of the product as a yellow solid. $^1$H NMR (300 MHz, DMSO-d$_6$) δ: 9.50 (s, 1H), 8.44 (s, 1H), 7.90 (dd, J=1.8, 1.5 Hz, 1H), 7.68 (s, 1H), 7.09 (dd, J=1.8, 0.9 Hz, 1H), 4.49 (m, 4H), 3.25 (m, 4H). MS m/z: 271 (M+H$^+$).

Step 7

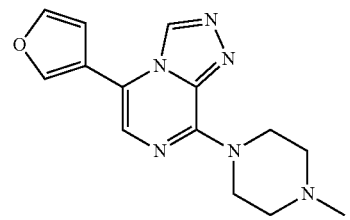 [SMILES: CN1CCN(c2ncc(-c3ccoc3)n3cnnc23)CC1]

5-(Furan-3-yl)-8-(4-methylpiperazin-1-yl)-[1,2,4]triazolo[4,3-a]pyrazine

A 50 mL round bottom flask was charged with 5-(furan-3-yl)-8-(piperazin-1-yl)-[1,2,4]triazolo[4,3-a]pyrazine HCl salt (350 mg, 1.14 mmol), 40% aqueous formaldehyde (20 mL), dichloromethane (20 mL), methanol (20 mL) and sodium cyanoborohydride (245 mg, 3.90 mmol) at 0° C. The resulting mixture was stirred at 20° C. overnight. It was then concentrated in vacuo and the residue was extracted with dichloromethane. The organic layer was washed with brine (10 mL), dried over anhydrous Na$_2$SO$_4$, and concentrated in vacuo. The crude product was re-crystallized from a 1/5 (v/v) dichloromethane/ethyl ether, to afford 0.16 g (49%) of the product as a yellow solid. $^1$H NMR (300 MHz, CDCl$_3$) δ: 8.83 (s, 1H), 7.76 (dd, J=1.5, 0.9 Hz, 1H), 7.62 (dd, J=1.8, 1.5 Hz, 1H), 7.36 (s, 1H), 6.68 (dd, J=1.8, 0.9 Hz, 1H), 4.41 (br, 4H), 2.59 (t, J=5.1 Hz, 4H), 2.36 (s, 3H). MS m/z: 285 (M+H$^+$).

Example 2

5-(Furan-3-yl)-8-(piperazin-1-yl)-[1,2,4]triazolo[4,3-a]pyrazine

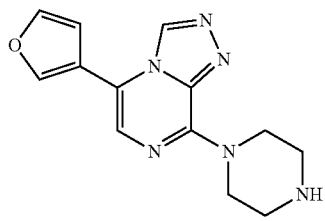 [SMILES: c1cc(-c2cnc(N3CCNCC3)c3nncn23)co1]

The HCl salt of the title compound was prepared as described in Example 1 step 6. $^1$H NMR (300 MHz, DMSO-d$_6$) δ: 9.50 (s, 1H), 8.44 (s, 1H), 7.90 (dd, J=1.8, 1.5 Hz, 1H), 7.68 (s, 1H), 7.09 (dd, J=1.8, 0.9 Hz, 1H), 4.49 (m, 4H), 3.25 (m, 4H). MS m/z: 271 (M+H$^+$).

Example 3

5-(Furan-2-yl)-8-(4-methylpiperazin-1-yl)-[1,2,4]triazolo[4,3-a]pyrazine

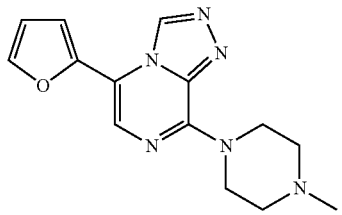 [SMILES: CN1CCN(c2ncc(-c3ccco3)n3cnnc23)CC1]

The title compound was prepared as described in Example 1, except that furan-2-ylboronic acid was substituted for furan-3-ylboronic acid in step 5 of that route. $^1$H NMR (300 MHz, CDCl$_3$) δ: 9.25-9.23 (m, 1H), 7.62-7.60 (m, 2H), 6.71-6.99 (m, 1H), 6.58-6.56 (m, 1H), 4.44 (br, 4H), 2.58 (br, 4H), 2.35 (s, 3H). MS m/z: 285 (M+H$^+$).

Example 4

5-(Furan-2-yl)-8-(piperazin-1-yl)-[1,2,4]triazolo[4,3-a]pyrazine

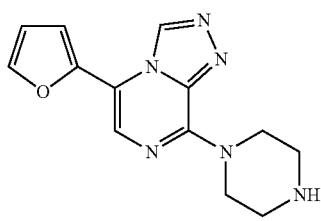 [SMILES: c1coc(-c2cnc(N3CCNCC3)c3nncn23)c1]

The HCl salt of the title compound was prepared as described in Example 3 step 6. $^1$H NMR (300 MHz, D$_2$O) δ: 9.32 (m, 1H), 7.58 (m, 1H), 7.28 (m, 1H), 6.72 (m, 1H), 6.51 (m, 1H), 4.24 (br, 4H), 3.35 (t, J=5.2 Hz, 4H). MS m/z: 271 (M+H$^+$).

Example 5

8-(4-Methylpiperazin-1-yl)-5-phenyl-[1,2,4]triazolo[4,3-a]pyrazine

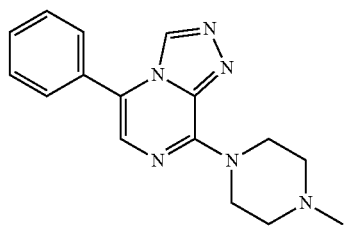 [SMILES: CN1CCN(c2ncc(-c3ccccc3)n3cnnc23)CC1]

The title compound was prepared as described in Example 1, except that phenylboronic acid was substituted for furan-3-ylboronic acid in step 5 of that route. $^1$H NMR (300 MHz, CDCl$_3$) δ: 8.85 (s, 1H), 7.54 (m, 5H), 7.33 (s, 1H), 4.42 (m, 4H), 2.62 (m, 4H), 2.37 (s, 3H). MS m/z: 295 (M+H$^+$).

Example 6

5-Phenyl-8-(piperazin-1-yl)-[1,2,4]triazolo[4,3-a]pyrazine

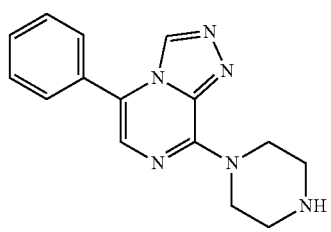 [SMILES: c1ccc(-c2cnc(N3CCNCC3)c3nncn23)cc1]

The HCl salt of the title compound was prepared as described in Example 5 step 6. $^1$H NMR (300 MHz, D$_2$O) δ: 9.10 (s, 1H), 7.44 (m, 5H), 7.18 (s, 1H), 4.37 (m, 4H), 3.39 (m, 4H). MS m/z: 281 (M+H$^+$).

Example 7

5-(3-Chlorophenyl)-8-(4-methylpiperazin-1-yl)-[1,2,4]triazolo[4,3-a]pyrazine

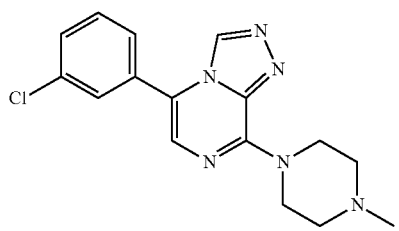 [SMILES: CN1CCN(c2ncc(-c3cccc(Cl)c3)n3cnnc23)CC1]

The title compound was prepared as described in Example 1, except that (3-chlorophenyl)boronic acid was substituted for furan-3-ylboronic acid in step 5 of that route. $^1$H NMR (300 MHz, CDCl$_3$) δ: 8.84 (s, 1H), 7.48 (m, 4H), 7.33 (s, 1H), 4.45 (m, 4H), 2.61 (m, 4H), 2.37 (s, 3H). MS m/z: 329 (M+H$^+$).

Example 8

5-(3-Chlorophenyl)-8-(piperazin-1-yl)-[1,2,4]triazolo[4,3-a]pyrazine

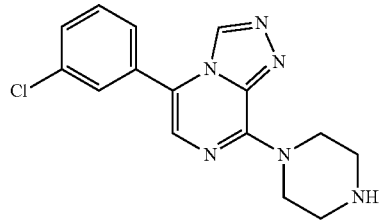 [SMILES: Clc1cccc(-c2cnc(N3CCNCC3)c3nncn23)c1]

The HCl salt of the title compound was prepared as described in Example 7 step 6. $^1$H NMR (300 MHz, D$_2$O) δ: 9.01 (s, 1H), 7.29 (m, 4H), 7.23 (s, 1H), 4.29 (m, 4H), 3.33 (m, 4H). MS m/z: 315 (M+H$^+$).

Example 9

5-(4-Chlorophenyl)-8-(4-methylpiperazin-1-yl)-[1,2,4]triazolo[4,3-a]pyrazine

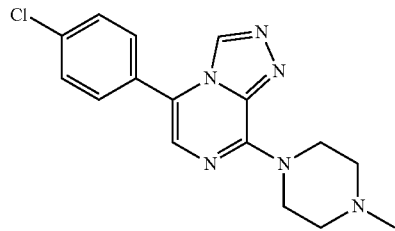 [SMILES: CN1CCN(c2ncc(-c3ccc(Cl)cc3)n3cnnc23)CC1]

The title compound was prepared as described in Example 1, except that (4-chlorophenyl)boronic acid was substituted for furan-3-ylboronic acid in step 5 of that route. $^1$H NMR (300 MHz, CDCl$_3$) δ: 8.81 (s, 1H), 7.50 (m, 4H), 7.31 (s, 1H), 4.43 (m, 4H), 2.61 (m, 4H), 2.37 (s, 3H). MS m/z: 329 (M+H$^+$).

Example 10

5-(4-Chlorophenyl)-8-(piperazin-1-yl)-[1,2,4]triazolo[4,3-a]pyrazine

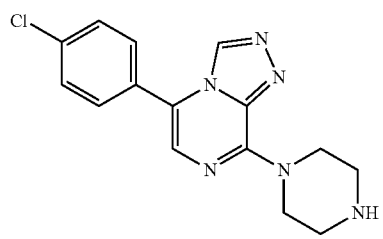 [SMILES: Clc1ccc(-c2cnc(N3CCNCC3)c3nncn23)cc1]

The HCl salt of the title compound was prepared as described in Example 9 step 6. $^1$H NMR (300 MHz, D$_2$O) δ: 8.99 (s, 1H), 7.29 (m, 4H), 7.09 (s, 1H), 4.26 (m, 4H), 3.13 (m, 4H). MS m/z: 315 (M+H$^+$).

Example 11

5-(2-Chlorophenyl)-8-(4-methylpiperazin-1-yl)-[1,2,4]triazolo[4,3-a]pyrazine

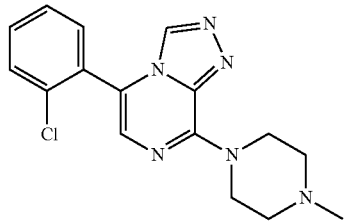 [SMILES: CN1CCN(c2ncc(-c3ccccc3Cl)n3cnnc23)CC1]

The title compound was prepared as described in Example 1, except that (2-chlorophenyl)boronic acid was substituted for furan-3-ylboronic acid in step 5 of that route. $^1$H NMR (300 MHz, CDCl$_3$) δ: 8.37 (s, 1H), 7.56 (m, 4H), 7.31 (s, 1H), 4.46 (m, 4H), 2.63 (m, 4H), 2.39 (s, 3H). MS m/z: 329 (M+H$^+$).

Example 12

5-(2-Chlorophenyl)-8-(piperazin-1-yl)-[1,2,4]triazolo[4,3-a]pyrazine

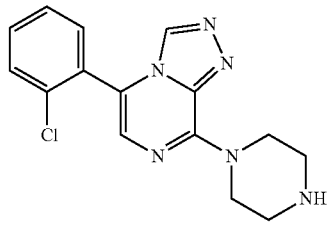 [SMILES: Clc1ccccc1-c1cnc(N2CCNCC2)c2nncn12]

The HCl salt of the title compound was prepared as described in Example 11 step 6. $^1$H NMR (300 MHz, D$_2$O) δ: 8.73 (s, 1H), 7.46 (m, 4H), 7.27 (s, 1H), 4.35 (m, 4H), 3.37 (m, 4H). MS m/z: 315 (M+H$^+$).

Example 13

5-(5-Chlorothiophen-2-yl)-8-(4-methylpiperazin-1-yl)-[1,2,4]triazolo[4,3-a]pyrazine

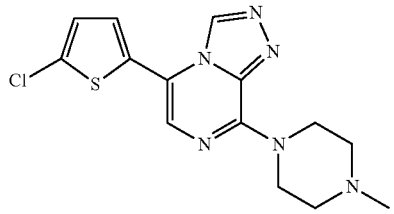 [SMILES: CN1CCN(c2ncc(-c3ccc(Cl)s3)n3cnnc23)CC1]

The title compound was prepared as described in Example 1, except that (5-chlorothiophen-2-yl)boronic acid was substituted for furan-3-ylboronic acid in step 5 of that route. $^1$H NMR (300 MHz, CDCl$_3$) δ: 8.97 (s, 1H), 7.39 (s, 1H), 7.10 (d, J=3.9 Hz, 1H), 7.01 (d, J=3.9 Hz, 1H), 4.44 (br, 4H), 2.58 (t, J=5.1 Hz, 4H), 2.36 (s, 3H). MS m/z: 335 (M+H$^+$).

Example 14

5-(5-Chlorothiophen-2-yl)-8-(piperazin-1-yl)-[1,2,4]triazolo[4,3-a]pyrazine

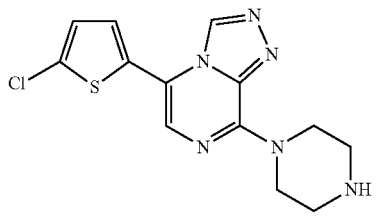 [SMILES: Clc1ccc(-c2cnc(N3CCNCC3)c3nncn23)s1]

The HCl salt of the title compound was prepared as described in Example 13 step 6. $^1$H NMR (300 MHz, DMSO-d$_6$) δ: 9.50 (s, 1H), 7.56 (d, J=0.9 Hz, 1H), 7.50 (d, J=3.9 Hz, 1H), 7.30 (d, J=3.9 Hz, 1H), 4.52 (br, 4H), 3.25 (br, 4H). MS m/z: 321 (M+H$^+$).

Example 15

8-(4-Methylpiperazin-1-yl)-5-(3-(trifluoromethyl)phenyl)-[1,2,4]triazolo[4,3-a]pyrazine

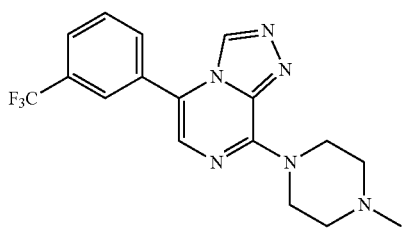 [SMILES: CN1CCN(c2ncc(-c3cccc(C(F)(F)F)c3)n3cnnc23)CC1]

The title compound was prepared as described in Example 1, except that (3-(trifluoromethyl)phenyl)boronic acid was substituted for furan-3-ylboronic acid in step 5 of that route. $^1$H NMR (300 MHz, CDCl$_3$) δ: 8.81 (s, 1H), 7.74 (m, 4H), 7.36 (s, 1H), 4.46 (m, 4H), 2.61 (m, 4H), 2.37 (s, 3H). MS m/z: 363 (M+H$^+$).

Example 16

8-(piperazin-1-yl)-5-(3-(trifluoromethyl)phenyl)-[1,2,4]triazolo[4,3-a]pyrazine

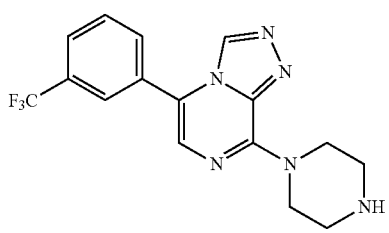 [SMILES: FC(F)(F)c1cccc(-c2cnc(N3CCNCC3)c3nncn23)c1]

The HCl salt of the title compound was prepared as described in Example 15 step 6. $^1$H NMR (300 MHz, D$_2$O) δ: 9.08 (s, 1H), 7.71 (m, 4H), 7.23 (s, 1H), 4.37 (m, 4H), 3.40 (m, 4H). MS m/z: 349 (M+H$^+$).

Example 17

5-(5-Chlorothiophen-3-yl)-8-(4-methylpiperazin-1-yl)-[1,2,4]triazolo[4,3-a]pyrazine

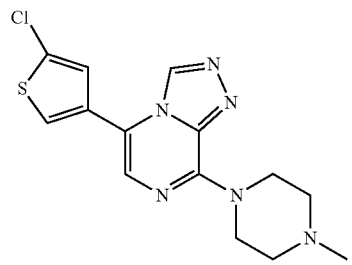 [SMILES: CN1CCN(c2ncc(-c3csc(Cl)c3)n3cnnc23)CC1]

The title compound was prepared as described in Example 1, except that (5-chlorothiophen-3-yl)boronic acid, which was prepared from thiophen-3-ylboronic acid and N-chlorosuccinimide as described below, was substituted for furan-3-ylboronic acid in step 5 of that route. $^1$H NMR (300 MHz, CDCl$_3$) δ: 8.87 (s, 1H), 7.35 (s, 1H), 7.30 (d, J=1.8 Hz, 1H), 7.13 (d, J=1.8 Hz, 1H), 4.56 (br, 4H), 2.60 (t, J=5.1 Hz, 4H), 2.37 (s, 3H). MS m/z: 335 (M+H$^+$).

A 50 mL round bottom flask was charged with thiophen-3-ylboronic acid (1.0 g, 7.8 mmol), N-chlorosuccinimide (1.26 g, 9.4 mmol) and THF (20 mL). The resulting mixture was heated at 60° C. overnight. Reaction progress was monitored by TLC (EtOAc/petroleum ether=1:10). Work-up: the solvent was evaporated to afford 1.1 g of a yellow oil (3 spots by TLC), which was used in the next step without further purification.

Example 18

5-(5-Chlorothiophen-3-yl)-8-(piperazin-1-yl)-[1,2,4]triazolo[4,3-a]pyrazine

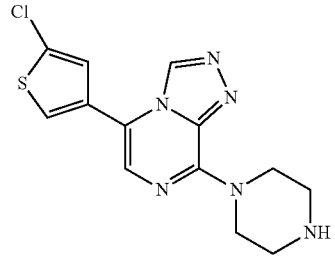 [SMILES: Clc1cc(-c2cnc(N3CCNCC3)c3nncn23)cs1]

The title compound was prepared as described in Example 17 step 6. $^1$H NMR (300 MHz, CDCl$_3$) δ: 8.87 (s, 1H), 7.35 (s, 1H), 7.30 (d, J=1.8 Hz, 1H), 7.13 (d, J=1.8 Hz, 1H), 4.38 (br, 4H), 3.05 (t, J=5.1 Hz, 4H). MS m/z: 321 (M+H$^+$).

Example 19

8-(4-Methylpiperazin-1-yl)-5-(thiophen-2-yl)-[1,2,4]triazolo[4,3-a]pyrazine

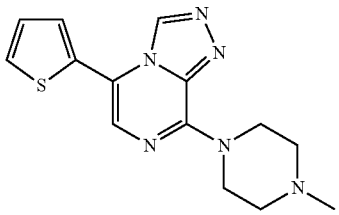

The title compound was prepared as described in Example 1, except that thiophen-2-ylboronic acid was substituted for furan-3-ylboronic acid in step 5 of that route. $^1$H NMR (300 MHz, CDCl$_3$) δ: 9.02 (s, 1H), 7.48 (dd, J=5.1, 0.9 Hz, 1H), 7.45 (s, 1H), 7.34 (dd, J=3.6, 0.9 Hz, 1H), 7.20 (dd, J=5.1, 3.6 Hz, 1H), 4.44 (br, 4H), 2.59 (t, J=4.8 Hz, 4H), 2.36 (s, 3H). MS m/z: 301 (M+H$^+$).

Example 20

5-(8-(4-Methylpiperazin-1-yl)-[1,2,4]triazolo[4,3-a]pyrazin-5-yl)thiazole

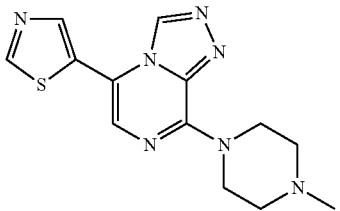 [SMILES: CN1CCN(c2ncc(-c3cncs3)n3cnnc23)CC1]

The title compound was prepared as described in Example 1, except that 5-(tributylstannyl)thiazole (Reference for Stille coupling: US2010/120741 A1 Example 88) was substituted for furan-3-ylboronic acid in step 5 of that route. $^1$H NMR (300 MHz, CDCl$_3$) δ: 8.94 (d, J=0.6 Hz, 1H), 8.89 (s, 1H), 8.12 (d, J=0.6 Hz, 1H), 7.47 (s, 1H), 4.46 (br, 4H), 2.60 (t, J=5.4 Hz, 4H), 2.37 (s, 3H). MS m/z: 302 (M+H$^+$).

Example 21

5-(8-(piperazin-1-yl)-[1,2,4]triazolo[4,3-a]pyrazin-5-yl)thiazole

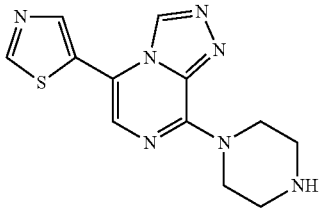

The HCl salt of the title compound was prepared as described in Example 20 step 6. $^1$H NMR (300 MHz, D$_2$O) δ: 9.27-9.23 (m, 1H), 9.15 (d, J=0.9 Hz, 1H), 8.21-8.19 (m, 1H), 7.46 (s, 1H), 4.42-4.39 (m, 4H), 3.38 (t, J=5.7 Hz, 4H). MS m/z: 288 (M+H$^+$).

Example 22

2-(8-(4-Methylpiperazin-1-yl)-[1,2,4]triazolo[4,3-a]pyrazin-5-yl)thiazole

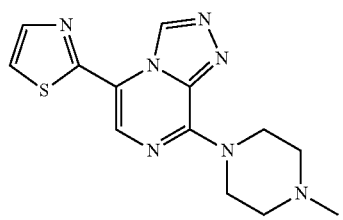 [SMILES: CN1CCN(c2ncc(-c3nccs3)n3cnnc23)CC1]

The title compound was prepared as described in Example 1, except that 2-(tributylstannyl)thiazole (Reference for Stille coupling: US2010/120741 A1 Example 88) was substituted for furan-3-ylboronic acid in step 5 of that route. $^1$H NMR (300 MHz, CDCl$_3$) δ: 10.31 (s, 1H), 7.97 (s, 1H), 7.92 (d, J=3.3 Hz, 1H), 7.31 (d, J=3.3 Hz, 1H), 4.51 (br, 4H), 2.60 (t, J=5.1 Hz, 4H), 2.37 (s, 3H). MS m/z: 302 (M+H$^+$).

Example 23

2-(8-(piperazin-1-yl)-[1,2,4]triazolo[4,3-a]pyrazin-5-yl)thiazole

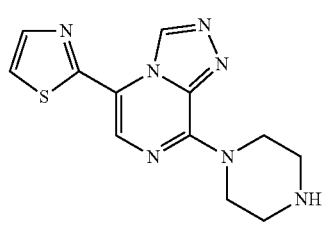 [SMILES: c1csc(-c2cnc(N3CCNCC3)c3nncn23)n1]

The HCl salt of the title compound was prepared as described in Example 22 step 6. $^1$H NMR (300 MHz, D$_2$O) δ: 9.95 (s, 1H), 7.89-7.88 (m, 1H), 7.80-7.79 (m, 1H), 7.57-7.56 (m, 1H), 4.42-4.39 (m, 4H), 3.37 (t, J=5.4 Hz, 4H). MS m/z: 288 (M+H$^+$).

Example 24

5-Isobutyl-8-(4-methylpiperazin-1-yl)-[1,2,4]triazolo[4,3-a]pyrazine

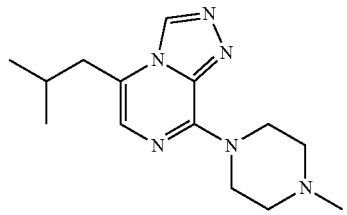 [SMILES: CC(C)Cc1cnc(N2CCN(C)CC2)c2nncn12]

The HCl salt of the title compound was prepared as described in Example 1, except the step 5 of that route, which is described as below. $^1$H NMR (300 MHz, D$_2$O) δ: 9.14 (s, 1H), 7.10 (s, 1H), 4.98 (d, J=15.0 Hz, 2H), 3.57 (d, J=11.7 Hz, 2H), 3.43 (t, J=13.5 Hz, 2H), 3.21 (t, J=6.2 Hz, 2H), 2.86 (s, 3H), 2.64 (d, J=7.2 Hz, 2H), 1.94 (m, 1H), 0.82 (d, J=6.6 Hz, 6H). MS m/z: 275 (M+H$^+$).

A 50 mL round bottom flask was charged with tert-butyl 4-(5-bromo-[1,2,4]triazolo[4,3-a]pyrazin-8-yl)piperazine-1-carboxylate (0.5 g, 1.3 mmol), Pd(PPh$_3$)$_2$Cl$_2$ (140.3 mg, 0.20 mmol) and toluene (8 mL) under N$_2$. To the above was injected a 2 M solution of isobutylzinc(II) bromide in THF (10.4 mL, 5.2 mmol). The resulting mixture was stirred under N$_2$ at 20° C. for 0.5 h then 100° C. overnight. Work-up: the reaction mixture was filtered. The filter cake was washed with EtOAc (10 mL) and the filtrate was extracted with more EtOAc (10 mL×3). The combined organic solutions were washed with brine, dried over anhydrous Na$_2$SO$_4$, and concentrated in vacuo. The residue was purified by flash column chromatography on silica gel with 2% methanol in dichloromethane, to afford 0.30 g (64%) of tert-butyl 4-(5-isobutyl-[1,2,4]triazolo[4,3-a]pyrazin-8-yl)piperazine-1-carboxylate as a yellow solid. MS m/z: 361 (M+H$^+$).

Example 25

5-Isopentyl-8-(4-methylpiperazin-1-yl)-[1,2,4]triazolo[4,3-a]pyrazine

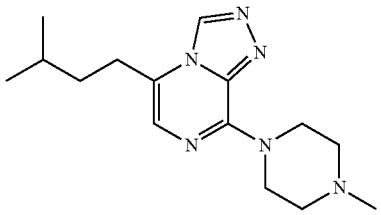 [SMILES: CC(C)CCc1cnc(N2CCN(C)CC2)c2nncn12]

The title compound was prepared as described in Example 1, except the step 5 of that route, which is described as below. $^1$H NMR (300 MHz, CDCl$_3$) δ: 8.70 (s, 1H), 7.13 (s, 1H), 4.33 (t, J=4.5 Hz, 4H), 2.78 (t, J=7.6 Hz, 2H), 2.58 (t, J=5.1 Hz, 4H), 2.36 (s, 3H), 1.68-1.58 (m, 3H), 0.99 (d, J=6.3 Hz, 6H). MS m/z: 289 (M+H$^+$).

A 50 mL round bottom flask was charged with tert-butyl 4-(5-bromo-[1,2,4]triazolo[4,3-a]pyrazin-8-yl)piperazine-1-carboxylate (1.0 g, 2.61 mmol), isopentylboronic acid (484 mg, 4.18 mmol), Pd(PPh$_3$)$_4$ (300 mg, 0.261 mmol), 2 M aqueous K$_2$CO$_3$ (2.6 mL, 5.2 mmol) and toluene (15 mL) under N$_2$. The resulting mixture was heated under N$_2$ at 100° C. overnight. Work-up: the reaction mixture was filtered. The filter cake was washed with EtOAc (10 mL) and the filtrate was extracted with more EtOAc (10 mL×3). The combined organic solutions were washed with brine, dried over anhydrous Na$_2$SO$_4$, and concentrated in vacuo. The residue was purified by flash column chromatography on silica gel with 2% methanol in dichloromethane, to afford 0.43 g (44%) of tert-butyl 4-(5-isopentyl-[1,2,4]triazolo[4,3-a]pyrazin-8-yl)piperazine-1-carboxylate as a yellow solid. MS m/z: 375 (M+H$^+$).

Example 26

5-Isopentyl-8-(piperazin-1-yl)-[1,2,4]triazolo[4,3-a]pyrazine

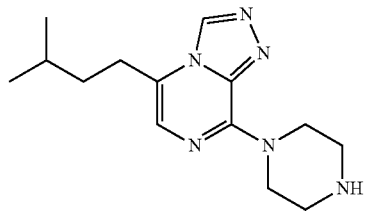 [SMILES: CC(C)CCc1cnc(N2CCNCC2)c2nncn12]

The HCl salt of the title compound was prepared as described in Example 25 step 6. $^1$H NMR (300 MHz, D$_2$O) δ: 9.28 (s, 1H), 7.16 (s, 1H), 4.40 (m, 4H), 3.49 (m, 4H), 2.90 (t, J=7.6 Hz, 2H), 1.67-1.57 (m, 3H), 0.92 (d, J=6.0 Hz, 6H). MS m/z: 275 (M+H$^+$).

SCHEME 2

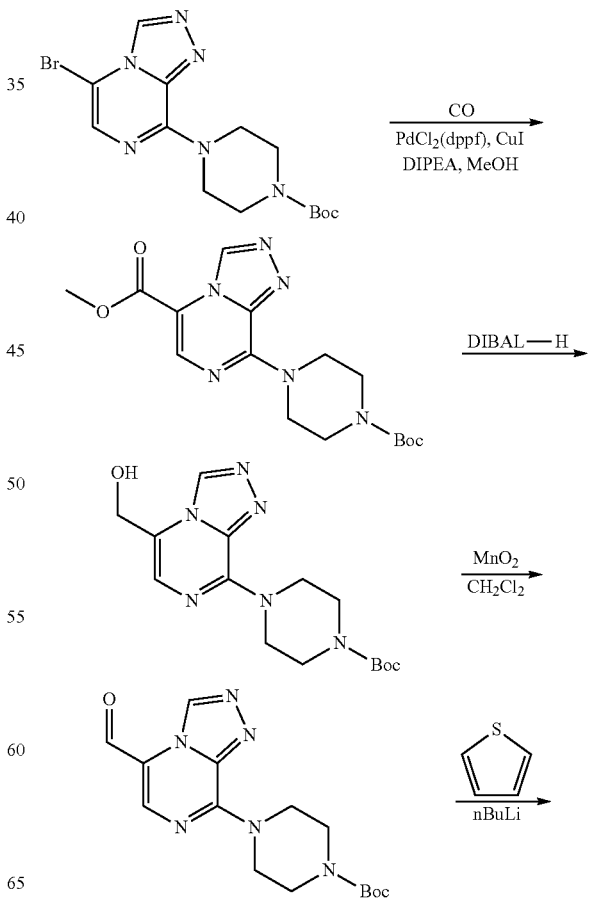

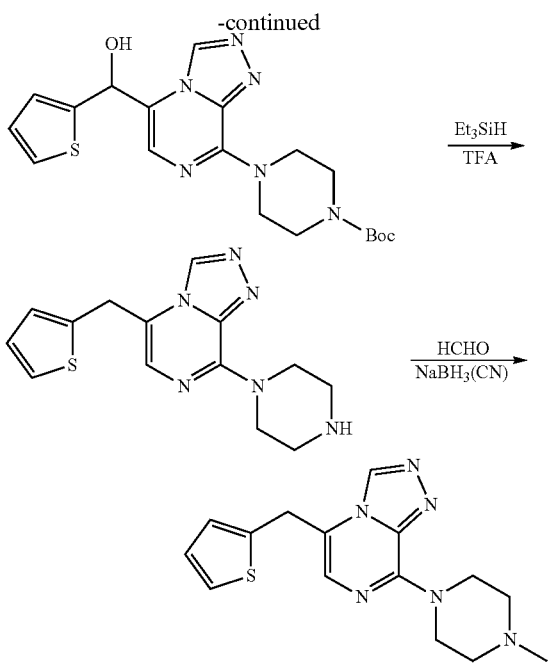

Example 27

8-(4-Methylpiperazin-1-yl)-5-(thiophen-2-ylmethyl)-[1,2,4]triazolo[4,3-a]pyrazine

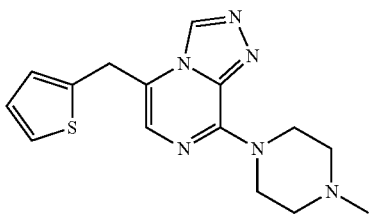 [SMILES: CN1CCN(c2ncc(Cc3cccs3)n3cnnc23)CC1]

Step 1

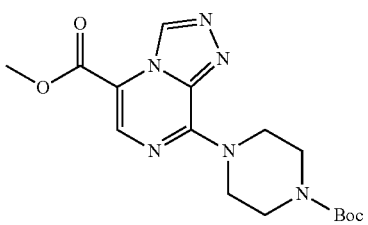 [SMILES: COC(=O)c1cnc(N2CCN(C(=O)OC(C)(C)C)CC2)c2nncn12]

Methyl 8-(4-(tert-butoxycarbonyl)piperazin-1-yl)-[1,2,4]triazolo[4,3-a]pyrazine-5-carboxylate A 300 mL pressure vessel was charged with tert-butyl 4-(5-bromo-[1,2,4]triazolo[4,3-a]pyrazin-8-yl)piperazine-1-carboxylate (prepared as described in Example 1 steps 1-4, 10.0 g, 26 mmol), CuI (1.5 g, 7.8 mmol), Pd(dppf)Cl$_2$ (6.4 g, 7.8 mmol), N,N-diisopropylethylamine (10 mL) and MeOH (100 mL). The vessel was charged with carbon monoxide (3.5 bar) and the reaction mixture was magnetically stirred at 100° C. for 12 h. Work-up: after the reaction mixture was cooled to room temperature, the vessel was opened. The reaction solution was diluted with saturated aqueous NaHCO$_3$ (100 mL) and extracted with EtOAc (200 mL×3). The combined organic layers were dried over anhydrous Na$_2$SO$_4$ and concentrated in vacuo. The residue was purified by flash column chromatography on silica gel with 2% MeOH in CH$_2$Cl$_2$, to afford 7.0 g (73%) of the product as a white solid. MS m/z: 363 (M+H$^+$).

Step 2

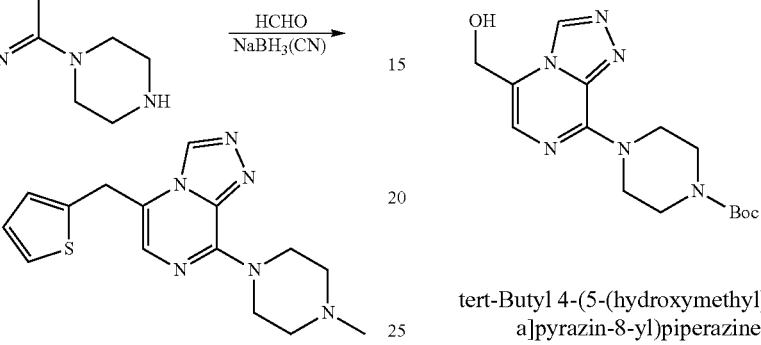

tert-Butyl 4-(5-(hydroxymethyl)-[1,2,4]triazolo[4,3-a]pyrazin-8-yl)piperazine-1-carboxylate A 250 mL 3-necked round bottom flask was charged with methyl 8-(4-(tert-butoxycarbonyl)piperazin-1-yl)-[1,2,4]triazolo[4,3-a]pyrazine-5-carboxylate (3.0 g, 8.3 mmol) and dry CH$_2$Cl$_2$ (30 mL). To the above was added dropwise a solution of 1.5 M diisobutylaluminum hydride in toluene (11 mL, 16.5 mmol) at −78° C. The resulting mixture was stirred at −78° C. for further 1 h then quenched by slow addition of methanol (10 mL). The mixture was poured into saturated aqueous NH$_4$Cl (200 mL) and extracted with ethyl ether (100 mL×2). The combined organic layers were washed with saturated aqueous NaHCO$_3$ (100 mL) and brine (100 mL), dried over anhydrous Na$_2$SO$_4$ and concentrated in vacuo. The residue was further purified by flash column chromatography on silica gel with 3% MeOH in CH$_2$Cl$_2$, to afford 1.4 g (50%) of the product as a white solid. MS m/z: 335 (M+H$^+$).

Step 3

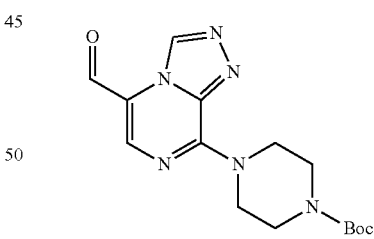

tert-Butyl 4-(5-formyl-[1,2,4]triazolo[4,3-a]pyrazin-8-yl)piperazine-1-carboxylate A 250 mL round bottom flask was charged with tert-butyl 4-(5-(hydroxymethyl)-[1,2,4]triazolo[4,3-a]pyrazin-8-yl)piperazine-1-carboxylate (0.30 g, 0.90 mmol) and dry CH$_2$Cl$_2$ (20 mL). To the above was added activated MnO$_2$ (0.23 g, 2.6 mmol). The resulting suspension was stirred at room temperature for 16 h. Work-up: the reaction mixture was filtered. The filtrate was concentrated in vacuo, to afford 0.26 g (87%) of the product as a yellow solid. MS m/z: 333 (M+H$^+$).

Step 4

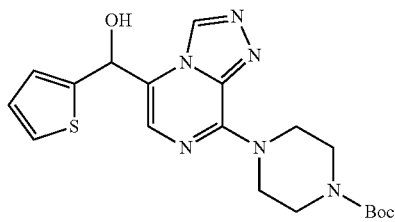 [SMILES: CC(C)(C)OC(=O)N1CCN(c2ncc(C(O)c3cccs3)n3cnnc23)CC1]

tert-Butyl 4-(5-(hydroxy(thiophen-2-yl)methyl)-[1,2,4]triazolo[4,3-a]pyrazin-8-yl)piperazine-1-carboxylate A 250 mL 3-necked round bottom flask was charged with thiophene (0.63 g, 7.5 mmol) and dry ethyl ether (10 mL). To the above was added dropwise nBuLi solution (2.5 M in hexane, 3 mL, 7.5 mmol) at 0° C. The mixture was stirred at 0° C. for 1 h, and was then cooled to −78° C. A solution of tert-butyl 4-(5-formyl-[1,2,4]-triazolo[4,3-a]pyrazin-8-yl)piperazine-1-carboxylate (1.0 g, 3.0 mmol) in dry $CH_2Cl_2$ (10 mL) was added dropwise at that temperature. The resulting mixture was stirred at −78° C. for 0.5 h, and then quenched by slow addition of methanol (10 mL). The reaction mixture was poured into saturated aqueous $NH_4Cl$ (100 mL) and extracted with ethyl ether (100 mL×2). The combined organic layers were washed with saturated aqueous $NaHCO_3$ (100 mL), dried over anhydrous $Na_2SO_4$ and concentrated in vacuo. The residue was further purified by flash column chromatography on silica gel with 1% MeOH in $CH_2Cl_2$, to afford 0.90 g (72%) of the product as a white solid. MS m/z: 417 (M+H$^+$).

Step 5

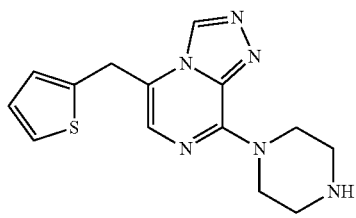 [SMILES: c1csc(Cc2cnc(N3CCNCC3)c3nncn23)c1]

8-(piperazin-1-yl)-5-(thiophen-2-ylmethyl)-[1,2,4]triazolo[4,3-a]pyrazine

A 50 mL round bottom flask was charged with tert-butyl 4-(5-(hydroxy(thiophen-2-yl)methyl)-[1,2,4]-triazolo[4,3-a]pyrazin-8-yl)piperazine-1-carboxylate (0.40 g, 0.96 mmol) and $CF_3COOH$ (10 mL). To the above was added triethylsilane (2 mL). The resulting mixture was stirred at room temperature for 16 h. Work-up: the solvent was evaporated. The residue was mixed with saturated aqueous $NaHCO_3$ (100 mL) and extracted with $CH_2Cl_2$ (50 mL×3). The combined organic layers were dried over anhydrous $Na_2SO_4$ and concentrated in vacuo. The residue was further purified by flash column chromatography on silica gel with 2% MeOH in $CH_2Cl_2$, to afford 0.20 g (69%) of the product as a white solid. It was converted into the corresponding HCl salt by treating with methanolic HCl solution. $^1$H NMR (300 MHz, D$_2$O) δ: 9.07 (s, 1H), 7.23 (dd, J=4.8, 0.9 Hz, 1H), 7.15 (s, 1H), 6.95-6.89 (m, 2H), 4.39 (br, 6H), 3.42 (m, 4H). MS m/z: 301 (M+H$^+$).

Step 6

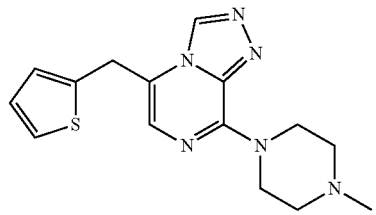 [SMILES: CN1CCN(c2ncc(Cc3cccs3)n3cnnc23)CC1]

8-(4-Methylpiperazin-1-yl)-5-(thiophen-2-ylmethyl)-[1,2,4]triazolo[4,3-a]pyrazine A 100 mL round bottom flask was charged with 8-(piperazin-1-yl)-5-(thiophen-2-ylmethyl)-[1,2,4]-triazolo[4,3-a]pyrazine (0.26 g, 0.87 mmol), $CH_2Cl_2$ (20 mL), MeOH (10 mL), 40% aqueous HCHO (2 mL) and NaBH$_3$(CN) (0.17 g, 2.6 mmol). The resulting solution was stirred at room temperature for 0.5 h. Work-up: the reaction mixture was diluted with saturated aqueous $NaHCO_3$ and extracted with $CH_2Cl_2$ (50 mL×3). The combined $CH_2Cl_2$ layers were dried over anhydrous $Na_2SO_4$ and concentrated in vacuo. The residue was purified by flash column chromatography on silica gel with 1-5% MeOH in $CH_2Cl_2$, to afford 0.18 g (69%) of the product as a yellow solid. It was converted into the corresponding HCl salt by treating with methanolic HCl solution. $^1$H NMR (300 MHz, D$_2$O) δ: 9.01 (s, 1H), 7.19 (m, 2H), 6.89 (m, 2H), 5.08 (d, J=15.0 Hz, 2H), 4.36 (s, 2H), 3.63-3.49 (m, 4H), 3.24 (m, 2H), 2.86 (s, 3H). MS m/z: 315 (M+H$^+$).

Example 28

8-(piperazin-1-yl)-5-(thiophen-2-ylmethyl)-[1,2,4]triazolo[4,3-a]pyrazine

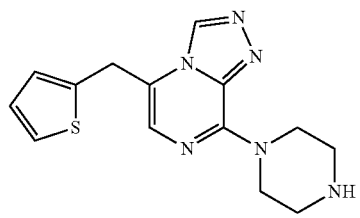 [SMILES: c1csc(Cc2cnc(N3CCNCC3)c3nncn23)c1]

The HCl salt of the title compound was prepared as described in Example 27 step 5. $^1$H NMR (300 MHz, D$_2$O) δ: 9.07 (s, 1H), 7.23 (dd, J=4.8, 0.9 Hz, 1H), 7.15 (s, 1H), 6.95-6.89 (m, 2H), 4.39 (br, 6H), 3.42 (m, 4H). MS m/z: 301 (M+H$^+$).

Example 29

8-(4-Methylpiperazin-1-yl)-5-(thiophen-3-ylmethyl)-[1,2,4]triazolo[4,3-a]pyrazine

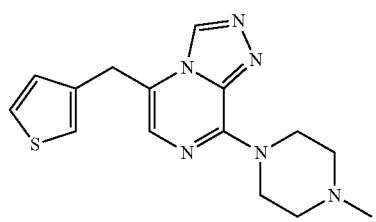 [SMILES: CN1CCN(c2ncc(Cc3ccsc3)n3cnnc23)CC1]

The HCl salt of the title compound was prepared as described in Example 27, except that 3-bromothiophene was substituted for thiophene in step 4 of that route. $^1$H NMR (300 MHz, D$_2$O) δ: 9.04 (s, 1H), 7.25 (dd, J=5.1, 3.0 Hz, 1H), 7.12 (br, 1H), 7.06 (s, 1H), 6.85 (d, J=5.1 Hz, 1H), 5.15 (d, J=14.7 Hz, 2H), 4.13 (s, 2H), 3.76-3.62 (m, 4H), 3.28 (m, 2H), 2.88 (s, 3H). MS m/z: 315 (M+H$^+$).

Example 30

8-(piperazin-1-yl)-5-(thiophen-3-ylmethyl)-[1,2,4]triazolo[4,3-a]pyrazine

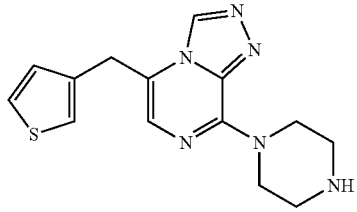 [SMILES: c1cc(Cc2cnc(N3CCNCC3)c3nncn23)cs1]

The HCl salt of the title compound was prepared as described in Example 29 step 5. $^1$H NMR (300 MHz, D$_2$O) δ: 9.09 (s, 1H), 7.32 (dd, J=5.1, 3.0 Hz, 1H), 7.20 (m, 1H), 7.07 (s, 1H), 6.93 (dd, J=5.1, 1.2 Hz, 1H), 4.48 (t, J=5.4 Hz, 4H), 4.20 (s, 2H), 3.48 (t, J=5.4 Hz, 4H). MS m/z: 301 (M+H$^+$).

SCHEME 3

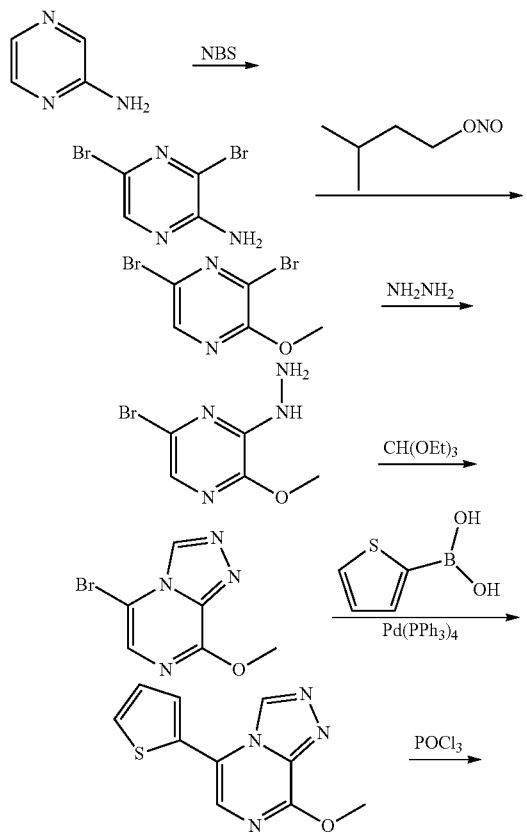

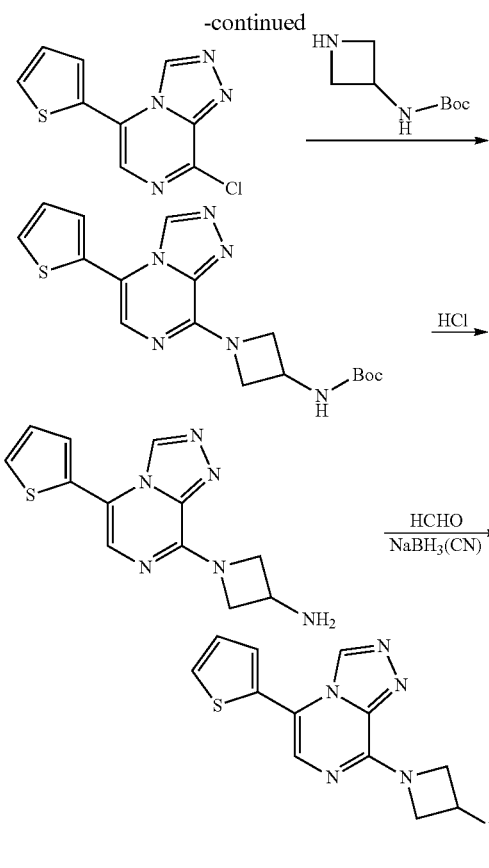

Example 31

N,N-Dimethyl-1-(5-(thiophen-2-yl)-[1,2,4]triazolo[4,3-a]pyrazin-8-yl)azetidin-3-amine

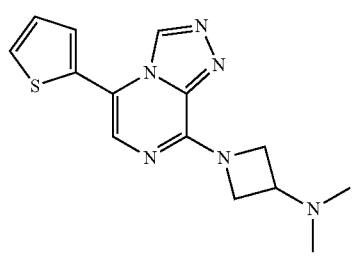 [SMILES: CN(C)C1CN(c2ncc(-c3cccs3)n3cnnc23)C1]

Step 1

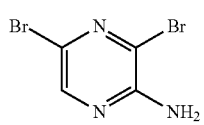

3,5-Dibromopyrazin-2-amine

A 1 L three-necked round bottom flask was charged with pyrazin-2-amine (20 g, 0.21 mol), DMSO (600 mL) and water (15 mL). To the above was added in portions N-Bromosuccinimide (77.9 g, 0.44 mol) while keeping the inner temperature below 5° C. The resulting mixture was stirred at 20° C. overnight. The solvent was evaporated and the residue was purified by flash column chromatography on silica gel with a 1:10 EtOAc/petroleum ether, to afford 18 g (34%) of the product as a yellows solid. ¹H NMR (300 MHz, CDCl₃) δ: 8.02 (s, 1H), 4.72 (br, 2H).
Step 2

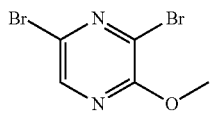

3,5-Dibromo-2-methoxypyrazine

A 100 mL round bottom flask was charged with 3,5-dibromopyrazin-2-amine (1.0 g, 4.0 mmol), methanol (10 mL), methanolic HCl (2.5 M, 0.32 mL, 0.80 mmol) and isoamylnitrile (1.6 mL, 12 mmol). The resulting mixture was heated at 60° C. for 2 h. TLC indicated a complete conversion. Work-up: the solvent was evaporated. The residue was re-dissolved in dichloromethane, washed with saturated aqueous NaHCO₃ and brine. The organic layer was dried over anhydrous Na₂SO₄ and concentrated in vacuo. The residue was further purified by flash column chromatography on silica gel with a 1:20 EtOAc/petroleum ether, to afford 0.50 g (47%) of the product as a white crystal. MS m/z: 267 (M+H⁺).
Step 3

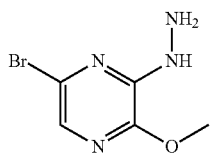

5-Bromo-3-hydrazinyl-2-methoxypyrazine

A 100 mL round bottom flask was charged with 3,5-dibromo-2-methoxypyrazine (0.50 g, 1.9 mmol), hydrazine hydrate (0.47 g, 9.4 mmol) and ethanol (5 mL). The resulting mixture was heated at 80° C. for 4 h. TLC indicated a complete conversion. Work-up: the reaction solution was concentrated in vacuo, to afford 0.5 g (crude) of the product as a brown solid, which was used in the next step without further purification.
Step 4

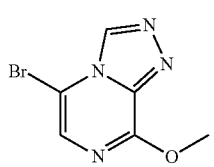

5-Bromo-8-methoxy-[1,2,4]triazolo[4,3-a]pyrazine

A 100 mL round bottom flask was charged with 5-bromo-3-hydrazinyl-2-methoxypyrazine (0.5 g crude, ~1.9 mmol) and triethyl orthoformate (5 mL). The resulting mixture was heated at 130° C. overnight. TLC indicated a complete conversion. Work-up: the reaction mixture was concentrated. The residue was purified by flash column chromatography on silica gel with a 1:50 methanol/dichloromethane, to afford 0.28 g (66% for 2 steps) of the product as a pale yellow solid. ¹H NMR (300 MHz, CDCl₃) δ: 8.93 (s, 1H), 7.47 (s, 1H), 4.18 (s, 3H). MS m/z: 229 (M+H⁺).
Step 5

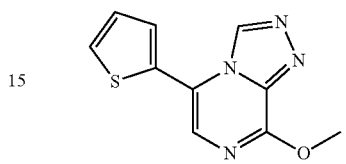

8-Methoxy-5-(thiophen-2-yl)-[1,2,4]triazolo[4,3-a] pyrazine

A 50 mL round bottom flask was charged with 5-bromo-8-methoxy-[1,2,4]triazolo[4,3-a]pyrazine (0.25 g, 1.1 mmol), thiophen-2-ylboronic acid (280 mg, 2.2 mmol), Pd(PPh₃)₄ (190 mg, 0.16 mmol), Cs₂CO₃ (530 mg, 1.6 mmol), 1,4-dioxane (11 mL) and water (4 mL). The resulting mixture was heated under N₂ at 100° C. overnight. Work-up: the reaction mixture was filtered. The filter cake was washed with EtOAc (10 mL) and the filtrate was extracted with more EtOAc (10 mL×3). The combined organic solutions were washed with brine, dried over anhydrous Na₂SO₄, and concentrated in vacuo. The residue was purified by flash column chromatography on silica gel with a 1:50 methanol/dichloromethane, to afford 0.25 g (99%) of the product as a yellow solid. MS m/z: 233 (M+H⁺).
Step 6

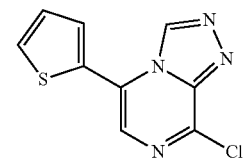 [SMILES: Clc1ncc(-c2cccs2)n2cnnc12]

8-Chloro-5-(thiophen-2-yl)-[1,2,4]triazolo[4,3-a] pyrazine

A 50 mL round bottom flask was charged with 8-methoxy-5-(thiophen-2-yl)-[1,2,4]triazolo[4,3-a]pyrazine (0.30 g, 1.3 mmol) and POCl₃ (3 mL). The mixture was heated at 130° C. overnight. TLC indicated a complete conversion. Work-up: the reaction mixture was concentrated in vacuo. The residue was carefully poured into ice and extracted with EtOAc (10 mL). The organic layer was washed with saturated aqueous NaHCO₃ and brine, dried over anhydrous Na₂SO₄, and concentrated in vacuo. The residue was further purified by flash column chromatography on silica gel with a 1:5 EtOAc/petroleum ether, to afford 0.23 g (75%) of the product as a white solid. MS m/z: 237 (M+H⁺).

Step 7

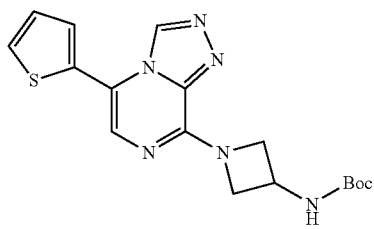 [SMILES: CC(C)(C)OC(=O)NC1CN(c2ncc(-c3cccs3)n3cnnc23)C1]

tert-Butyl (1-(5-(thiophen-2-yl)-[1,2,4]triazolo[4,3-a]pyrazin-8-yl)azetidin-3-yl)carbamate A 50 mL round bottom flask was charged with 8-chloro-5-(thiophen-2-yl)-[1,2,4]triazolo[4,3-a]pyrazine (0.25 g, 1.1 mmol), tert-butyl azetidin-3-ylcarbamate (540 mg, 3.1 mmol) and ethanol (5 mL). The resulting solution was refluxed overnight. Work-up: the solvent was evaporated. The residue was purified by flash column chromatography on silica gel with a 1:2 EtOAc/petroleum ether and then a 1:50 methanol/dichloromethane, to afford 130 mg (33%) of the product as a white solid. MS m/z: 373 (M+H$^+$).

Step 8

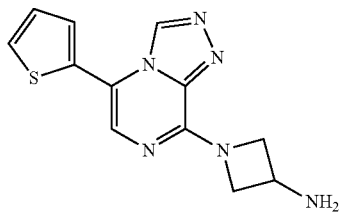 [SMILES: NC1CN(c2ncc(-c3cccs3)n3cnnc23)C1]

1-(5-(Thiophen-2-yl)-[1,2,4]triazolo[4,3-a]pyrazin-8-yl)azetidin-3-amine

A 50 mL round bottom flask was charged with tert-butyl (1-(5-(thiophen-2-yl)-[1,2,4]triazolo[4,3-a]pyrazin-8-yl)azetidin-3-yl)carbamate (130 mg, 0.35 mmol), dichloromethane (1 mL) and 3 M methanolic HCl (6 mL). The resulting solution was stirred at 20° C. overnight. The precipitate was collected by filtration, washed with ethyl ether (5 mL), and dried, to afford 80 mg (74%) of the HCl salt of the product as a yellow solid. $^1$H NMR (300 MHz, D$_2$O) δ: 9.26 (s, 1H), 7.61 (m, 1H), 7.42 (d, J=3.6 Hz, 1H), 7.26 (m, 1H), 7.19 (m, 1H), 5.00 (br, 2H), 4.70-4.40 (m, 3H). MS m/z: 273 (M+H$^+$).

Step 9

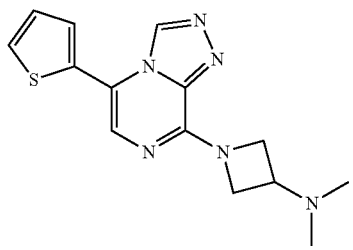 [SMILES: CN(C)C1CN(c2ncc(-c3cccs3)n3cnnc23)C1]

N,N-Dimethyl-1-(5-(thiophen-2-yl)-[1,2,4]triazolo[4,3-a]pyrazin-8-yl)azetidin-3-amine A 50 mL round bottom flask was charged with 1-(5-(thiophen-2-yl)-[1,2,4]triazolo[4,3-a]pyrazin-8-yl)azetidin-3-amine HCl salt (360 mg, 1.2 mmol), 40% aqueous formaldehyde (10 mL), dichloromethane (5 mL), methanol (5 mL) and sodium cyanoborohydride (250 mg, 4.0 mmol) at 0° C. The resulting mixture was stirred at 20° C. overnight. It was then concentrated in vacuo and the residue was extracted with dichloromethane. The organic layer was washed with brine (10 mL), dried over anhydrous Na$_2$SO$_4$, and concentrated in vacuo. The crude product was further purified by flash column chromatography on silica gel with EtOAc and then a 1:5 methanol/dichloromethane, to afford 100 mg of the product as a yellow solid. The product was dissolved in methanol (2 mL) and treated with 3.3 M methanolic HCl (0.5 mL) with stifling. The precipitate was collected by filtration and dried, to afford 70 mg (18%) of the HCl salt of the product as a white solid. $^1$H NMR (300 MHz, D$_2$O) δ: 9.21 (s, 1H), 7.56 (dd, J=5.1, 0.9 Hz, 1H), 7.33 (dd, J=3.6, 0.9 Hz, 1H), 7.20 (s, 1H), 7.13 (dd, J=5.1, 3.6 Hz, 1H), 4.90-4.85 (m, 2H), 4.75-4.70 (m, 2H), 4.43 (m, 1H), 2.92 (s, 6H). MS m/z: 301 (M+H$^+$).

Example 32

1-(5-(Thiophen-2-yl)-[1,2,4]triazolo[4,3-a]pyrazin-8-yl)azetidin-3-amine

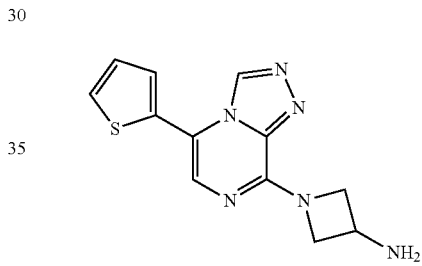

The HCl salt of the title compound was prepared as described in Example 31 step 8. $^1$H NMR (300 MHz, D$_2$O) δ: 9.26 (s, 1H), 7.61 (m, 1H), 7.42 (d, J=3.6 Hz, 1H), 7.26 (m, 1H), 7.19 (m, 1H), 5.00 (br, 2H), 4.70-4.40 (m, 3H). MS m/z: 273 (M+H$^+$).

Example 33

N-Methyl-1-(5-(thiophen-2-yl)-[1,2,4]triazolo[4,3-a]pyrazin-8-yl)azetidin-3-amine

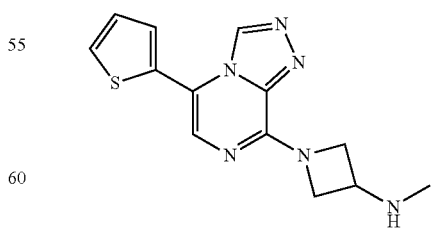

The HCl salt of the title compound was prepared as described in Example 32, except that tert-butyl azetidin-3-yl(methyl)carbamate was substituted for tert-butyl azetidin-3-ylcarbamate in step 7 of that route. $^1$H NMR (300 MHz, D$_2$O)

δ: 9.27 (s, 1H), 7.60 (d, J=4.8 Hz, 1H), 7.42 (d, J=3.6 Hz, 1H), 7.27 (m, 1H), 7.18 (m, 1H), 5.02 (br, 2H), 4.80 (br, 2H), 4.42 (m, 1H), 2.75 (s, 3H). MS m/z: 287 (M+H+).

Example 34

8-(5-Methylhexahydropyrrolo[3,4-c]pyrrol-2(1H)-yl)-5-(thiophen-2-yl)-[1,2,4]triazolo[4,3-a]pyrazine

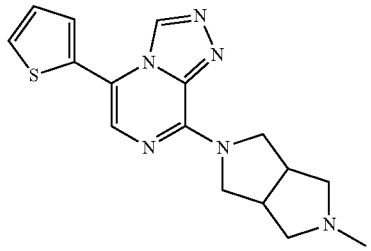 [SMILES: CN1CC2CN(c3ncc(-c4cccs4)n4cnnc34)CC2C1]

The title compound was prepared as described in Example 31, except that tert-butyl hexahydropyrrolo[3,4-c]pyrrole-2(1H)-carboxylate was substituted for tert-butyl azetidin-3-ylcarbamate in step 7 of that route. $^1$H NMR (300 MHz, CDCl$_3$) δ: 9.01 (s, 1H), 7.46 (dd, J=5.2, 1.2 Hz, 1H), 7.43 (s, 1H), 7.32 (dd, J=3.6, 1.2 Hz, 1H), 7.18 (dd, J=5.2, 3.6 Hz, 1H), 4.24 (br, 2H), 3.10 (br, 4H), 2.88 (m, 2H), 2.57 (m, 2H), 2.38 (s, 3H). MS m/z: 327 (M+H+).

Example 35

8-(Hexahydropyrrolo[3,4-c]pyrrol-2(1H)-yl)-5-(thiophen-2-yl)-[1,2,4]triazolo[4,3-a]pyrazine

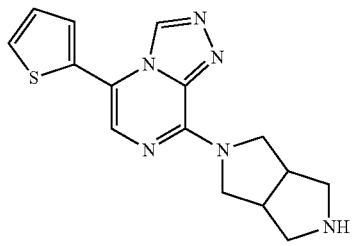 [SMILES: c1csc(-c2cnc(N3CC4CNCC4C3)c3nncn23)c1]

The HCl salt of the title compound was prepared as described in Example 32, except that tert-butyl hexahydropyrrolo[3,4-c]pyrrole-2(1H)-carboxylate was substituted for tert-butyl azetidin-3-ylcarbamate in step 7 of that route. $^1$H NMR (300 MHz, D$_2$O) δ: 9.30 (s, 1H), 7.66 (dd, J=5.1, 1.2 Hz, 1H), 7.48 (dd, J=3.8, 1.2 Hz, 1H), 7.25 (s, 1H), 7.21 (dd, J=5.1, 3.8 Hz, 1H), 4.43 (br, 2H), 4.24 (m, 2H), 3.66 (m, 2H), 3.45 (br, 2H), 3.36 (m, 2H). MS m/z: 313 (M+H+).

SCHEME 4

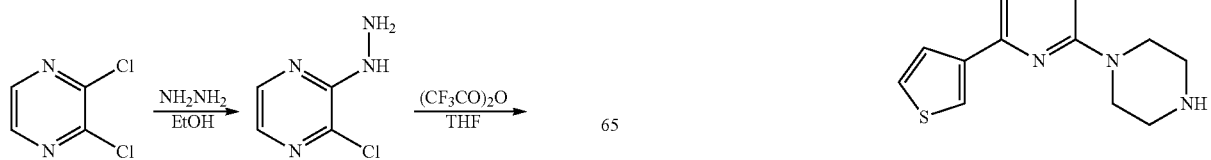

-continued

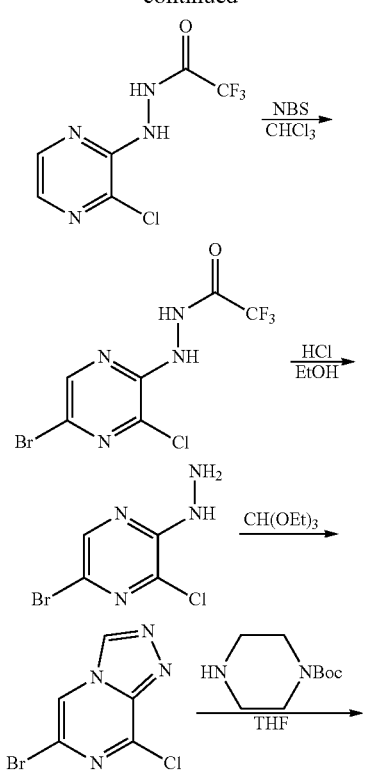

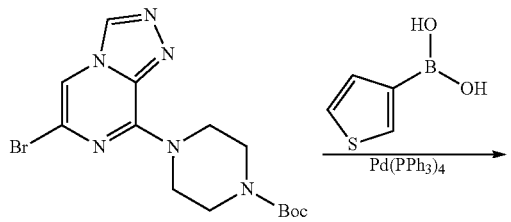

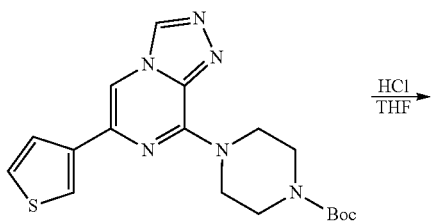

Example 36

8-(piperazin-1-yl)-6-(thiophen-3-yl)-[1,2,4]triazolo[4,3-a]pyrazine

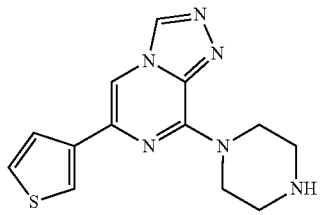 [SMILES: c1cc(-c2cn3cnnc3c(N3CCNCC3)n2)cs1]

Step 1

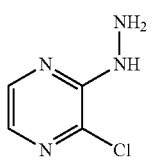

2-Chloro-3-hydrazinylpyrazine

A 100 mL round bottom flask was charged with 2,3-dichloropyrazine (10 g, 67.6 mmol), hydrazine hydrate (6.76 g, 135 mmol) and ethanol (40 mL). The resulting mixture was stirred at reflux for 3 h. Reaction progress was monitored by TLC (EtOAc/petroleum ether=2:1). Work-up: the reaction mixture was cooled to room temperature. The solid was collected by filtration, washed with water (30 mL×2) and dried, to afford 8.4 g (87%) of the product as a yellow solid.

Step 2

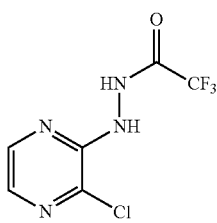 [SMILES: O=C(NNc1nccnc1Cl)C(F)(F)F]

N'-(3-Chloropyrazin-2-yl)-2,2,2-trifluoroacetohydrazide

A 500 mL round bottom flask was charged with 2-chloro-3-hydrazinylpyrazine (5.0 g, 35 mmol) and THF (100 mL). To the above solution was added dropwise a solution of trifluoroacetic anhydride (9.6 g, 45.6 mmol) in THF (125 mL). The resulting solution was stirred for 1 h at 0° C. Reaction progress was monitored by TLC (EtOAc/petroleum ether=1:2). Work-up: the reaction mixture was diluted with water and then extracted with $CH_2Cl_2$ (50 mL×3). The combined organic layers were washed with brine (40 mL), dried over anhydrous $Na_2SO_4$ and concentrated in vacuo to afford 7.56 g (87%) of the product as a yellow solid.

Step 3

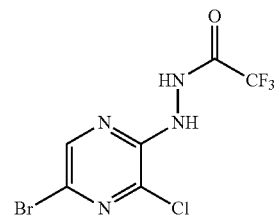 [SMILES: O=C(NNc1ncc(Br)nc1Cl)C(F)(F)F]

N'-(5-Bromo-3-chloropyrazin-2-yl)-2,2,2-trifluoroacetohydrazide

A 500 mL round bottom flask was charged with N'-(3-chloropyrazin-2-yl)-2,2,2-trifluoroacetohydrazide (7.76 g, 32.3 mmol) and $CHCl_3$ (200 mL). To the above solution was added N-bromosuccinimide (8.63 g, 48.5 mmol) at 0° C. The resulting mixture was stirred at room temperature for 1 h. Reaction progress was monitored by TLC (EtOAc/petroleum ether=1:2). Work-up: the reaction mixture was concentrated in vacuo. The residue was purified by flash column chromatography on silica gel with 20% EtOAc in petroleum ether, to afford 2.97 g (29%) of the product as a light yellow solid.

Step 4

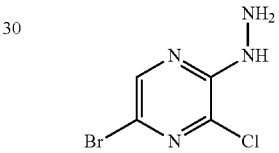

5-Bromo-3-chloro-2-hydrazinylpyrazine

A 250 mL round bottom flask was charged with N'-(5-bromo-3-chloropyrazin-2-yl)-2,2,2-trifluoroacetohydrazide (2.97 g, 9.4 mmol), concentrated HCl (6 mL) and ethanol (60 mL). The resulting mixture was heated at 80° C. for 4 h. The reaction mixture was then allowed to cool to room temperature and neutralized with $Na_2CO_3$. It was then diluted with water and extracted with EtOAc (50 mL×3). The combined organic layers were dried over anhydrous $Na_2SO_4$ and concentrated in vacuo. The residue was further purified by flash column chromatography on silica gel with 20% EtOAc in petroleum ether, to afford 1.24 g (59%) of the product as a yellow solid.

Step 5

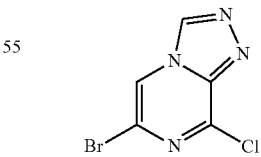

6-Bromo-8-chloro-[1,2,4]triazolo[4,3-a]pyrazine

A 50 mL round bottom flask was charged with 5-bromo-3-chloro-2-hydrazinylpyrazine (1.24 g, 5.5 mmol) and triethyl orthoformate (20 mL). The resulting mixture was stirred at 130° C. for 2 h. Reaction progress was monitored by TLC (EtOAc/petroleum ether=1:2). Work-up: the reaction mixture was diluted with water and extracted with EtOAc (50 mL×3). The combined organic layers were dried over anhydrous Na$_2$SO$_4$ and concentrated in vacuo. The residue was further purified by flash column chromatography on silica gel with 30% EtOAc in petroleum ether, to afford 1.12 g (87%) of the product as a red solid.

Step 6

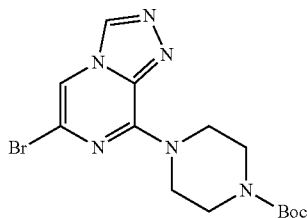 [SMILES: CC(C)(C)OC(=O)N1CCN(c2nc(Br)cn3cnnc23)CC1]

tert-Butyl 4-(6-bromo-[1,2,4]triazolo[4,3-a]pyrazin-8-yl)piperazine-1-carboxylate A 100 mL round bottom flask was charged with 6-bromo-8-chloro-[1,2,4]triazolo[4,3-a]pyrazine (1.11 g, 4.73 mmol), tert-butyl piperazine-1-carboxylate (2.64 g, 14.2 mmol) and THF (50 mL). The resulting mixture was stirred at room temperature for 0.5 h. Reaction progress was monitored by TLC (EtOAc/petroleum ether=1:2). Work-up: the reaction mixture was diluted with water and extracted with EtOAc (50 mL×3). The combined organic layers were dried over anhydrous Na$_2$SO$_4$ and concentrated in vacuo. The residue was further purified by flash column chromatography on silica gel with 20% EtOAc in petroleum ether, to afford 1.62 g (89%) of the product as a yellow solid.

Step 7

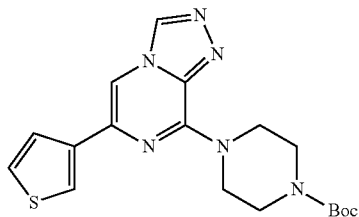 [SMILES: CC(C)(C)OC(=O)N1CCN(c2nc(-c3ccsc3)cn3cnnc23)CC1]

tert-Butyl 4-(6-(thiophen-3-yl)-[1,2,4]triazolo[4,3-a]pyrazin-8-yl)piperazine-1-carboxylate A 100 mL round bottom flask was charged with tert-butyl 4-(6-bromo-[1,2,4]triazolo[4,3-a]pyrazin-8-yl)piperazine-1-carboxylate (1.0 g, 2.6 mmol), thiophen-3-ylboronic acid (0.50 g, 3.9 mmol), Pd(PPh$_3$)$_4$ (0.30 g, 0.26 mmol), Cs$_2$CO$_3$ (1.27 g, 3.9 mmol), 1,4-dioxane (25 mL) and water (25 mL). The resulting mixture was refluxed under N$_2$ overnight. Reaction progress was monitored by TLC (EtOAc/petroleum ether=1:2). Work-up: the reaction mixture was extracted with EtOAc (50 mL). The organic solution was washed with brine (40 mL), dried over anhydrous Na$_2$SO$_4$ and concentrated in vacuo. The residue was further purified by flash column chromatography on silica gel with 10% EtOAc in petroleum ether, to afford 1.0 g (99%) of the product as a yellow solid.

Step 8

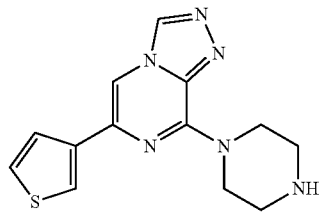 [SMILES: c1cc(-c2cn3cnnc3c(N3CCNCC3)n2)cs1]

8-(piperazin-1-yl)-6-(thiophen-3-yl)-[1,2,4]triazolo[4,3-a]pyrazine

A 100 mL round bottom flask was charged with tert-butyl 4-(6-(thiophen-3-yl)-[1,2,4]triazolo[4,3-a]pyrazin-8-yl)piperazine-1-carboxylate (0.95 g, 2.46 mmol) and THF (25 mL). To the solution was added concentrated HCl (12 mL) and the resulting slurry was refluxed for 15 min. Work-up: the reaction mixture was then allowed to cool to room temperature. The white precipitate was collected by filtration, washed with ethyl ether (20 mL) and dried, to afford 0.78 g (98%) of the HCl salt of the product as a white crystal. $^1$H NMR (300 MHz, D$_2$O) δ: 8.86 (s, 1H), 7.72 (s, 1H), 7.64 (dd, J=2.1, 0.9 Hz, 1H), 7.34 (dd, J=3.9, 2.1 Hz, 1H), 7.18 (dd, J=3.9, 0.9 Hz, 1H), 4.21 (t, J=3.8 Hz, 4H), 3.28 (t, J=3.9 Hz, 4H). MS m/z: 287 (M+H$^+$).

Example 37

8-(4-Methylpiperazin-1-yl)-6-(thiophen-3-yl)-[1,2,4]triazolo[4,3-a]pyrazine

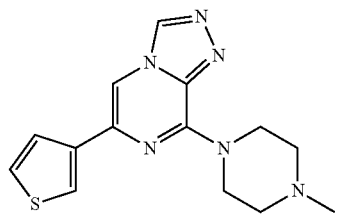 [SMILES: CN1CCN(c2nc(-c3ccsc3)cn3cnnc23)CC1]

The title compound was prepared as described in Example 36, except that N-methylpiperazine was substituted for tert-butyl piperazine-1-carboxylate in step 6 of that route. $^1$H NMR (300 MHz, CDCl$_3$) δ: 8.74 (s, 1H), 7.85 (dd, J=3.0, 1.5 Hz, 1H), 7.74 (s, 1H), 7.43 (dd, J=5.1, 1.5 Hz, 1H), 7.39 (dd, J=5.1, 3.0 Hz, 1H), 4.47 (br, 4H), 2.61 (t, J=5.1 Hz, 4H), 2.37 (s, 3H). MS m/z: 301 (M+H$^+$).

Example 38

8-(4-Methylpiperazin-1-yl)-6-(thiophen-2-yl)-[1,2,4]triazolo[4,3-a]pyrazine

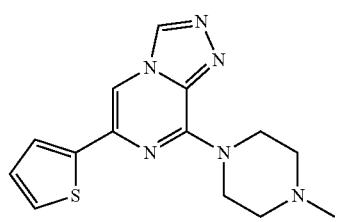 [SMILES: CN1CCN(c2nc(-c3cccs3)cn3cnnc23)CC1]

The title compound was prepared as described in Example 37, except that thiophen-2-ylboronic acid was substituted for thiophen-3-ylboronic acid in step 7 of that route. $^1$H NMR (300 MHz, CDCl$_3$) δ: 8.73 (s, 1H), 7.78 (s, 1H), 7.45 (dd, J=3.6, 1.2 Hz, 1H), 7.35 (dd, J=5.1, 1.2 Hz, 1H), 7.09 (dd, J=5.1, 3.6 Hz, 1H), 4.45 (br, 4H), 2.60 (t, J=5.1 Hz, 4H), 2.37 (s, 3H). MS m/z: 301 (M+H$^+$).

Example 39

8-(piperazin-1-yl)-6-(thiophen-2-yl)-[1,2,4]triazolo[4,3-a]pyrazine

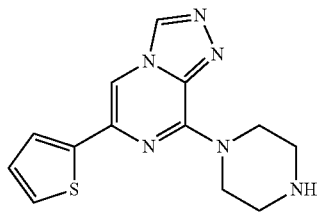 [SMILES: c1csc(-c2cn3cnnc3c(N3CCNCC3)n2)c1]

The HCl salt of the title compound was prepared as described in Example 36, except that thiophen-2-ylboronic acid was substituted for thiophen-3-ylboronic acid in step 7 of that route. $^1$H NMR (300 MHz, DMSO-d$_6$) δ: 9.57 (br, 1H), 9.32 (s, 1H), 8.54 (s, 1H), 7.64 (d, J=3.0 Hz, 1H), 7.61 (d, J=3.6 Hz, 1H), 7.17 (dd, J=3.6, 3.0 Hz, 1H), 4.54 (br, 4H), 3.32 (br, 4H). MS m/z: 287 (M+H$^+$).

Example 40

8-(4-Methylpiperazin-1-yl)-6-(thiophen-2-ylmethyl)-[1,2,4]triazolo[4,3-a]pyrazine

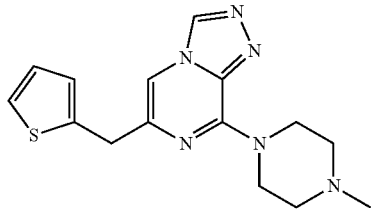 [SMILES: CN1CCN(c2nc(Cc3cccs3)cn3cnnc23)CC1]

The title compound was prepared as described in Example 27, except that tert-butyl 4-(6-bromo-[1,2,4]triazolo[4,3-a]pyrazin-8-yl)piperazine-1-carboxylate (prepared as described in Example 36 steps 1-6) was substituted for tert-butyl 4-(5-bromo-[1,2,4]triazolo[4,3-a]pyrazin-8-yl)piperazine-1-carboxylate in step 1 of that route. $^1$H NMR (300 MHz, CDCl$_3$) δ: 8.61 (s, 1H), 7.23 (s, 1H), 7.20 (dd, J=5.1, 0.9 Hz, 1H), 6.97-6.93 (m, 2H), 4.47 (br, 4H), 4.06 (s, 2H), 2.65 (t, J=5.1 Hz, 4H), 2.41 (s, 3H). MS m/z: 315 (M+H$^+$).

Example 41

8-(4-Methylpiperazin-1-yl)-6-(thiophen-3-ylmethyl)-[1,2,4]triazolo[4,3-a]pyrazine

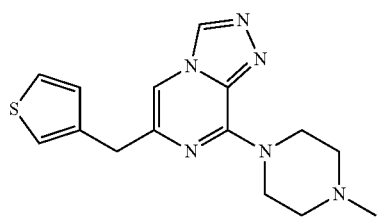 [SMILES: CN1CCN(c2nc(Cc3ccsc3)cn3cnnc23)CC1]

The title compound was prepared as described in Example 40, except that 3-bromothiophene was substituted for thiophene in step 4 of that route. $^1$H NMR (300 MHz, CDCl$_3$) δ: 8.60 (s, 1H), 7.30 (dd, J=5.1, 3.0 Hz, 1H), 7.11 (m, 2H), 7.04 (dd, J=5.1, 0.9 Hz, 1H), 4.46 (br, 4H), 3.89 (s, 2H), 2.66 (t, J=5.1 Hz, 4H), 2.42 (s, 3H). MS m/z: 315 (M+H$^+$).

SCHEME 5

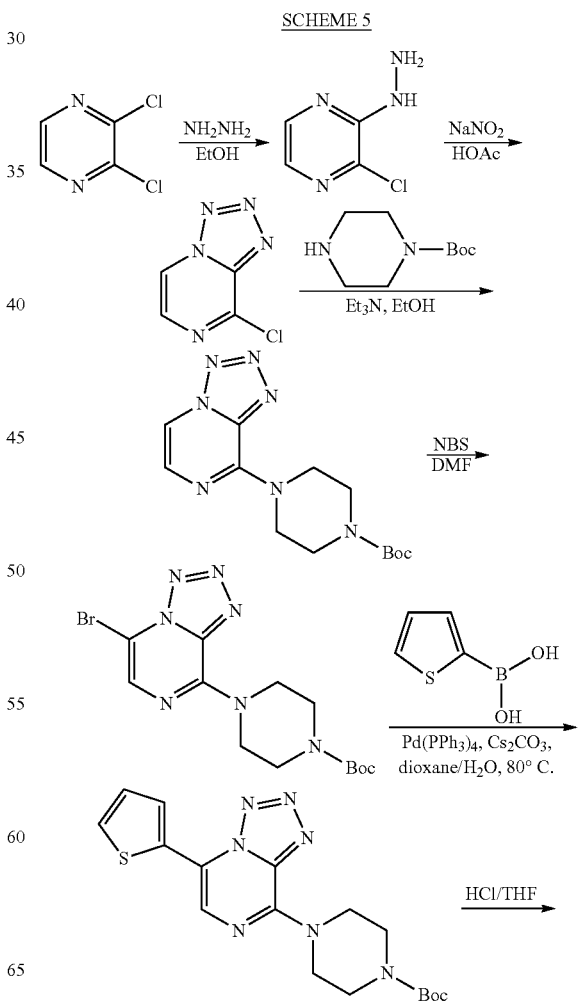

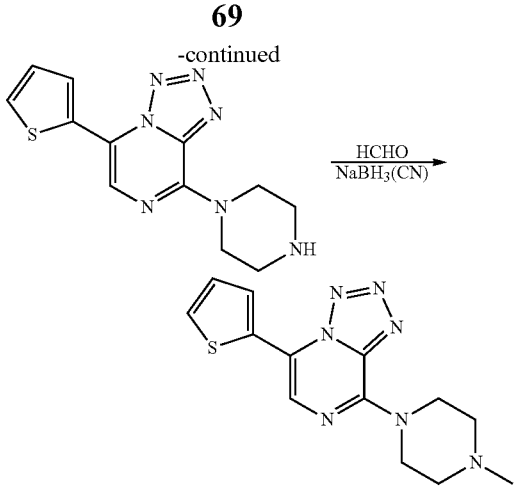

Example 42

8-(4-Methylpiperazin-1-yl)-5-(thiophen-2-yl)tetrazolo[1,5-a]pyrazine

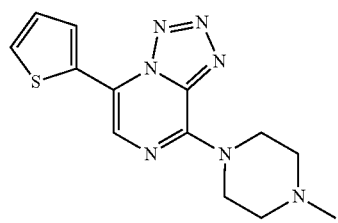 [SMILES: CN1CCN(c2ncc(-c3cccs3)n3nnnc23)CC1]

Step 1

2-Chloro-3-hydrazinylpyrazine

A 5 L round bottom flask was charged with 2,3-dichloropyrazine (1000 g, 6.7 mol), hydrazine monohydrate (700 g, 14 mol) and absolute EtOH (2 L). The resulting solution was refluxed under N₂ overnight. Work-up: the resulting crystalline solid was collected by filtration, washed with EtOH (1 L), and dried to afford 880 g (90%) of the product as a yellow solid.

Step 2

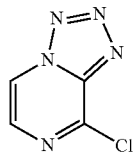

8-Chlorotetrazolo[1,5-a]pyrazine

A 2 L round bottom flask was charged with 2-chloro-3-hydrazinylpyrazine (440 g, 3.0 mol) and CH₃COOH (500 mL). To the above was added dropwise a solution of NaNO₂ (220 g, 3.2 mol) in water (200 mL) at 10° C. The resulting mixture was stirred at 10° C. for 1 h. Work-up: the resulting crystalline solid was collected by filtration, washed with EtOH (200 mL), and dried to afford 350 g (73%) of the product as a red solid.

Step 3

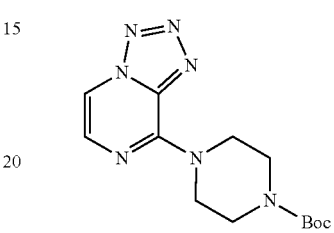

tert-Butyl 4-(tetrazolo[1,5-a]pyrazin-8-yl)piperazine-1-carboxylate

A 3 L round bottom flask was charged with 8-chlorotetrazolo[1,5-a]pyrazine (350 g, 2.3 mol), tert-butyl piperazine-1-carboxylate (420 g, 2.3 mol), triethylamine (460 g, 4.5 mol), and EtOH (2 L). The mixture was heated at reflux for 1 h. Work-up: the reaction mixture was concentrated in vacuo. The residue was mixed with saturated aqueous NaHCO₃ (1 L) and then extracted with CH₂Cl₂ (1 L×3). The combined organic layers were dried over anhydrous Na₂SO₄ and concentrated in vacuo. The residue was further purified by flash column chromatography on silica gel with 8% EtOAc in CH₂Cl₂ (containing 2% Et₃N), to afford 630 g (91%) of the product as a white solid. MS m/z: 306 (M+H⁺).

Step 4

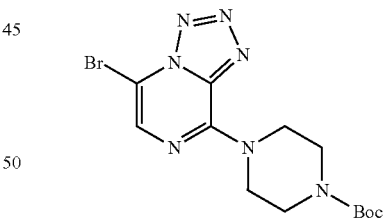

tert-Butyl 4-(5-bromotetrazolo[1,5-a]pyrazin-8-yl)piperazine-1-carboxylate

A 3 L round bottom flask was charged with tert-butyl 4-(tetrazolo[1,5-a]pyrazin-8-yl)piperazine-1-carboxylate (500 g, 1.6 mol) and DMF (2 L). To the above was added N-bromosuccinimide (320 g, 1.8 mol) in portions at 10° C. The resulting mixture was stirred at 10° C. for 0.5 h. Work-up: the reaction mixture was poured into water (3 L). The resulting crystalline solid was collected by filtration, washed with water (300 mL), and dried to afford 500 g (79%) of the product as a red solid. MS m/z: 384 (M+H⁺).

Step 5

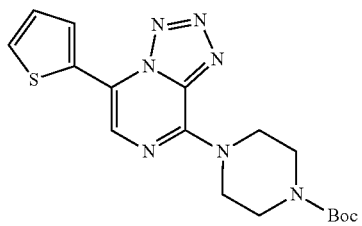 [SMILES: CC(C)(C)OC(=O)N1CCN(c2ncc(-c3cccs3)n3nnnc23)CC1]

tert-Butyl 4-(5-(thiophen-2-yl)tetrazolo[1,5-a]
pyrazin-8-yl)piperazine-1-carboxylate A 1 L round bottom flask was charged with tert-butyl 4-(5-bromotetrazolo[1,5-a]pyrazin-8-yl)piperazine-1-carboxylate (50 g, 0.13 mol), thiophene-2-boronic acid (22 g, 0.17 mol), tetrakis(triphenylphosphine)palladium(0) (7.5 g, 6.5 mmol), $Cs_2CO_3$ (51 g, 0.16 mol), 1,4-dioxane (600 mL) and $H_2O$ (240 mL). After the air was purged by bubbling $N_2$ into the solution, the resulting solution was stirred at 80° C. under $N_2$ for 10 h. Work-up: the reaction mixture was concentrated in vacuo. The residue was purified by flash column chromatography on silica gel eluted with $CH_2Cl_2$, and then crystallized from methanol, to afford 35 g (70%) of the product as a yellow solid. MS m/z: 388 (M+H$^+$).

Step 6

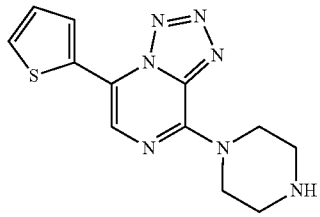

8-(piperazin-1-yl)-5-(thiophen-2-yl)tetrazolo[1,5-a]
pyrazine HCl salt

A 1 L round bottom flask was charged with tert-butyl 4-(5-(thiophen-2-yl)tetrazolo[1,5-a]pyrazin-8-yl)piperazine-1-carboxylate (210 g, 0.54 mol) and THF (400 mL). To this solution was added concentrated HCl (40 mL) dropwise in an ice-water bath. The resulting solution was stirred at reflux for 0.5 h. Reaction progress was monitored by TLC (MeOH/$CH_2Cl_2$=1:10). Work-up: the resulting crystalline solid was collected by filtration, washed with EtOH (200 mL), and dried to afford 139 g (79%) of the product as a yellow solid. MS m/z: 288 (M+H$^+$).

Step 7

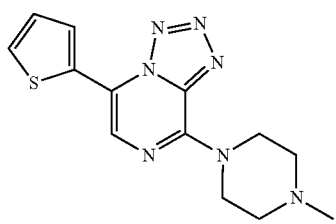 [SMILES: CN1CCN(c2ncc(-c3cccs3)n3nnnc23)CC1]

8-(4-Methylpiperazin-1-yl)-5-(thiophen-2-yl)tetra-
zolo[1,5-a]pyrazine

A 2 L round bottom flask was charged with 8-(piperazin-1-yl)-5-(thiophen-2-yl)tetrazolo[1,5-a]pyrazine HCl salt (139 g, 0.429 mol), HCHO (38% aqueous solution, 50 mL), $NaBH_3(CN)$ (90.7 g, 1.44 mol), $CH_2Cl_2$ (500 mL), and MeOH (200 mL). The resulting solution was stirred at room temperature for 0.5 h. Work-up: the reaction mixture was poured into saturated aqueous $NaHCO_3$ and extracted with $CH_2Cl_2$ (500 mL×3). The combined organic layers were dried over anhydrous $Na_2SO_4$ and concentrated in vacuo. The residue was further purified by flash column chromatography on silica gel with 1-10% MeOH in $CH_2Cl_2$, to afford 122 g (94%) of the product as a yellow solid. $^1$H NMR (300 MHz, CDCl$_3$) δ: 8.00 (m, 2H), 7.45 (dd, J=5.1, 1.2 Hz, 1H), 7.20 (dd, J=5.1, 3.6 Hz, 1H), 4.39 (br, 4H), 2.60 (t, J=5.1 Hz, 4H), 2.37 (s, 3H). MS m/z: 302 (M+H$^+$).

Example 43

8-(piperazin-1-yl)-5-(thiophen-2-yl)tetrazolo[1,5-a]
pyrazine

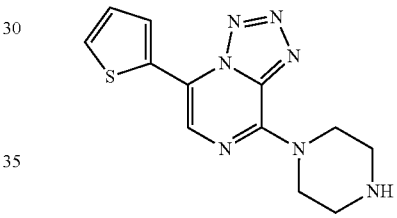

The HCl salt of the title compound was prepared as described in Example 42 step 6. $^1$H NMR (300 MHz, D$_2$O) δ: 7.70 (s, 1H), 7.59 (dd, J=3.8, 1.0 Hz, 1H), 7.47 (dd, J=5.1, 1.0 Hz, 1H), 7.04 (dd, J=5.1, 3.8 Hz, 1H), 4.24 (t, J=5.2 Hz, 4H), 3.32 (t, J=5.4 Hz, 4H). MS m/z: 288 (M+H$^+$).

Example 44

8-(4-Methylpiperazin-1-yl)-5-(thiophen-3-yl)tetra-
zolo[1,5-a]pyrazine

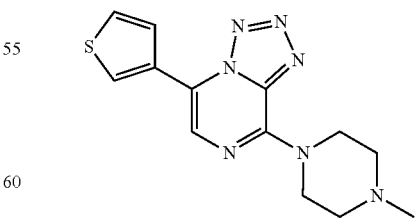

The title compound was prepared as described in Example 42, except that thiophene-3-boronic acid was substituted for thiophene-2-boronic acid in step 5 of that route. $^1$H NMR (300 MHz, CHCl$_3$) δ: 8.41 (dd, J=3.0, 1.2 Hz, 1H), 8.00 (s, 1H), 7.63 (dd, J=5.2, 1.2 Hz, 1H), 7.48 (dd, J=5.2, 3.0 Hz, 1H), 4.39 (br, 4H), 2.60 (t, J=5.0 Hz, 4H), 2.37 (s, 3H). MS m/z: 302 (M+H⁺).

Example 45

8-(piperazin-1-yl)-5-(thiophen-3-yl)tetrazolo[1,5-a]pyrazine

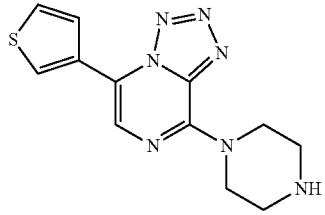

The HCl salt of the title compound was prepared as described in Example 44 step 6. ¹H NMR (300 MHz, DMSO-d₆/D₂O) δ: 8.27 (dd, J=3.0, 1.5 Hz, 1H), 8.02 (s, 1H), 7.62 (dd, J=5.1, 1.5 Hz, 1H), 7.58 (dd, J=5.1, 3.0 Hz, 1H), 4.36 (t, J=5.1 Hz, 4H), 3.29 (t, J=5.1 Hz, 4H). MS m/z: 288 (M+H⁺).

SCHEME 6

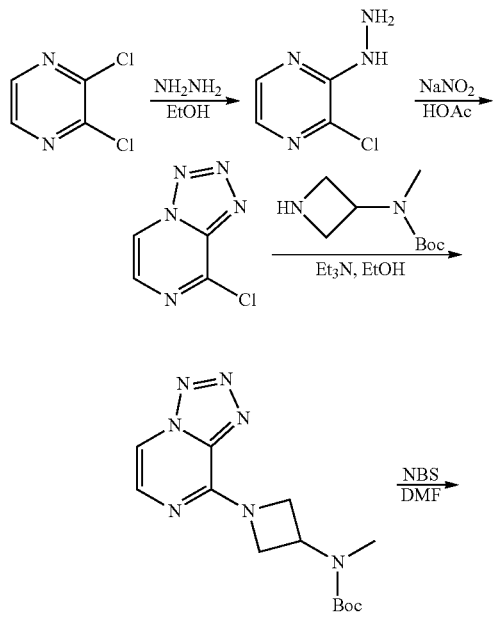

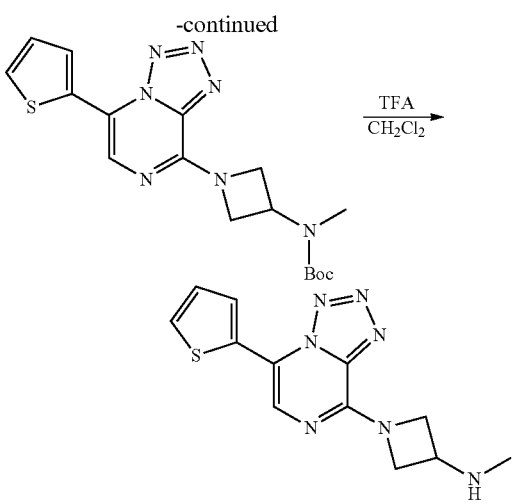

Example 46

N-methyl-1-(5-(thiophen-2-yl)tetrazolo[1,5-a]pyrazin-8-yl)azetidin-3-amine

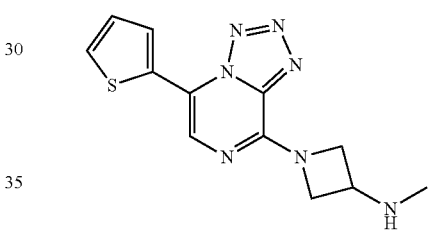

Step 1-2

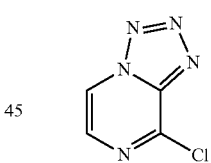

8-Chlorotetrazolo[1,5-a]pyrazine

The title compound was prepared as described in Example 42 steps 1-2.

Step 3

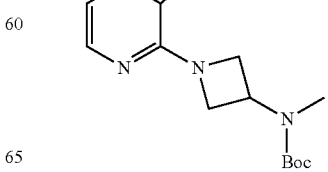

tert-Butyl methyl(1-(tetrazolo[1,5-a]pyrazin-8-yl)azetidin-3-yl)carbamate

A 2 L round bottom flask was charged with 8-chlorotetrazolo[1,5-a]pyrazine (100 g, 0.64 mol), triethylamine (195 g, 1.93 mol) and ethanol (1 L). To the above was added tert-butyl azetidin-3-yl(methyl)carbamate hydrochloride (146 g, 0.66 mol) at 25° C. The resulting mixture was stirred at 25° C. for 1 h. Work-up: the resulting crystalline solid was collected by filtration, washed with ethanol (200 mL), and dried to afford 176 g (91%) of the product as a white solid. MS m/z: 306 (M+H$^+$).
Step 4

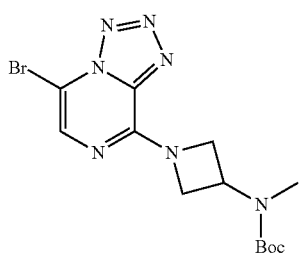 [SMILES: CN(C(=O)OC(C)(C)C)C1CN(c2ncc(Br)n3nnnc23)C1]

tert-Butyl (1-(5-bromotetrazolo[1,5-a]pyrazin-8-yl)azetidin-3-yl)(methyl)carbamate A 3 L round bottom flask was charged with tert-butyl methyl(1-(tetrazolo[1,5-a]pyrazin-8-yl)azetidin-3-yl)carbamate (200 g, 0.66 mol) and DMF (1 L). To the above was added N-bromosuccinimide (117 g, 0.66 mol) in portions at 10° C. The resulting mixture was stirred at 10° C. for 0.5 h. Work-up: the reaction mixture was poured into water (3 L). The resulting crystalline solid was collected by filtration, washed with water (500 mL), and dried to afford 200 g (79%) of the product as a white solid.
Step 5

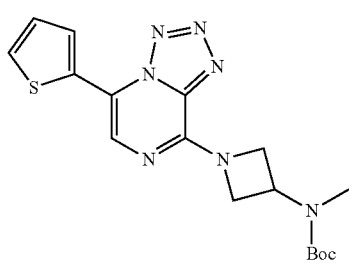 [SMILES: CN(C(=O)OC(C)(C)C)C1CN(c2ncc(-c3cccs3)n3nnnc23)C1]

tert-Butyl methyl(1-(5-(thiophen-2-yl)tetrazolo[1,5-a]pyrazin-8-yl)azetidin-3-yl)carbamate A 3 L round bottom flask was charged with tert-butyl (1-(5-bromotetrazolo[1,5-a]pyrazin-8-yl)azetidin-3-yl)(methyl)carbamate (50 g, 0.13 mol), thiophene-2-boronic acid (22 g, 0.17 mol), tetrakis(triphenylphosphine)palladium(0) (5.0 g, 4.3 mmol), Cs$_2$CO$_3$ (50 g, 0.15 mol), 1,4-dioxane (1.5 L) and water (500 mL). After the air was purged by bubbling N$_2$ into the solution, the resulting solution was stirred at 80° C. under N$_2$ for 14 h. Work-up: the reaction mixture was concentrated in vacuo. The residue was purified by flash column chromatography on silica gel with 0-25% ethyl acetate in CH$_2$Cl$_2$, and then crystallized from methanol, to afford 35 g (70%) of the product as a yellow solid.
Step 6

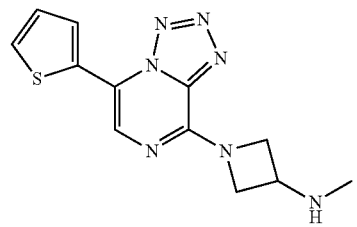 [SMILES: CNC1CN(c2ncc(-c3cccs3)n3nnnc23)C1]

N-methyl-1-(5-(thiophen-2-yl)tetrazolo[1,5-a]pyrazin-8-yl)azetidin-3-amine

A 2 L round bottom flask was charged with tert-butyl methyl(1-(5-(thiophen-2-yl)tetrazolo[1,5-a]pyrazin-8-yl)azetidin-3-yl)carbamate (50 g, 0.13 mol) and dichloromethane (500 mL). To the solution was added trifluoroacetic acid (100 mL). The resulting slurry was stirred at room temperature for 2.5 h. Work-up: the reaction mixture was concentrated in vacuo. The residue was suspended in water (500 L) and treated with solid Na$_2$CO$_3$ (pH 10-11, there was un-dissolved Na$_2$CO$_3$ remaining). The solid was collected by filtration, re-suspended in water (500 mL×2) with stirring to remove Na$_2$CO$_3$. It was further washed with EtOH (500 mL), and dried to afford 27 g (73%) of the product as a yellow solid.
$^1$H NMR (400 MHz, DMSO-d$_6$) δ: 8.19 (s, 1H), 7.96 (dd, J=4.0, 0.8 Hz, 1H), 7.76 (dd, J=4.8, 0.8 Hz, 1H), 7.27 (dd, J=4.8, 4.0 Hz, 1H), 4.60 (br, 2H), 4.18 (br, 2H), 3.73 (m, 1H), 2.43 (br, 1H), 2.29 (s, 3H). MS m/z: 288 (M+H$^+$).

Example 47

(S)-N-methyl-1-(5-(thiophen-2-yl)tetrazolo[1,5-a]pyrazin-8-yl)pyrrolidin-3-amine

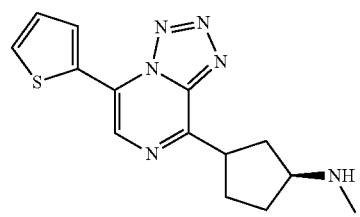 [SMILES: CN[C@H]1CCC(c2ncc(-c3cccs3)n3nnnc23)C1]

The HCl salt of the title compound was prepared as described in Example 42, except that (S)-tert-butyl methyl (pyrrolidin-3-yl)carbamate was substituted for N-BOC-piperazine in step 3 of that route. $^1$H NMR (300 MHz, D$_2$O) δ: 7.52 (s, 1H), 7.49-7.45 (m, 2H), 7.04 (dd, J=5.2, 3.8 Hz, 1H), 4.10 (br, 1H), 3.99 (m, 3H), 3.83 (br, 1H), 2.75 (s, 3H), 2.53 (m, 1H), 2.26 (m, 1H). MS m/z: 302 (M+H⁺).

Example 48

(R)-N-methyl-1-(5-(thiophen-2-yl)tetrazolo[1,5-a]pyrazin-8-yl)pyrrolidin-3-amine

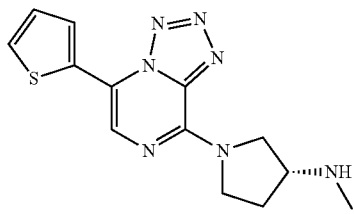 [SMILES: CN[C@@H]1CCN(c2ncc(-c3cccs3)n3nnnc23)C1]

The HCl salt of the title compound was prepared as described in Example 42, except that (R)-tert-butyl methyl (pyrrolidin-3-yl)carbamate was substituted for N-BOC-piperazine in step 3 of that route. ¹H NMR (300 MHz, D₂O) δ: 7.64 (s, 1H), 7.61-7.58 (m, 2H), 7.17 (t, J=3.3 Hz, 1H), 4.23 (br, 1H), 4.12 (m, 3H), 3.94 (br, 1H), 2.88 (s, 3H), 2.66 (m, 1H), 2.39 (m, 1H). MS m/z: 302 (M+H⁺).

Example 49

1-(5-(5-Bromothiophen-2-yl)tetrazolo[1,5-a]pyrazin-8-yl)-N-methylazetidin-3-amine

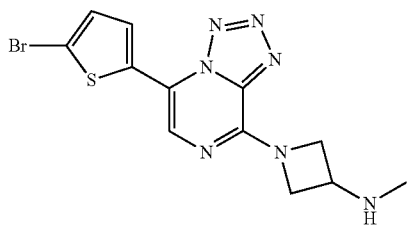 [SMILES: CNC1CN(c2ncc(-c3ccc(Br)s3)n3nnnc23)C1]

The title compound was prepared as described in Example 46, except that 2-(5-bromothiophen-2-yl)-4,4,5,5-tetramethyl-1,3,2-dioxaborolane was substituted for thiophene-2-boronic acid in step 5 of that route. ¹H NMR (300 MHz, DMSO-d₆) δ: 8.25 (s, 1H), 7.78 (d, J=4.2 Hz, 1H), 7.39 (d, J=4.2 Hz, 1H), 4.61 (br, 2H), 4.17 (br, 2H), 3.74 (m, 1H), 2.29 (s, 3H). MS m/z: 366 (M+H⁺).

SCHEME 7

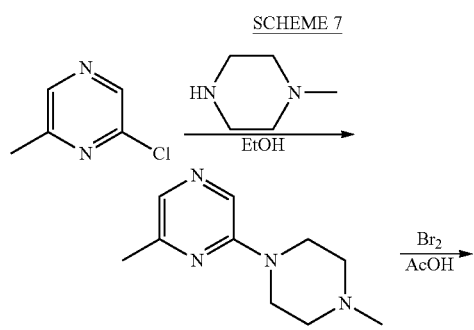

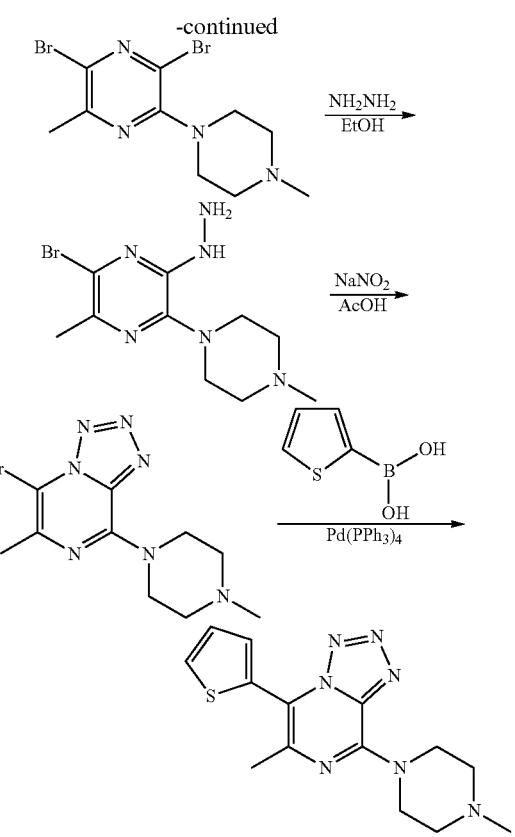

Example 50

6-Methyl-8-(4-methylpiperazin-1-yl)-5-(thiophen-2-yl)tetrazolo[1,5-a]pyrazine

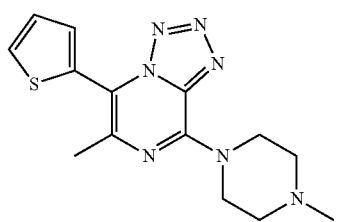 [SMILES: Cc1nc(N2CCN(C)CC2)c2nnnn2c1-c1cccs1]

Step 1

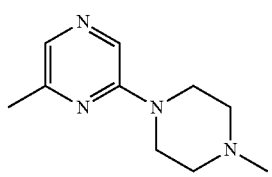

2-Methyl-6-(4-methylpiperazin-1-yl)pyrazine

A 250 mL round bottom flask was charged with 2-chloro-6-methylpyrazine (4.0 g, 0.031 mol), 1-methylpiperazine (12.4 g, 0.125 mol) and EtOH (100 mL). The resulting mixture was heated at reflux overnight. Work-up: the solvent was evaporated. The residue was mixed with saturated aqueous NaHCO$_3$ (100 mL) and then extracted with CH$_2$Cl$_2$ (100 mL×3). The combined organic layers were dried over anhydrous Na$_2$SO$_4$ and concentrated in vacuo. The residue was further purified by flash column chromatography on silica gel with 4% MeOH in CH$_2$Cl$_2$, to afford 2.7 g (45%) of the product as a white solid. MS m/z: 193 (M+H$^+$).

Step 2

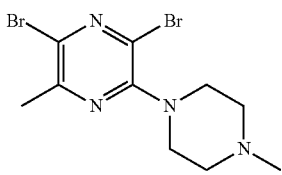

2,6-Dibromo-3-methyl-5-(4-methylpiperazin-1-yl)pyrazine

A 100 mL round bottom flask was charged with 2-methyl-6-(4-methylpiperazin-1-yl)pyrazine (2.0 g, 0.010 mol) and CH$_3$COOH (40 mL). To the above was added Br$_2$ (3.49 g, 0.022 mol) in portions at room temperature. The resulting mixture was stirred at room temperature for 2 h. Work-up: the reaction mixture was diluted with water (200 mL) and then extracted with EtOAc (100 mL×3). The combined organic layers were dried over anhydrous Na$_2$SO$_4$ and concentrated in vacuo. The residue was purified by flash column chromatography on silica gel with 4% MeOH in CH$_2$Cl$_2$, to afford 2.5 g (69%) of the product as a white solid. MS m/z: 349, 351, 353 (M+H$^+$).

Step 3

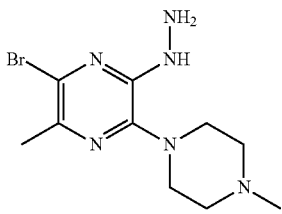

2-Bromo-6-hydrazinyl-3-methyl-5-(4-methylpiperazin-1-yl)pyrazine

A 100 mL round bottom flask was charged with 2,6-dibromo-3-methyl-5-(4-methylpiperazin-1-yl)pyrazine (2.0 g, 5.7 mmol), hydrazine hydrate (3.5 g, 0.065 mol) and absolute EtOH (30 mL). The resulting solution was refluxed under N$_2$ atmosphere overnight. Work-up: the solvent was evaporated. The residue was washed with EtOH (10 mL) and dried, to afford 0.92 g (54%) of the product as a yellow solid.

Step 4

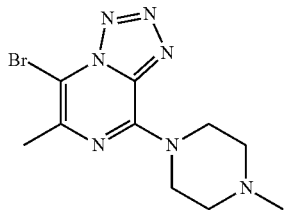

5-Bromo-6-methyl-8-(4-methylpiperazin-1-yl)tetrazolo[1,5-a]pyrazine

A 25 mL round bottom flask was charged with 2-bromo-6-hydrazinyl-3-methyl-5-(4-methylpiperazin-1-yl)pyrazine (0.92 g, 3.0 mmol) and CH$_3$COOH (2 mL). To the above was added dropwise a solution of NaNO$_2$ (0.32 g, 4.6 mmol) in water (2 mL) at 10° C. The resulting mixture was stirred at 10° C. for 1 h. Work-up: the reaction mixture was diluted with saturated aqueous NaHCO$_3$ (100 mL) and then extracted with CH$_2$Cl$_2$ (100 mL×3). The combined organic layers were dried over anhydrous Na$_2$SO$_4$ and concentrated in vacuo. The residue was purified by flash column chromatography on silica gel with 4% MeOH in CH$_2$Cl$_2$, to afford 0.72 g (75%) of the product as a white solid. MS m/z: 312 (M+H$^+$).

Step 5

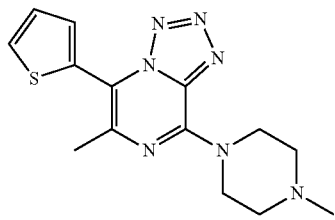 [SMILES: Cc1nc(N2CCN(C)CC2)c2nnnn2c1-c1cccs1]

6-Methyl-8-(4-methylpiperazin-1-yl)-5-(thiophen-2-yl)tetrazolo[1,5-a]pyrazine

A 50 mL round bottom flask was charged with 5-bromo-6-methyl-8-(4-methylpiperazin-1-yl)tetrazolo[1,5-a]pyrazine (0.72 g, 2.3 mmol), thiophene-2-boronic acid (0.46 g, 3.6 mmol), tetrakis(triphenylphosphine)palladium(0) (0.30 g, 0.26 mmol), Cs$_2$CO$_3$ (1.2 g, 3.7 mmol), 1,4-dioxane (12 mL) and water (6 mL). After the air was purged by bubbling N$_2$ into the solution, the resulting mixture was stirred at 100° C. under N$_2$ atmosphere overnight. Work-up: the reaction mixture was poured into 0.1 M HCl (40 mL) and washed with EtOAc (50 mL×2). The aqueous layer was then basified with solid NaHCO$_3$ and extracted with CH$_2$Cl$_2$ (50 mL×3). The combined CH$_2$Cl$_2$ layers were dried over anhydrous Na$_2$SO$_4$ and concentrated in vacuo. The residue was purified by flash column chromatography on silica gel with 5% MeOH in CH$_2$Cl$_2$, to afford 165 mg (23%) of the product as a white solid. $^1$H NMR (300 MHz, CDCl$_3$) δ: 7.59 (dd, J=5.1, 1.2 Hz, 1H), 7.38 (dd, J=3.6, 1.2 Hz, 1H), 7.21 (dd, J=5.1, 3.6 Hz, 1H), 4.40 (br, 4H), 2.60 (t, J=5.1 Hz, 4H), 2.47 (s, 3H), 2.38 (s, 3H). MS m/z: 316 (M+H$^+$).

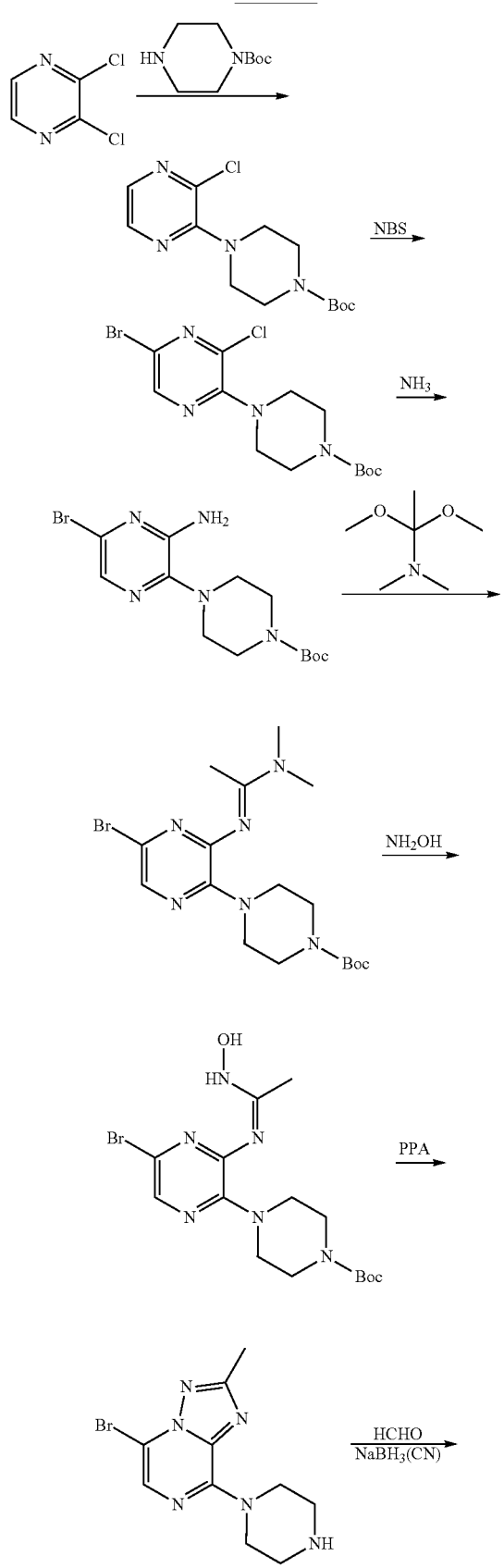
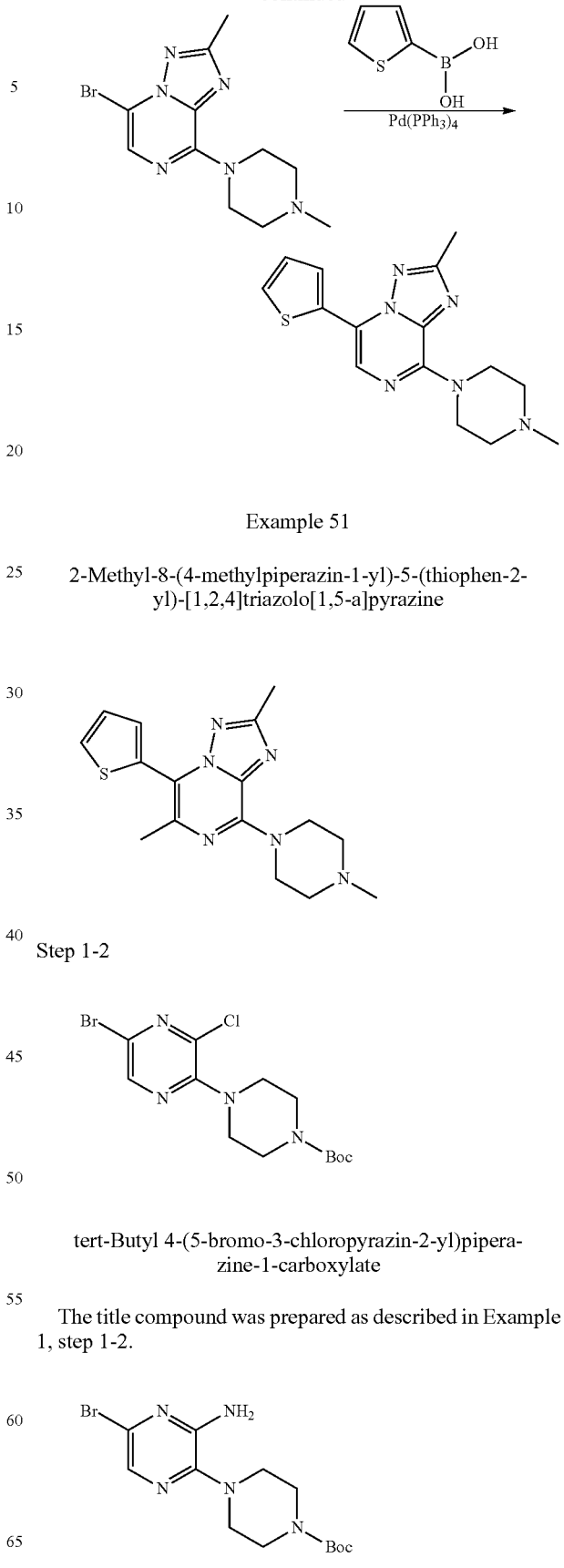
Example 51
2-Methyl-8-(4-methylpiperazin-1-yl)-5-(thiophen-2-yl)-[1,2,4]triazolo[1,5-a]pyrazine
Step 1-2
tert-Butyl 4-(5-bromo-3-chloropyrazin-2-yl)piperazine-1-carboxylate
The title compound was prepared as described in Example 1, step 1-2.

Step 3 tert-Butyl 4-(3-amino-5-bromopyrazin-2-yl)piperazine-1-carboxylate

A 300 mL pressure vessel was charged with tert-butyl 4-(5-bromo-3-chloropyrazin-2-yl)piperazine-1-carboxylate (5.0 g, 13 mmol) and concentrated ammonium hydroxide (60 mL). The vessel was sealed and the reaction mixture was magnetically stirred at 120° C. for 12 h. After the reaction mixture was cooled to room temperature, the vessel was opened and the resulting mixture was poured into water (100 mL) and extracted with CH$_2$Cl$_2$ (50 mL×3). The combined organic layers were dried over anhydrous Na$_2$SO$_4$ and concentrated in vacuo. The residue was purified by flash column chromatography on silica gel with 3% EtOAc in CH$_2$Cl$_2$ (containing 2% Et$_3$N), to afford 2.4 g (51%) of the product as a white solid. MS m/z: 358 (M+H$^+$).

Step 4

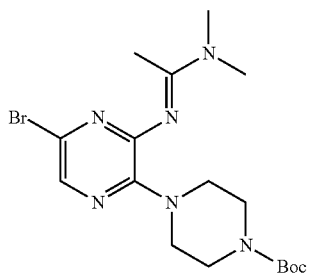 [SMILES: C/C(=N\c1nc(Br)cnc1N1CCN(C(=O)OC(C)(C)C)CC1)N(C)C]

tert-Butyl 4-(5-bromo-3-((1-(dimethylamino)ethylidene)amino)pyrazin-2-yl)piperazine-1-carboxylate A 100 mL round bottom flask was charged with tert-butyl 4-(3-amino-5-bromopyrazin-2-yl)piperazine-1-carboxylate (1.0 g, 2.8 mmol), N,N-dimethylacetamide dimethyl acetal (0.44 g, 3.3 mmol) and toluene (20 mL). The mixture was heated at reflux for 11 h. Work-up: the solvent was evaporated to dryness. The product was used in the next step without further purification.

Step 5

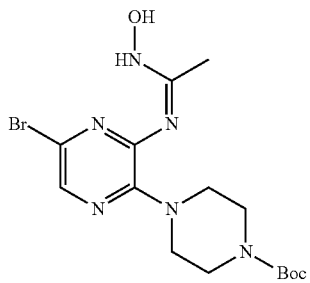 [SMILES: C/C(=N/c1nc(Br)cnc1N1CCN(C(=O)OC(C)(C)C)CC1)NO]

tert-Butyl 4-(5-bromo-3-((1-(hydroxyamino)ethylidene)amino)pyrazin-2-yl)piperazine-1-carboxylate A 100 mL round bottom flask was charged with tert-butyl 4-(5-bromo-3-((1-(dimethylamino)ethylidene)amino)pyrazin-2-yl)piperazine-1-carboxylate (2.8 g, 6.6 mmol) and methanol (25 mL). To the above solution was added hydroxylamine hydrochloride (0.76 g, 10.9 mmol) in one portion. The mixture was stirred at room temperature for 16 h. Work-up: the solvent was evaporated. The resulting crystalline solid was washed with water and collected by filtration. The solid was washed with ethanol (100 mL) and dried, to afford 2.3 g (84%) of the product as a white solid.

Step 6

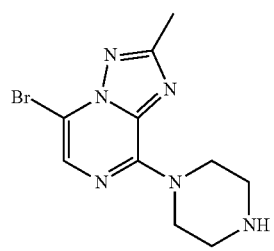 [SMILES: Cc1nc2c(N3CCNCC3)ncc(Br)n2n1]

5-Bromo-2-methyl-8-(piperazin-1-yl)-[1,2,4]triazolo[1,5-a]pyrazine

In a 50 mL round bottom flask, tert-butyl 4-(5-bromo-3-((1-(hydroxyamino)ethylidene)amino)pyrazin-2-yl)piperazine-1-carboxylate (2.3 g, 5.5 mmol) was treated with polyphosphoric acid (10 g) at 50° C. for 1 h then at 75° C. for 1.75 h. Work-up: the mixture was carefully neutralized with saturated aqueous NaHCO$_3$ (300 mL) and extracted with CH$_2$Cl$_2$ (100 mL×3). The combined organic layers were dried over anhydrous Na$_2$SO$_4$ and concentrated in vacuo. The residue was purified by flash column chromatography on silica gel with 5% EtOAc in CH$_2$Cl$_2$ (containing 2% Et$_3$N), to afford 1.0 g (61%) of the product as a white solid. MS m/z: 297 (M+H$^+$).

Step 7

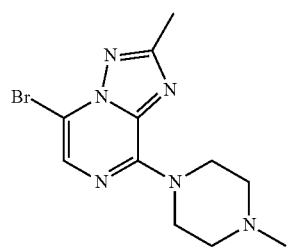 [SMILES: Cc1nc2c(N3CCN(C)CC3)ncc(Br)n2n1]

5-Bromo-2-methyl-8-(4-methylpiperazin-1-yl)-[1,2,4]triazolo[1,5-a]pyrazine

A 100 mL round bottom flask was charged with 5-bromo-2-methyl-8-(piperazin-1-yl)-[1,2,4]-triazolo[1,5-a]pyrazine (0.5 g, 1.7 mmol), CH$_2$Cl$_2$ (20 mL), MeOH (10 mL), 40% aqueous formaldehyde (2 mL) and NaBH$_3$(CN) (0.5 g, 8.0 mmol). The resulting solution was stirred at room temperature for 0.5 h. Work-up: the reaction mixture was poured into saturated aqueous NaHCO$_3$ and extracted with CH$_2$Cl$_2$ (50 mL×3). The combined organic layers were dried over anhydrous Na$_2$SO$_4$ and concentrated in vacuo. The residue was purified by flash column chromatography on silica gel with 1-10% MeOH in CH$_2$Cl$_2$, to afford 0.4 g (76%) of the product as a yellow solid. MS m/z: 311 (M+H$^+$).

Step 8

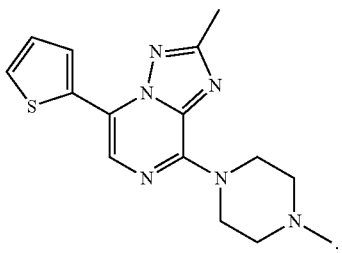 [SMILES: Cc1nc2c(N3CCN(C)CC3)ncc(-c3cccs3)n2n1]

2-Methyl-8-(4-methylpiperazin-1-yl)-5-(thiophen-2-yl)-[1,2,4]triazolo[1,5-a]pyrazine A 50 mL round bottom flask was charged with 5-bromo-2-methyl-8-(4-methylpiperazin-1-yl)-[1,2,4]triazolo[1,5-a]pyrazine (0.40 g, 1.3 mmol), thiophene-2-boronic acid (0.25 g, 2.0 mmol), tetrakis(triphenylphosphine)palladium(0) (0.15 g, 0.13 mmol), $Cs_2CO_3$ (0.65 g, 2.0 mmol), 1,4-dioxane (20 mL) and water (5 mL). After the oxygen was purged by bubbling $N_2$ into the solution, the reaction solution was stirred at 80° C. under $N_2$ for 10 h. Work-up: the reaction mixture was poured into saturated aqueous $NaHCO_3$ and extracted with $CH_2Cl_2$ (50 mL×3). The combined organic layers were dried over anhydrous $Na_2SO_4$ and concentrated in vacuo. The residue was purified by flash column chromatography on silica gel with 1-10% MeOH in $CH_2Cl_2$, to afford 0.26 g (64%) of the product as a white solid. It was converted into the corresponding HCl salt by treating with methanolic HCl solution. $^1$H NMR (300 MHz, $D_2O$) δ: 7.50 (s, 1H), 7.49 (dd, J=3.9, 1.2 Hz, 1H), 7.45 (dd, J=5.1, 1.2 Hz, 1H), 7.03 (dd, J=5.1, 3.9 Hz, 1H), 4.68 (m, 2H), 3.51 (m, 2H), 3.23 (m, 2H), 3.07 (m, 2H), 2.83 (s, 3H), 2.36 (s, 3H). MS m/z: 315 (M+H$^+$).

Example 52

2-Methyl-8-(piperazin-1-yl)-5-(thiophen-2-yl)-[1,2,4]triazolo[1,5-a]pyrazine

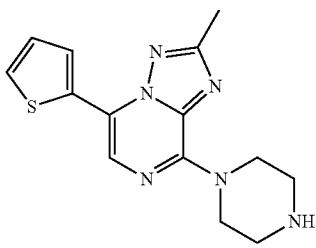 [SMILES: Cc1nc2c(N3CCNCC3)ncc(-c3cccs3)n2n1]

The HCl salt of the title compound was prepared as described in Example 51, except that step 7 of that route was skipped. $^1$H NMR (300 MHz, $D_2O$) δ: 7.40 (dd, J=5.1, 0.9 Hz, 1H), 7.37 (dd, J=3.9, 0.9 Hz, 1H), 7.35 (s, 1H), 6.96 (dd, J=5.1, 3.9 Hz, 1H), 3.90 (t, J=5.4 Hz, 4H), 3.24 (t, J=5.4 Hz, 4H), 2.30 (s, 3H). MS m/z: 301 (M+H$^+$).

Example 53

2-Methyl-8-(4-methylpiperazin-1-yl)-5-(thiophen-3-yl)-[1,2,4]triazolo[1,5-a]pyrazine

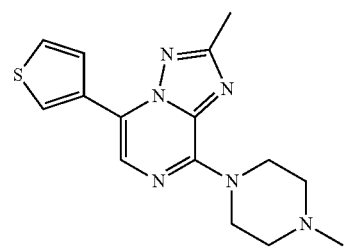 [SMILES: Cc1nc2c(N3CCN(C)CC3)ncc(-c3ccsc3)n2n1]

The HCl salt of the title compound was prepared as described in Example 51, except that thiophene-3-boronic acid was substituted for thiophene-2-boronic acid in step 8 of that route. $^1$H NMR (300 MHz, $D_2O$) δ: 7.92 (m, 1H), 7.40-7.36 (m, 2H), 7.24 (dd, J=5.1, 0.9 Hz, 1H), 4.62 (m, 2H), 3.51 (m, 2H), 3.24 (m, 2H), 3.05 (m, 2H), 2.83 (s, 3H), 2.34 (s, 3H). MS m/z: 315 (M+H$^+$).

Example 54

2-Methyl-8-(piperazin-1-yl)-5-(thiophen-3-yl)-[1,2,4]triazolo[1,5-a]pyrazine

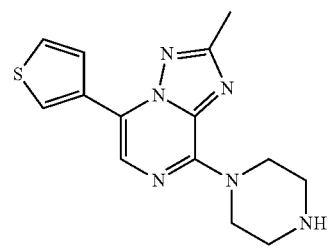 [SMILES: Cc1nc2c(N3CCNCC3)ncc(-c3ccsc3)n2n1]

The HCl salt of the title compound was prepared as described in Example 53, except that step 7 of that route was skipped. $^1$H NMR (300 MHz, $D_2O$) δ: 7.89 (m, 1H), 7.40-7.35 (m, 2H), 7.22 (dd, J=5.1, 0.6 Hz, 1H), 3.94 (m, 4H), 3.28 (m, 4H), 2.34 (s, 3H). MS m/z: 301 (M+H$^+$).

SCHEME 9

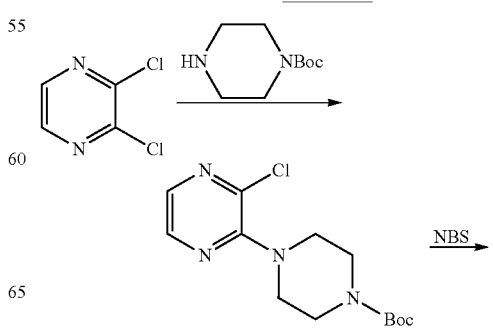

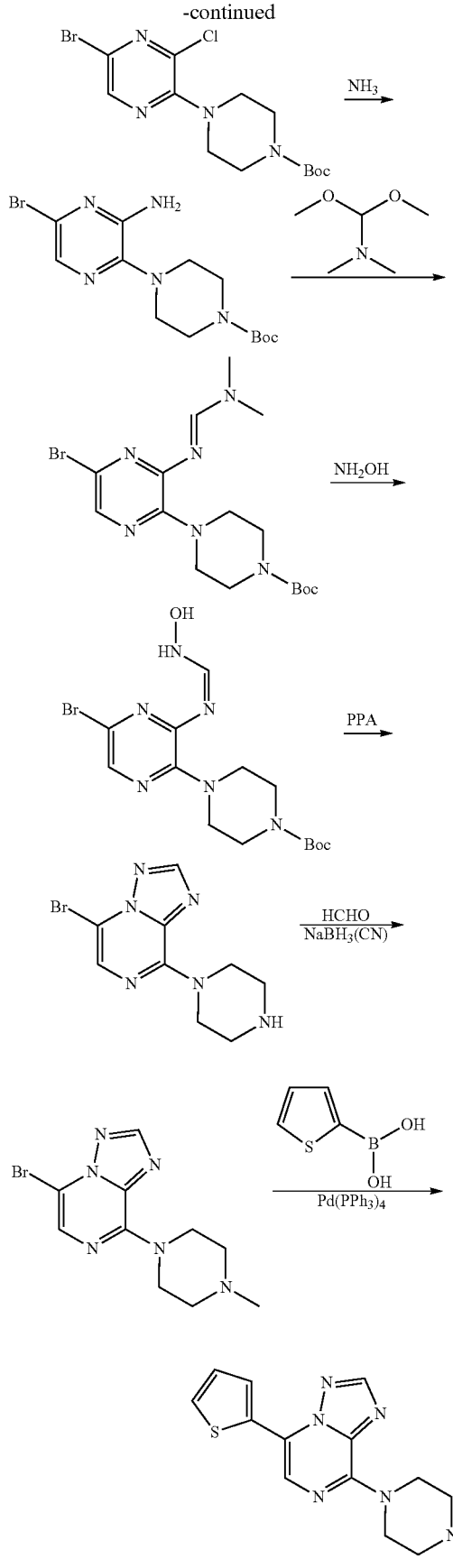

Example 55

8-(4-Methylpiperazin-1-yl)-5-(thiophen-2-yl)-[1,2,4]triazolo[1,5-a]pyrazine

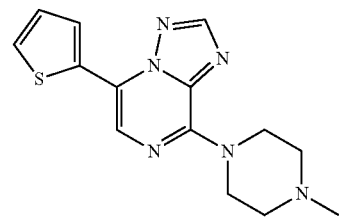 [SMILES: CN1CCN(c2ncc(-c3cccs3)n3ncnc23)CC1]

The HCl salt of the title compound was prepared as described in Example 51, except that N,N-dimethylformamide dimethyl acetal was substituted for N,N-dimethylacetamide dimethyl acetal in step 4 of that route. $^1$H NMR (300 MHz, D$_2$O) δ: 8.14 (s, 1H), 7.42-7.38 (m, 3H), 6.96 (dd, J=4.8, 0.9 Hz, 1H), 4.70 (m, 2H), 3.49 (m, 2H), 3.22 (m, 2H), 3.01 (m, 2H), 2.81 (s, 3H). MS m/z: 301 (M+H$^+$).

Example 56

8-(piperazin-1-yl)-5-(thiophen-2-yl)-[1,2,4]triazolo[1,5-a]pyrazine

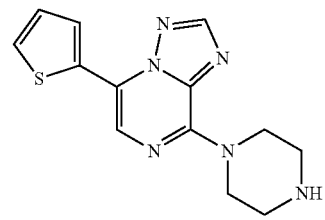 [SMILES: c1csc(-c2cnc(N3CCNCC3)c3ncnn23)c1]

The HCl salt of the title compound was prepared as described in Example 55, except that step 7 of that route was skipped. $^1$H NMR (300 MHz, CD$_3$OD) δ: 8.50 (s, 1H), 8.11 (s, 1H), 8.02 (dd, J=3.9, 1.2 Hz, 1H), 7.58 (dd, J=5.1, 1.2 Hz, 1H), 7.21 (dd, J=5.1, 3.9 Hz, 1H), 4.40 (t, J=5.1 Hz, 4H), 3.22 (t, J=5.1 Hz, 4H). MS m/z: 287 (M+H$^+$).

SCHEME 10

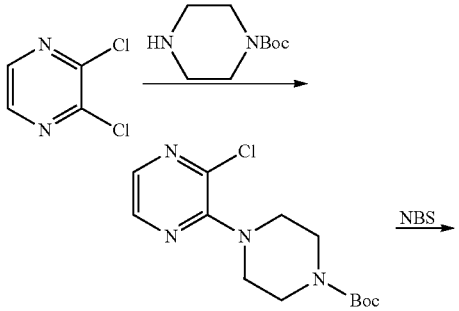

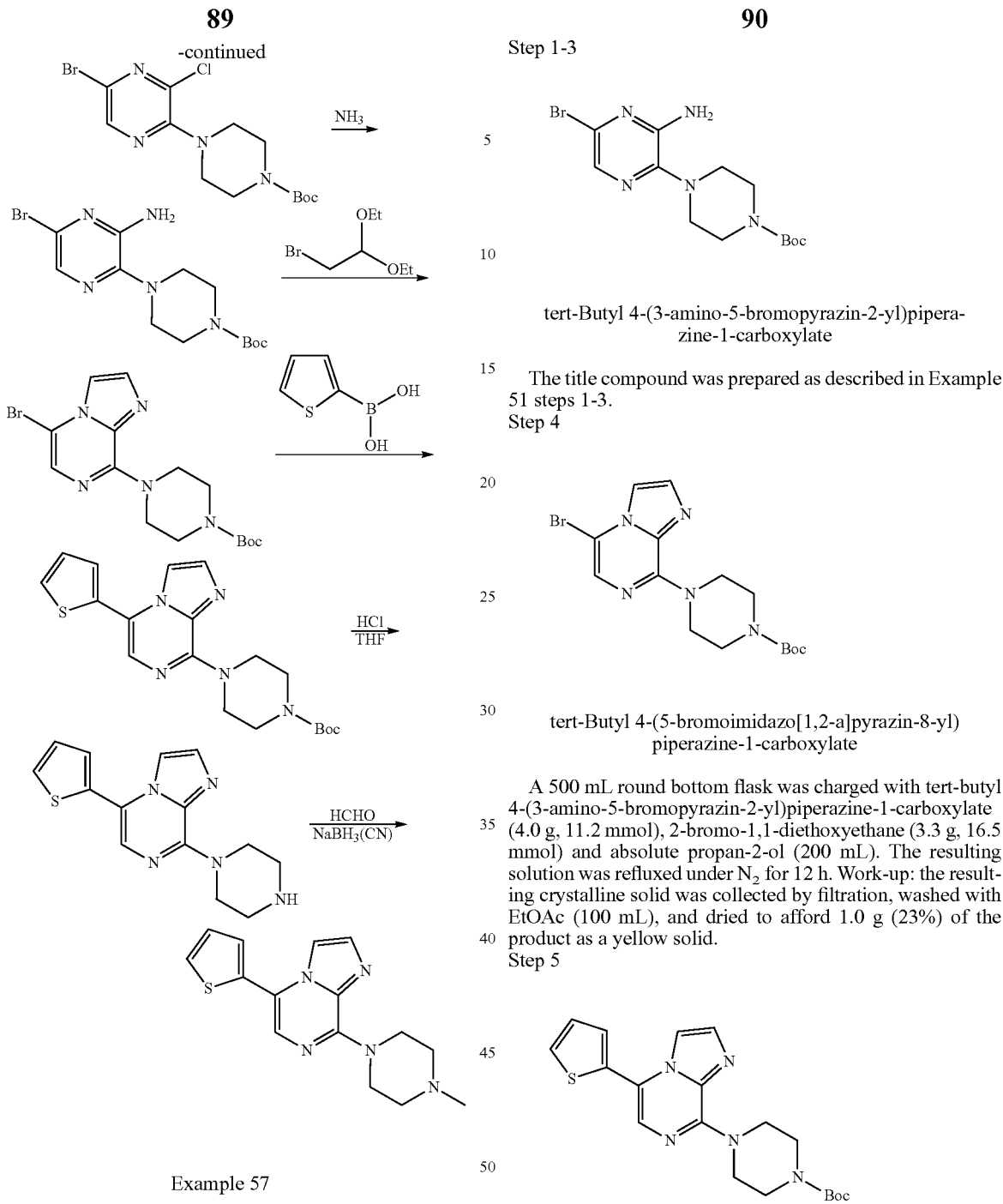

Step 1-3 tert-Butyl 4-(3-amino-5-bromopyrazin-2-yl)piperazine-1-carboxylate

The title compound was prepared as described in Example 51 steps 1-3.

Step 4 tert-Butyl 4-(5-bromoimidazo[1,2-a]pyrazin-8-yl)piperazine-1-carboxylate

A 500 mL round bottom flask was charged with tert-butyl 4-(3-amino-5-bromopyrazin-2-yl)piperazine-1-carboxylate (4.0 g, 11.2 mmol), 2-bromo-1,1-diethoxyethane (3.3 g, 16.5 mmol) and absolute propan-2-ol (200 mL). The resulting solution was refluxed under $N_2$ for 12 h. Work-up: the resulting crystalline solid was collected by filtration, washed with EtOAc (100 mL), and dried to afford 1.0 g (23%) of the product as a yellow solid.

Step 5 tert-Butyl 4-(5-(thiophen-2-yl)imidazo[1,2-a]pyrazin-8-yl)piperazine-1-carboxylate A 100 mL round bottom flask was charged with tert-butyl 4-(5-bromoimidazo[1,2-a]pyrazin-8-yl)piperazine-1-carboxylate (1.0 g, 2.62 mmol), thiophen-2-ylboronic acid (0.50 g, 3.93 mmol), Pd(PPh$_3$)$_2$Cl$_2$ (200 mg, 0.26 mmol), Cs$_2$CO$_3$ (0.60 g, 3.93 mmol) and DMF (30 mL). After air was purged by bubbling $N_2$ into the reaction solution, the reaction mixture was heated at 90° C. for 30 h. Work-up: the reaction mixture was poured into water (150 mL) and extracted with EtOAc (200 mL×3). The combined organic layers were dried over anhydrous Na$_2$SO$_4$ and then concentrated in vacuo. The residue was further purified by flash column chromatography on Example 57

8-(4-Methylpiperazin-1-yl)-5-(thiophen-2-yl)imidazo[1,2-a]pyrazine

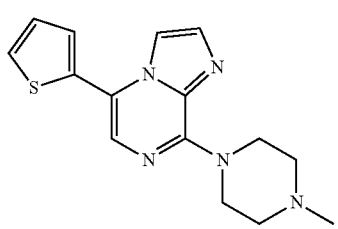 [SMILES: CN1CCN(c2ncc(-c3cccs3)n3ccnc23)CC1]

silica gel with 10% EtOAc in petroleum ether, to afford 0.70 g (72%) of the product as a yellow solid. MS m/z: 386 (M+H⁺).

Step 6

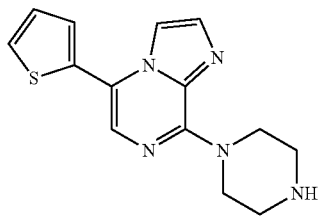

8-(piperazin-1-yl)-5-(thiophen-2-yl)imidazo[1,2-a]pyrazine

A 100 mL round bottom flask was charged with tert-butyl 4-(5-(thiophen-2-yl)imidazo[1,2-a]pyrazin-8-yl)piperazine-1-carboxylate (0.70 g, 1.9 mmol) and THF (35 mL). To the solution was added concentrated HCl (4 mL) dropwise at 0° C. The resulting solution was stirred at reflux for 0.5 h. Reaction progress was monitored by TLC (MeOH/CH$_2$Cl$_2$=1:10). Work-up: the resulting crystalline solid was collected by filtration, washed with EtOH (20 mL), and dried to afford 0.60 g (83%) of the HCl salt of the product as a yellow solid. $^1$H NMR (300 MHz, CD$_3$OD) δ: 8.24 (d, J=1.5 Hz, 1H), 7.96 (d, J=1.5 Hz, 1H), 7.80 (dd, J=5.1, 1.2 Hz, 1H), 7.62 (dd, J=3.9, 1.2 Hz, 1H), 7.60 (s, 1H), 7.32 (dd, J=5.1, 3.6 Hz, 1H), 4.56-4.53 (m, 4H), 3.57-3.53 (br, 4H). MS m/z: 286 (M+H⁺).

Step 7

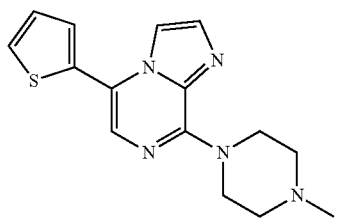 [SMILES: CN1CCN(c2ncc(-c3cccs3)n3ccnc23)CC1]

8-(4-Methylpiperazin-1-yl)-5-(thiophen-2-yl)imidazo[1,2-a]pyrazine

A 100 mL round bottom flask was charged with 8-(piperazin-1-yl)-5-(thiophen-2-yl)imidazo[1,2-a]pyrazine (0.40 g, 1.3 mmol), CH$_2$Cl$_2$ (20 mL), MeOH (10 mL), 40% aqueous HCHO (2 mL) and NaBH$_3$(CN) (0.40 g, 5.2 mmol). The resulting solution was stirred at room temperature for 0.5 h. Work-up: the reaction mixture was diluted with saturated aqueous NaHCO$_3$ and extracted with CH$_2$Cl$_2$ (50 mL×3). The combined CH$_2$Cl$_2$ layers were dried over anhydrous Na$_2$SO$_4$ and concentrated in vacuo. The residue was purified by flash column chromatography on silica gel with 1-10% MeOH in CH$_2$Cl$_2$ to afford 0.30 g (79%) of the product as a yellow solid. It was converted into the corresponding HCl salt by treating with methanolic HCl solution. $^1$H NMR (300 MHz, CD$_3$OD) δ: 8.20 (s, 1H), 7.88 (s, 1H), 7.76 (dd, J=5.1, 0.9 Hz, 1H), 7.62 (s, 1H), 7.59 (dd, J=3.9, 1.2 Hz, 1H), 7.30 (dd, J=5.1, 3.9 Hz, 1H), 5.44-5.30 (br, 2H), 3.72-3.68 (br, 4H), 3.49-3.39 (br, 2H), 3.00 (s, 3H). MS m/z: 300 (M+H⁺).

Example 58

8-(piperazin-1-yl)-5-(thiophen-2-yl)imidazo[1,2-a]pyrazine

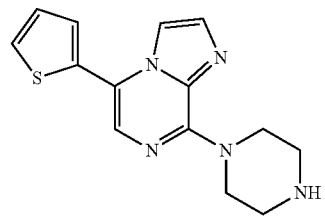 [SMILES: c1csc(-c2cnc(N3CCNCC3)c3nccn23)c1]

The HCl salt of the title compound was prepared as described in Example 57 step 6. $^1$H NMR (300 MHz, CD$_3$OD) δ: 8.24 (d, J=1.5 Hz, 1H), 7.96 (d, J=1.5 Hz, 1H), 7.80 (dd, J=5.1, 1.2 Hz, 1H), 7.62 (dd, J=3.9, 1.2 Hz, 1H), 7.60 (s, 1H), 7.32 (dd, J=5.1, 3.6 Hz, 1H), 4.56-4.53 (m, 4H), 3.57-3.53 (br, 4H). MS m/z: 286 (M+H⁺).

Example 59

8-(4-Methylpiperazin-1-yl)-5-(thiophen-3-yl)imidazo[1,2-a]pyrazine

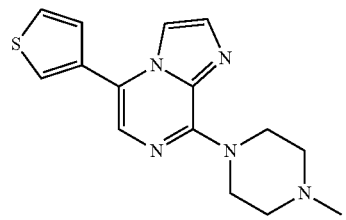 [SMILES: CN1CCN(c2ncc(-c3ccsc3)n3ccnc23)CC1]

The HCl salt of the title compound was prepared as described in Example 57, except that thiophen-3-ylboronic acid was substituted for thiophen-2-ylboronic acid in step 5 of that route. $^1$H NMR (300 MHz, CD$_3$OD) δ: 8.16 (d, J=1.5 Hz, 1H), 8.00 (dd, J=3.0, 1.5 Hz, 1H), 7.97 (d, J=1.2 Hz, 1H), 7.76 (dd, J=4.8, 3.0 Hz, 1H), 7.60 (s, 1H), 7.49 (dd, J=4.8, 0.9 Hz, 1H), 5.30-5.25 (m, 2H), 3.86-3.75 (m, 4H), 3.51-3.47 (m, 2H), 3.01 (s, 3H). MS m/z: 300 (M+H⁺).

Example 60

8-(piperazin-1-yl)-5-(thiophen-3-yl)imidazo[1,2-a]pyrazine

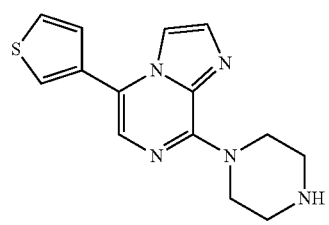 [SMILES: c1cn2c(-c3ccsc3)cnc(N3CCNCC3)c2n1]

93

The HCl salt of the title compound was prepared as described in Example 59 step 6. $^1$H NMR (300 MHz, CD$_3$OD) δ: 8.16 (d, J=1.5 Hz, 1H), 8.00-7.96 (m, 2H), 7.77 (dd, J=4.8, 2.7 Hz, 1H), 7.57 (s, 1H), 7.49 (dd, J=5.1, 1.2 Hz, 1H), 4.55-4.52 (m, 4H), 3.57-3.54 (m, 4H). MS m/z: 286 (M+H$^+$).

SCHEME 11

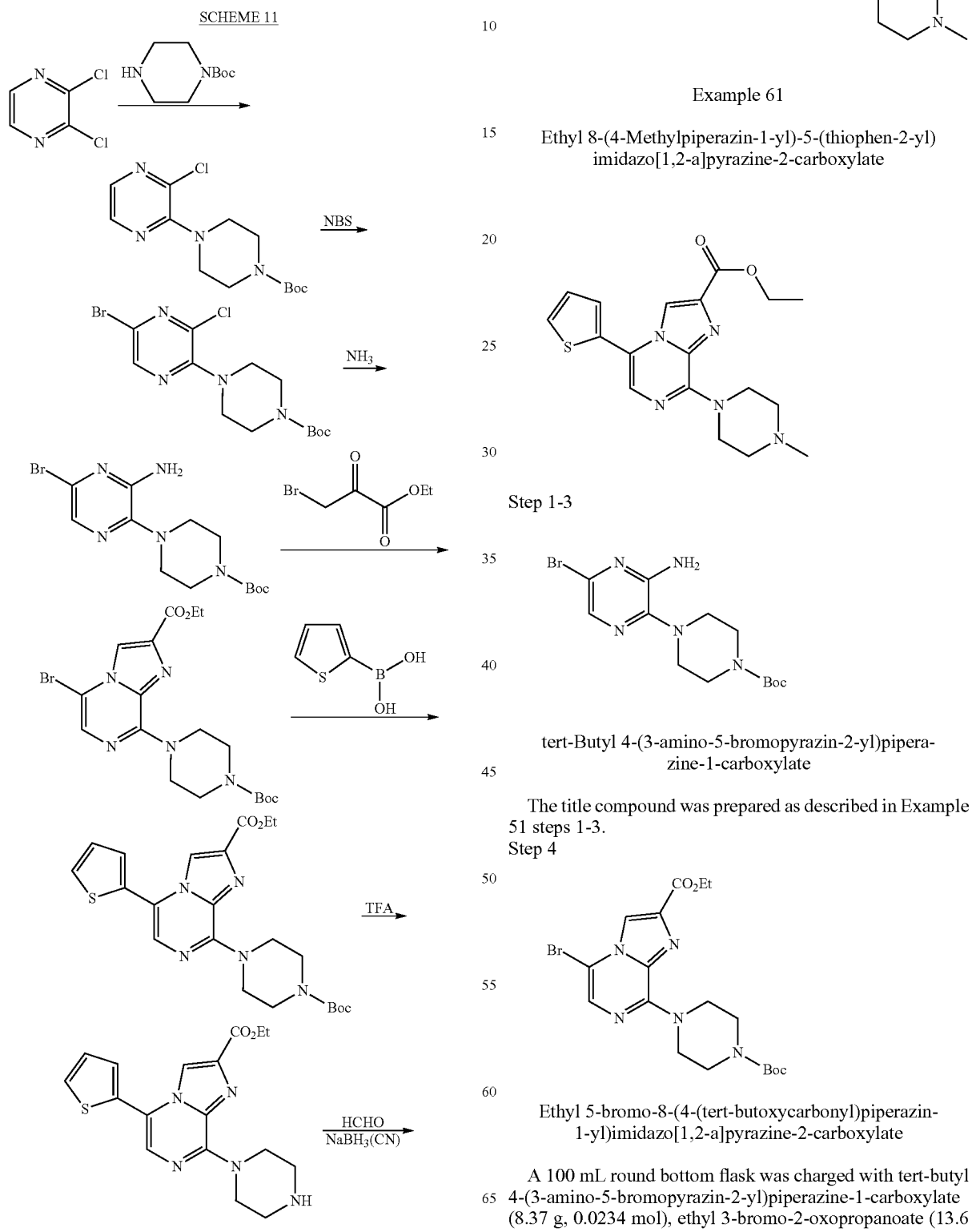

94

-continued

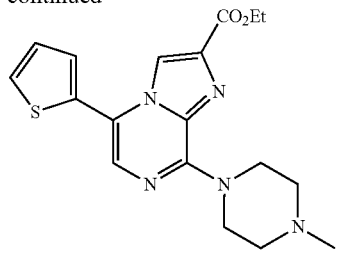

Example 61

Ethyl 8-(4-Methylpiperazin-1-yl)-5-(thiophen-2-yl)imidazo[1,2-a]pyrazine-2-carboxylate Step 1-3 tert-Butyl 4-(3-amino-5-bromopyrazin-2-yl)piperazine-1-carboxylate

The title compound was prepared as described in Example 51 steps 1-3.

Step 4

Ethyl 5-bromo-8-(4-(tert-butoxycarbonyl)piperazin-1-yl)imidazo[1,2-a]pyrazine-2-carboxylate A 100 mL round bottom flask was charged with tert-butyl 4-(3-amino-5-bromopyrazin-2-yl)piperazine-1-carboxylate (8.37 g, 0.0234 mol), ethyl 3-bromo-2-oxopropanoate (13.6 g, 0.070 mol) and EtOH (50 mL). The mixture was stirred at 90° C. for 6 h. Reaction progress was monitored by LC-MS. Work-up: the reaction mixture was filtered. The collected solid was washed with ethyl ether, to afford 5.7 g (56%) of ethyl 5-bromo-8-(piperazin-1-yl)imidazo[1,2-a]pyrazine-2-carboxylate hydrobromide. ¹H NMR (300 MHz, DMSO-d₆) δ: 8.43 (s, 1H), 7.73 (s, 1H), 4.37-4.32 (m, 6H), 3.16 (br, 4H), 1.34 (t, J=6.9 Hz, 3H).

A 250 mL round bottom flask was charged with ethyl 5-bromo-8-(piperazin-1-yl)imidazo[1,2-a]pyrazine-2-carboxylate hydrobromide (6.88 g, 0.0265 mol), di-(tert-butyl) dicarbonate (6.80 g, 0.0318 mol), acetone (80 mL) and water (25 mL). The mixture was stirred at 25° C. for 1 h. Reaction progress was monitored by LC-MS. Work-up: the reaction mixture was filtered. The collected solid was washed with MeOH, to afford 7.0 g (97%) of the product.
Step 5

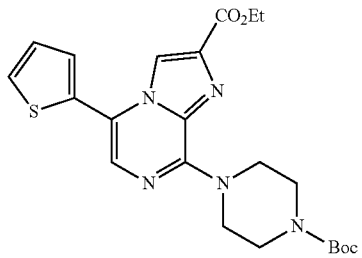

Ethyl 8-(4-(tert-butoxycarbonyl)piperazin-1-yl)-5-(thiophen-2-yl)imidazo[1,2-a]pyrazine-2-carboxylate The title compound was prepared as described in Example 57 step 5, except that ethyl 5-bromo-8-(4-(tert-butoxycarbonyl)piperazin-1-yl)imidazo[1,2-a]pyrazine-2-carboxylate was substituted for tert-butyl 4-(5-bromoimidazo[1,2-a]pyrazin-8-yl)piperazine-1-carboxylate. ¹H NMR (300 MHz, CHCl₃) δ: 8.35 (s, 1H), 7.51 (s, 1H), 7.49 (dd, J=4.8, 1.2 Hz, 1H), 7.37-7.35 (m, 1H), 7.21-7.19 (m, 1H), 4.42 (q, J=7.2 Hz, 2H), 4.34 (br, 4H), 3.60 (br, 4H), 1.49 (s, 9H), 1.40 (t, J=7.2 Hz, 3H).
Step 6

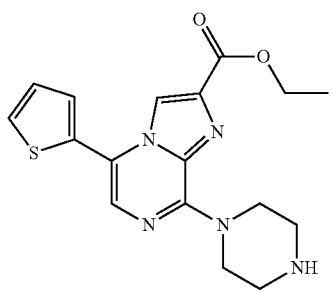

Ethyl 8-(piperazin-1-yl)-5-(thiophen-2-yl)imidazo[1,2-a]pyrazine-2-carboxylate

A 25 mL round bottom flask was charged with ethyl 8-(4-(tert-butoxycarbonyl)piperazin-1-yl)-5-(thiophen-2-yl)imidazo[1,2-a]pyrazine-2-carboxylate (1.13 g, 2.47 mmol), trifluoroacetic acid (5 mL) and CH₂Cl₂ (10 mL). The mixture was stirred at 25° C. for 1 h. Reaction progress was monitored by LC-MS. Work-up: the solvent was evaporated. The residue was mixed with saturated aqueous NaHCO₃ and extracted with EtOAc (30 mL×3). The combined organic layers were dried over anhydrous Na₂SO₄ and concentrated in vacuo. The residue was further purified by flash column chromatography on silica gel with a 1:20 MeOH/CH₂Cl₂, to afford 0.75 g (84%) of the product. ¹H NMR (300 MHz, CD₃OD) δ: 8.40 (s, 1H), 7.69 (dd, J=5.1, 1.2 Hz, 1H), 7.58 (s, 1H), 7.52 (dd, J=3.9, 1.2 Hz, 1H), 7.28 (dd, J=5.1, 3.9 Hz, 1H), 4.54 (t, J=5.1 Hz, 4H), 4.41 (q, J=7.2 Hz, 2H), 3.39 (t, J=5.1 Hz, 4H), 1.38 (t, J=7.2 Hz, 3H). MS m/z: 358 (M+H⁺).
Step 7

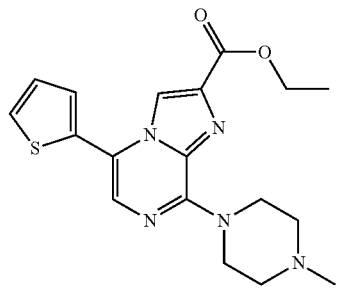 [SMILES: CCOC(=O)c1cn2c(-c3cccs3)cnc(N3CCN(C)CC3)c2n1]

Ethyl 8-(4-methylpiperazin-1-yl)-5-(thiophen-2-yl)imidazo[1,2-a]pyrazine-2-carboxylate A 25 mL round bottom flask was charged with ethyl 8-(piperazin-1-yl)-5-(thiophen-2-yl)imidazo[1,2-a]pyrazine-2-carboxylate (200 mg, 0.56 mmol), MeOH (15 mL), CH₂Cl₂ (15 mL), 40% aqueous formaldehyde (1 mL) and NaBH₃(CN) (250 mg, 3.9 mmol). The mixture was stirred at 25° C. for 1 h. Reaction progress was monitored by LC-MS. Work-up: the solvent was evaporated. The residue was purified by flash column chromatography on silica gel with a 1:20 MeOH/CH₂Cl₂, to afford 150 mg (72%) of the product. ¹H NMR (300 MHz, CDCl₃) δ: 8.33 (s, 1H), 7.50 (s, 1H), 7.48 (dd, J=5.4, 1.2 Hz, 1H), 7.35 (dd, J=3.3, 1.2 Hz, 1H), 7.20 (dd, J=5.4, 3.3 Hz, 1H), 4.43-4.38 (m, 6H), 2.59 (t, J=5.1 Hz, 4H), 1.40 (t, J=6.9 Hz, 3H). MS m/z: 372 (M+H⁺).

Example 62

Ethyl 8-(piperazin-1-yl)-5-(thiophen-2-yl)imidazo[1,2-a]pyrazine-2-carboxylate

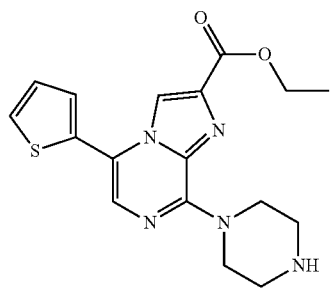

The title compound was prepared as described in Example 61 step 6. ¹H NMR (300 MHz, CD₃OD) δ: 8.40 (s, 1H), 7.69 (dd, J=5.1, 1.2 Hz, 1H), 7.58 (s, 1H), 7.52 (dd, J=3.9, 1.2 Hz, 1H), 7.28 (dd, J=5.1, 3.9 Hz, 1H), 4.54 (t, J=5.1 Hz, 4H), 4.41 (q, J=7.2 Hz, 2H), 3.39 (t, J=5.1 Hz, 4H), 1.38 (t, J=7.2 Hz, 3H). MS m/z: 358 (M+H⁺).

Example 63

Ethyl 5-(furan-2-yl)-8-(4-methylpiperazin-1-yl)imidazo[1,2-a]pyrazine-2-carboxylate

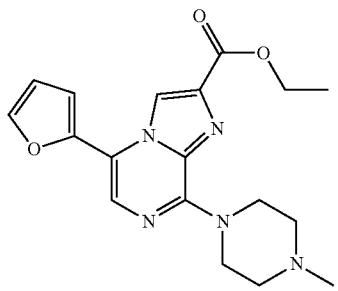

The title compound was prepared as described in Example 61, except that furan-2-ylboronic acid was substituted for thiophen-2-ylboronic acid in step 5 of that route. $^1$H NMR (300 MHz, CDCl$_3$) δ: 8.54 (s, 1H), 7.66 (s, 1H), 7.62 (d, J=1.8 Hz, 1H), 6.70 (d, J=3.3 Hz, 1H), 6.57 (dd, J=3.3, 1.8 Hz, 1H), 4.48-4.40 (m, 6H), 2.60 (t, J=5.4 Hz, 4H), 2.36 (s, 3H), 1.42 (t, J=7.2 Hz, 3H). MS m/z: 356 (M+H$^+$).

Example 64

Ethyl 5-(furan-2-yl)-8-(piperazin-1-yl)imidazo[1,2-a]pyrazine-2-carboxylate

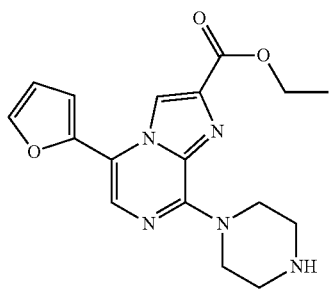 [SMILES: CCOC(=O)c1cn2c(-c3cccs3)cnc(N3CCNCC3)c2n1]

The HCl salt of the title compound was prepared as described in Example 63 step 6. $^1$H NMR (300 MHz, D$_2$O) δ: 8.08 (s, 1H), 7.51 (s, 1H), 7.22 (s, 1H), 6.64 (d, J=3.3 Hz, 1H), 6.50 (dd, J=3.6, 1.8 Hz, 1H), 4.26-4.16 (m, 6H), 3.33 (t, J=4.8 Hz, 4H), 1.27 (t, J=7.2 Hz, 3H). MS m/z: 342 (M+H$^+$).

SCHEME 12

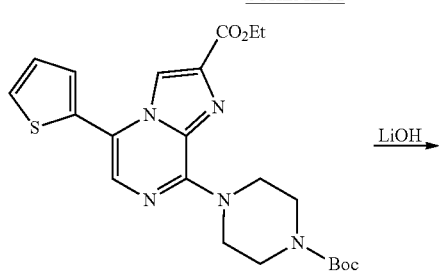

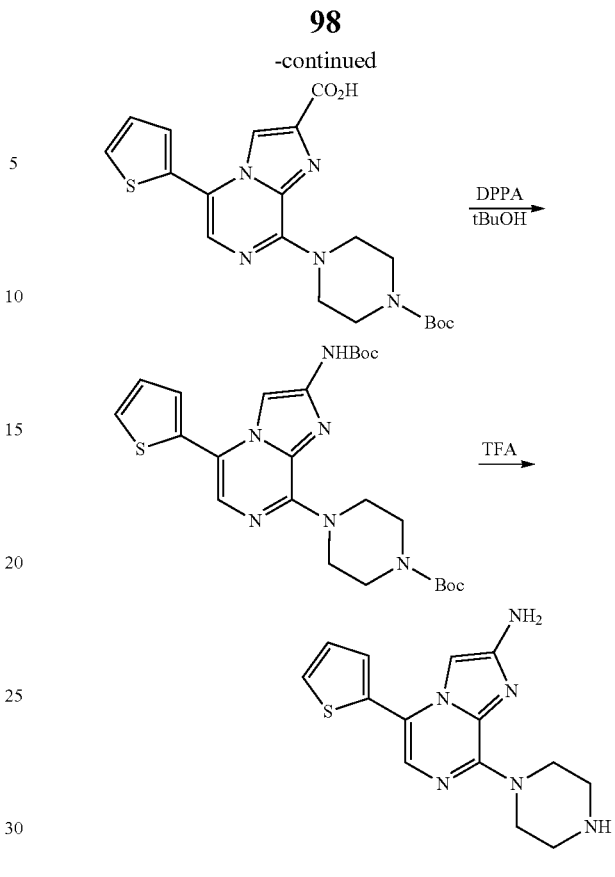

Example 65

8-(piperazin-1-yl)-5-(thiophen-2-yl)imidazo[1,2-a]pyrazin-2-amine

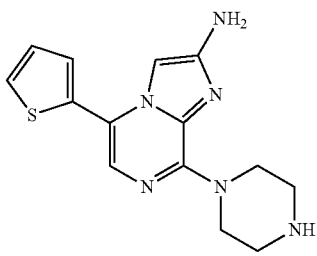 [SMILES: Nc1cn2c(-c3cccs3)cnc(N3CCNCC3)c2n1]

Step 1

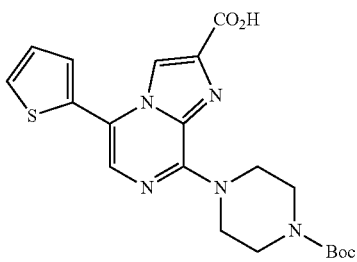 [SMILES: CC(C)(C)OC(=O)N1CCN(c2ncc(-c3cccs3)n3cc(C(=O)O)nc23)CC1]

8-(4-(tert-Butoxycarbonyl)piperazin-1-yl)-5-(thiophen-2-yl)imidazo[1,2-a]pyrazine-2-carboxylic acid A 100 mL round bottom flask was charged with ethyl 8-(4-(tert-butoxycarbonyl)piperazin-1-yl)-5-(thiophen-2-yl)imidazo[1,2-a]pyrazine-2-carboxylate (prepared as described in Example 61 steps 1-5, 0.80 g, 1.75 mmol), LiOH (0.22 g, 5.25 mmol), water (2 mL) and THF (30 mL). The mixture was stirred at 25° C. for 16 h. Reaction progress was monitored by LC-MS. Work-up: the solvent was evaporated. The residue was acidified with 2 N HCl. The precipitate was collected by filtration and dried, to afford 0.57 g (76%) of the product. MS m/z: 428 (M−H⁺).
Step 2

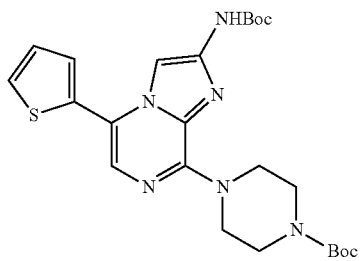 [SMILES: CC(C)(C)OC(=O)Nc1cn2c(-c3cccs3)cnc(N3CCN(C(=O)OC(C)(C)C)CC3)c2n1]

tert-Butyl 4-(2-((tert-butoxycarbonyl)amino)-5-(thiophen-2-yl)imidazo[1,2-a]pyrazin-8-yl)piperazine-1-carboxylate A 100 mL round bottom flask was charged with 8-(4-(tert-butoxycarbonyl)piperazin-1-yl)-5-(thiophen-2-yl)imidazo[1,2-a]pyrazine-2-carboxylic acid (0.57 g, 1.3 mmol), diphenyl phosphoryl azide (0.68 g, 2.5 mmol), triethylamine (0.25 g, 2.5 mmol) and tert-butanol (20 mL). The mixture was stirred at 80° C. for 16 h. Reaction progress was monitored by LC-MS. Work-up: the solvent was evaporated. The residue was purified by flash column chromatography on silica gel with a 1:20 EtOAc/petroleum ether, to afford 0.30 g (45%) of the product. MS m/z: 501 (M+H⁺).
Step 3

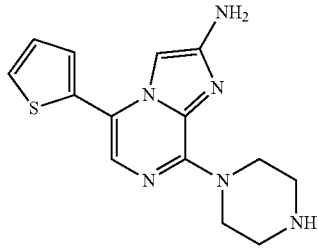

8-(piperazin-1-yl)-5-(thiophen-2-yl)imidazo[1,2-a]pyrazin-2-amine

The title compound was prepared as described as in Example 61 step 6, except that tert-butyl 4-(2-((tert-butoxycarbonyl)amino)-5-(thiophen-2-yl)imidazo[1,2-a]pyrazin-8-yl)piperazine-1-carboxylate was substituted for ethyl 8-(4-(tert-butoxycarbonyl)piperazin-1-yl)-5-(thiophen-2-yl)imidazo[1,2-a]pyrazine-2-carboxylate. ¹H NMR (300 MHz, DMSO-d₆) δ: 7.71 (dd, J=5.1, 1.2 Hz, 1H), 7.46 (dd, J=3.6, 1.2 Hz, 1H), 7.40 (s, 1H), 7.22 (dd, J=5.1, 3.6 Hz, 1H), 7.08 (s, 1H), 5.23 (br, 2H), 4.01 (t, J=5.0 Hz, 4H), 2.79 (t, J=5.0 Hz, 4H). MS m/z: 301 (M+H⁺).

Example 66

8-(4-Methylpiperazin-1-yl)-5-(thiophen-2-yl)imidazo[1,2-a]pyrazin-2-amine

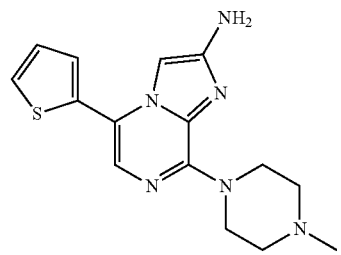 [SMILES: CN1CCN(c2ncc(-c3cccs3)n3cc(N)nc23)CC1]

The HCl salt of the title compound was prepared as described in Example 65, except that ethyl 8-(4-methylpiperazin-1-yl)-5-(thiophen-2-yl)imidazo[1,2-a]pyrazine-2-carboxylate (prepared as described in Example 61) was substituted for ethyl 8-(4-(tert-butoxycarbonyl)piperazin-1-yl)-5-(thiophen-2-yl)imidazo[1,2-a]pyrazine-2-carboxylate in step 1 of that route. ¹H NMR (300 MHz, DMSO-d₆) δ: 7.83 (d, J=4.8 Hz, 1H), 7.59 (s, 1H), 7.56 (d, J=2.7 Hz, 1H), 7.48 (s, 1H), 7.29 (dd, J=4.8, 3.6 Hz, 1H), 5.27 (d, J=13.8 Hz, 2H), 3.56-3.51 (m, 4H), 3.18 (m, 2H), 2.77 (s, 3H). MS m/z: 315 (M+H⁺).

SCHEME 13

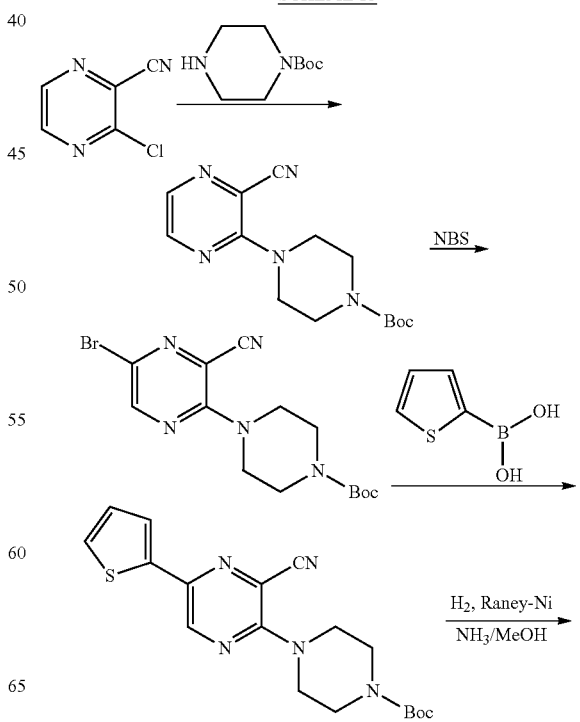

101

-continued

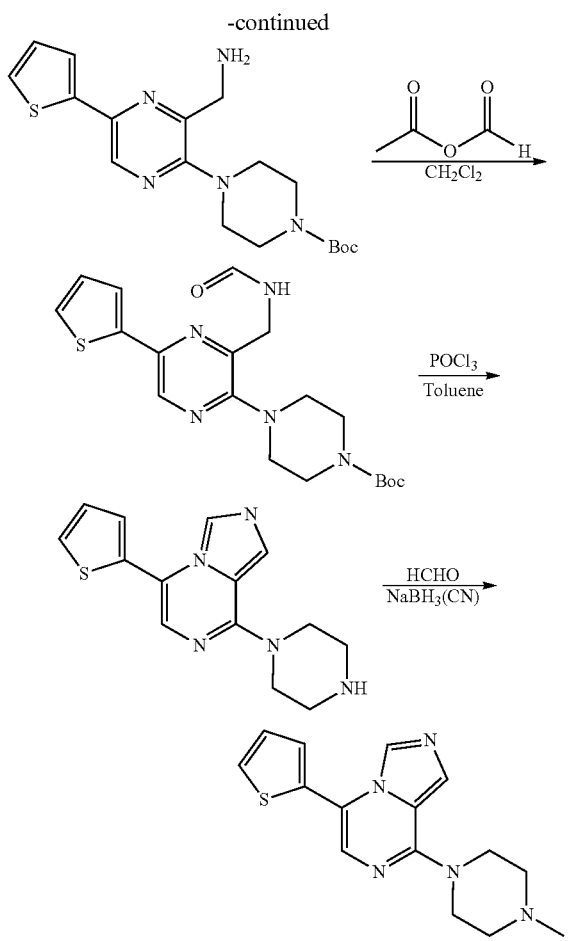

Example 67

8-(4-Methylpiperazin-1-yl)-5-(thiophen-2-yl)imidazo[1,5-a]pyrazine

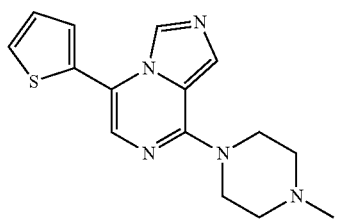 [SMILES: CN1CCN(c2ncc(-c3cccs3)n3cncc23)CC1]

Step 1-2

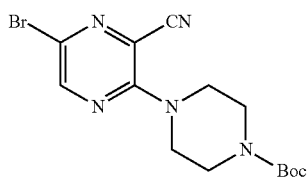 [SMILES: CC(C)(C)OC(=O)N1CCN(c2ncc(Br)nc2C#N)CC1]

102 tert-Butyl 4-(5-bromo-3-cyanopyrazin-2-yl)piperazine-1-carboxylate

The title compound was prepared as described in Example 1 steps 1-2, except that 3-chloropyrazine-2-carbonitrile was substituted for 2,3-dichloropyrazine as the starting material.

Step 3

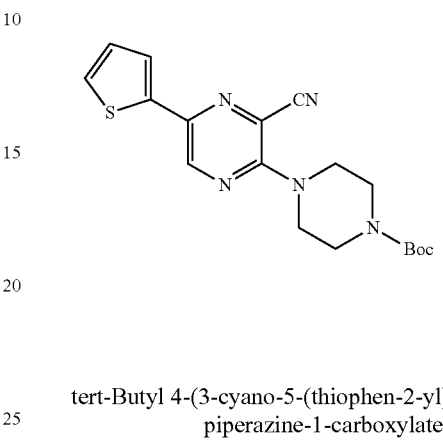

tert-Butyl 4-(3-cyano-5-(thiophen-2-yl)pyrazin-2-yl)piperazine-1-carboxylate

A 100 mL round bottom flask was charged with tert-butyl 4-(5-bromo-3-cyanopyrazin-2-yl)piperazine-1-carboxylate (1.0 g, 2.7 mmol), thiophen-2-ylboronic acid (0.52 g, 4.1 mmol), Pd(PPh$_3$)$_4$ (0.31 g, 0.27 mmol), Cs$_2$CO$_3$ (1.4 g, 4.1 mmol), 1,4-dioxane (20 mL) and water (10 mL). The resulting mixture was heated at 100° C. overnight under N$_2$ atmosphere. Work-up: the reaction mixture was poured into brine (80 mL) and extracted with EtOAc (30 mL×3). The combined organic layers were dried over anhydrous Na$_2$SO$_4$ and concentrated in vacuo. The residue was further purified by flash column chromatography on silica gel with 30% EtOAc in petroleum ether, to afford 700 mg (70%) of the product.

Step 4

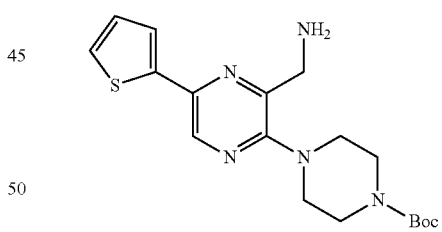

tert-Butyl 4-(3-(aminomethyl)-5-(thiophen-2-yl)pyrazin-2-yl)piperazine-1-carboxylate A 100 mL round bottom flask was charged with tert-butyl 4-(3-cyano-5-(thiophen-2-yl)pyrazin-2-yl)piperazine-1-carboxylate (0.75 g, 2.01 mmol), Raney Ni (200 mg) and 2 M solution of NH$_3$ in MeOH (50 mL). The resulting mixture was stirred at room temperature overnight under H$_2$ atmosphere. Work-up: the reaction mixture was filtered. The filtrated was concentrated in vacuo and the residue was purified by flash column chromatography on silica gel with 5% MeOH in CH$_2$Cl$_2$, to afford 680 mg (89%) of the product.

Step 5

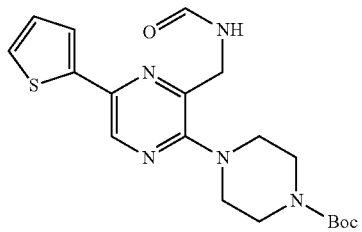 [SMILES: CC(C)(C)OC(=O)N1CCN(c2ncc(-c3cccs3)nc2CNC=O)CC1]

tert-Butyl 4-(3-(formamidomethyl)-5-(thiophen-2-yl)pyrazin-2-yl)piperazine-1-carboxylate A 50 mL round bottom flask was charged with tert-butyl 4-(3-(aminomethyl)-5-(thiophen-2-yl)pyrazin-2-yl)piperazine-1-carboxylate (0.70 g, 1.86 mmol), acetic formic anhydride (270 mg, 3.72 mmol) and dichloromethane (20 mL). The resulting mixture was stirred at room temperature overnight. Work-up: the reaction mixture was concentrated in vacuo. The residue was purified by flash column chromatography on silica gel with 50% EtOAc in petroleum ether, to afford 490 mg (65%) of the product.

Step 6

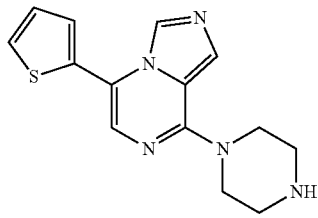 [SMILES: c1csc(-c2cnc(N3CCNCC3)c3cncn23)c1]

8-(piperazin-1-yl)-5-(thiophen-2-yl)imidazo[1,5-a]pyrazine

A 50 mL round bottom flask was charged with tert-butyl 4-(3-(formamidomethyl)-5-(thiophen-2-yl)pyrazin-2-yl)piperazine-1-carboxylate (0.40 g, 1.0 mmol) and toluene (20 mL). To the above mixture was added dropwise POCl₃ (0.76 g, 5.0 mmol). The resulting mixture was heated at 90° C. for 1 h. Work-up: the reaction mixture was poured into saturated aqueous NaHCO₃ and extracted with dichloromethane. The combined organic layers were washed with brine, dried over anhydrous Na₂SO₄ and concentrated in vacuo. The residue was further purified by flash column chromatography on silica gel with 5% MeOH in dichloromethane, to afford 0.25 g (85%) of the product. ¹H NMR (300 MHz, CDCl₃) δ: 8.41 (s, 1H), 7.74 (s, 1H), 7.46 (dd, J=5.1, 1.2 Hz, 1H), 7.37 (dd, J=3.6, 1.2 Hz, 1H), 7.25 (s, 1H), 7.19 (dd, J=5.1, 3.6 Hz, 1H), 3.89 (t, J=5.1 Hz, 4H), 3.08 (t, J=5.1 Hz, 4H). MS m/z: 286 (M+H⁺).

Step 7

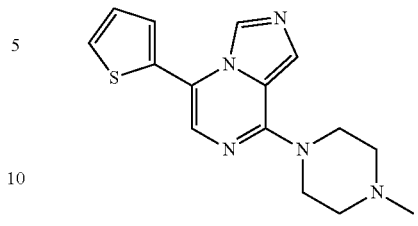

8-(4-Methylpiperazin-1-yl)-5-(thiophen-2-yl)imidazo[1,5-a]pyrazine

The title compound was prepared as described in Example 1 step 7, except that 8-(piperazin-1-yl)-5-(thiophen-2-yl)imidazo[1,5-a]pyrazine was substituted for 5-(furan-3-yl)-8-(piperazin-1-yl)-[1,2,4]-triazolo[4,3-a]pyrazine. ¹H NMR (300 MHz, CDCl₃) δ: 8.40 (s, 1H), 7.74 (s, 1H), 7.45 (dd, J=5.1, 1.2 Hz, 1H), 7.37 (dd, J=3.6, 1.2 Hz, 1H), 7.25 (s, 1H), 7.18 (dd, J=5.1, 3.6 Hz, 1H), 3.91 (t, J=5.1 Hz, 4H), 2.59 (t, J=5.1 Hz, 4H), 2.37 (s, 3H). MS m/z: 300 (M+H⁺).

Example 68

8-(piperazin-1-yl)-5-(thiophen-2-yl)imidazo[1,5-a]pyrazine

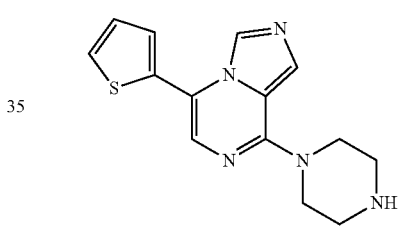

The title compound was prepared as described in Example 67 step 6. ¹H NMR (300 MHz, CDCl₃) δ: 8.41 (s, 1H), 7.74 (s, 1H), 7.46 (dd, J=5.1, 1.2 Hz, 1H), 7.37 (dd, J=3.6, 1.2 Hz, 1H), 7.25 (s, 1H), 7.19 (dd, J=5.1, 3.6 Hz, 1H), 3.89 (t, J=5.1 Hz, 4H), 3.08 (t, J=5.1 Hz, 4H). MS m/z: 286 (M+H⁺).

SCHEME 14

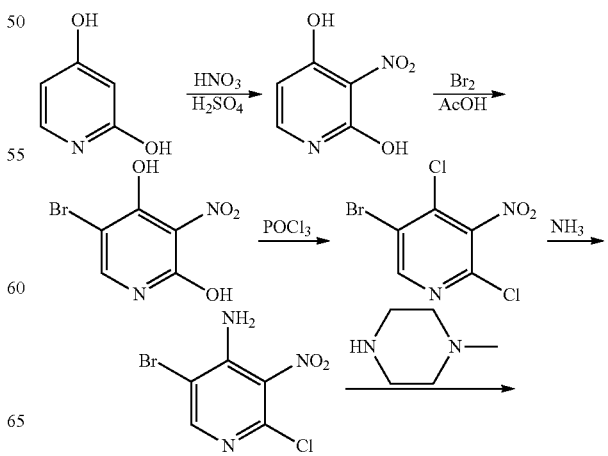

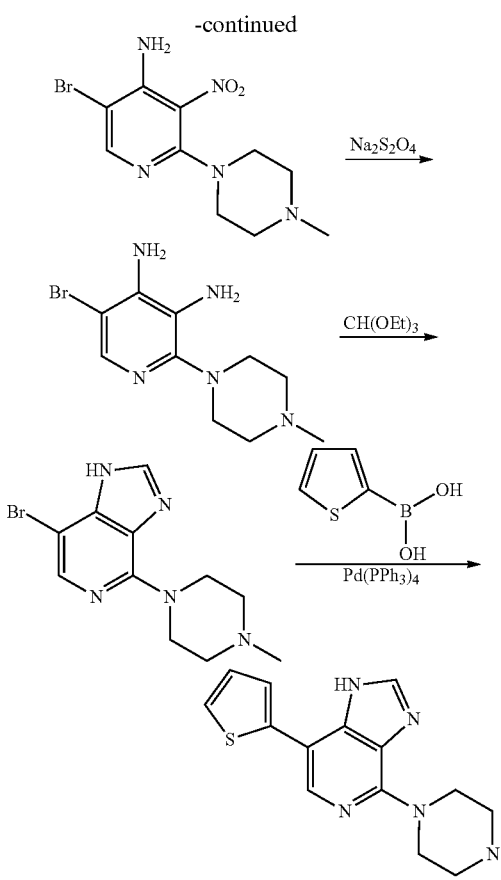

Example 69

4-(4-Methylpiperazin-1-yl)-7-(thiophen-2-yl)-1H-imidazo[4,5-c]pyridine

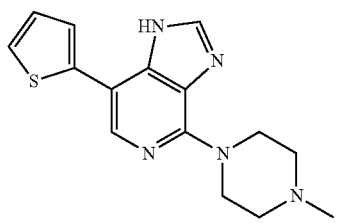 [SMILES: CN1CCN(c2ncc(-c3cccs3)c3[nH]cnc23)CC1]

Step 1

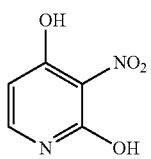

3-Nitropyridine-2,4-diol

A 100 mL 3-necked round bottom flask was charged with pyridine-2,4-diol (9.0 g, 81 mmol) and concentrated $H_2SO_4$ (40 mL). To the above solution was added dropwise fuming $HNO_3$ (40 mL) at 0° C. Work-up: the mixture was poured onto crushed ice and chilled in freezer. The resulting precipitate was collected by filtration, washed with cold water and dried in vacuo, to afford 11.4 g (90%) of the product as a colorless solid.

Step 2

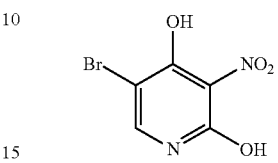

5-Bromo-3-nitropyridine-2,4-diol

A 100 mL 3-necked round bottom flask was charged with 3-nitropyridine-2,4-diol (3.5 g, 22 mmol), bromine (1.15 mL) and acetic acid (30 mL). The resulting mixture was heated at 70° C. for 15 minutes. Work-up: the mixture was poured onto crushed ice and chilled in freezer. The resulting precipitate was collected by filtration, washed with cold water and dried in vacuo, to afford 3.7 g (80%) of the product as a colorless solid.

Step 3

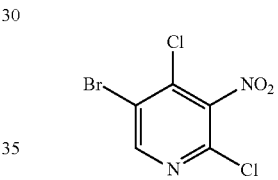

5-Bromo-2,4-dichloro-3-nitropyridine

A 100 mL round bottom flask was charged with 5-bromo-3-nitropyridine-2,4-diol (3.4 g, 20.8 mmol) and pyridine (3.5 mL). To the mixture was added $POCl_3$ (25 mL) over a period of 1 h while keeping the temperature below 50° C. The resulting suspension was then heated at reflux for 2.5 h. Work-up: the reaction mixture was concentrated in vacuo. The residue was poured into saturated aqueous $NaHCO_3$ and extracted with EtOAc. The combined organic layers were dried over anhydrous $Na_2SO_4$ and concentrated in vacuo. The residue was further purified by flash column chromatography on silica gel with 2.5% EtOAc in petroleum ether, to afford 2.0 g (70%) of the product as a white solid.

Step 4

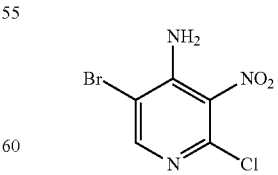

5-Bromo-2-chloro-3-nitropyridin-4-amine

A 250 mL round bottom flask was charged with 5-bromo-2,4-dichloro-3-nitropyridine (3.5 g, 12.6 mmol) and a solution of ammonia in 1,4-dioxane (150 mL). The mixture was heated at 30° C. for 4 h. Work-up: the reaction mixture was concentrated in vacuo. The residue was poured into saturated aqueous NaHCO$_3$ and extracted with EtOAc. The combined organic layers were dried over anhydrous Na$_2$SO$_4$ and concentrated in vacuo. The residue was further purified by flash column chromatography on silica gel with 20% EtOAc in petroleum ether, to afford 1.5 g (46%) of the product as a white solid. MS m/z: 252 (M+H$^+$).

Step 5

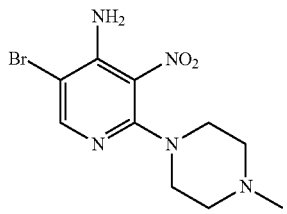 [SMILES: CN1CCN(c2ncc(Br)c(N)c2[N+](=O)[O-])CC1]

5-Bromo-2-(4-methylpiperazin-1-yl)-3-nitropyridin-4-amine

A 20 mL microwave reaction tube was charged with 5-bromo-2-chloro-3-nitropyridin-4-amine (1.0 g, 3.9 mmol), N-methylpiperazine (0.78 g, 7.8 mmol) and anhydrous ethanol (15 mL). The resulting solution was heated at 130° C. for 1 h in a Biotage microwave reactor. The solvent was evaporated and the residue was purified by flash column chromatography on silica gel with 10% MeOH in CH$_2$Cl$_2$, to afford 0.80 g (64%) of the product as a white solid. MS m/z: 316 (M+H$^+$).

Step 6

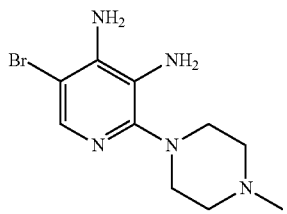 [SMILES: CN1CCN(c2ncc(Br)c(N)c2N)CC1]

5-Bromo-2-(4-methylpiperazin-1-yl)pyridine-3,4-diamine

A 250 mL round bottom flask was charged with 5-bromo-2-(4-methylpiperazin-1-yl)-3-nitropyridin-4-amine (1.5 g, 4.7 mmol), Na$_2$S$_2$O$_4$ (2.0 g, 11 mmol), water (10 mL) and ethanol (20 mL). The mixture was heated at reflux for 0.5 h. Work-up: the solvent was evaporated. The residue was re-suspended in triethylamine (15 mL) and ethyl acetate (300 mL), and then filtered. The filtrate was concentrated in vacuo, to afford 1.1 g (80%) of the product as a pale-red solid. MS m/z: 286 (M+H$^+$).

Step 7

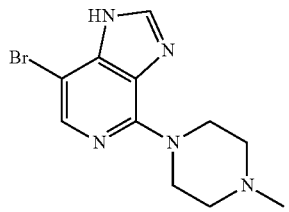 [SMILES: CN1CCN(c2ncc(Br)c3[nH]cnc23)CC1]

7-Bromo-4-(4-methylpiperazin-1-yl)-1H-imidazo[4,5-c]pyridine

A 100 mL round bottom flask was charged with 5-bromo-2-(4-methylpiperazin-1-yl)pyridine-3,4-diamine (1.1 g, 3.8 mmol) and triethyl orthoformate (20 mL). The resulting mixture was stirred at 130° C. for 1 h. Reaction progress was monitored by TLC (EtOAc/petroleum ether=2:1). Work-up: the reaction mixture was concentrated in vacuo. The residue was re-dissolved in EtOAc (50 mL) and washed with brine (20 mL). The organic layer was dried over anhydrous Na$_2$SO$_4$ and concentrated in vacuo. The residue was further purified by flash column chromatography on silica gel with 10-40% EtOAc in CH$_2$Cl$_2$, to afford 0.9 g (79%) of the product as a white solid. MS m/z: 296 (M+H$^+$).

Step 8

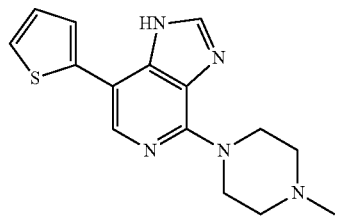 [SMILES: CN1CCN(c2ncc(-c3cccs3)c3[nH]cnc23)CC1]

4-(4-Methylpiperazin-1-yl)-7-(thiophen-2-yl)-1H-imidazo[4,5-c]pyridine

A 20 mL microwave reaction tube was charged with 7-bromo-4-(4-methylpiperazin-1-yl)-1H-imidazo[4,5-c]pyridine (296 mg, 1.0 mmol), thiophene-2-boronic acid (192 mg, 1.5 mmol), tetrakis(triphenylphosphine)palladium(0) (115 mg, 0.010 mmol), Cs$_2$CO$_3$ (326 mg, 1.44 mmol), 1,4-dioxane (8 mL) and water (4 mL). After the air was purged by bubbling N$_2$ into the solution, the tube was sealed and heated at 90° C. for 3 h in a Biotage microwave reactor. Work-up: the reaction mixture was diluted with 0.1 M HCl (50 mL) and washed with EtOAc (50 mL×2). The aqueous layer was basified with solid NaHCO$_3$ and then extracted with CH$_2$Cl$_2$ (50 mL×3). The combined CH$_2$Cl$_2$ layers were dried over anhydrous Na$_2$SO$_4$ and concentrated in vacuo. The residue was purified by flash column chromatography on silica gel with 1-10% MeOH in CH$_2$Cl$_2$, to afford 220 mg (73%) of the product. It was converted into the corresponding HCl salt by treating with methanolic HCl solution. $^1$H NMR (300 MHz, D$_2$O) δ: 8.26 (s, 1H), 7.74 (s, 1H), 7.49 (dd, J=5.1, 0.9 Hz, 1H), 7.31 (dd, J=3.6, 0.9 Hz, 1H), 7.13 (dd, J=5.1, 3.6 Hz, 1H), 4.94 (d, J=14.1 Hz, 2H), 3.70-3.63 (m, 4H), 3.34-3.20 (m, 2H), 2.90 (s, 3H). MS m/z: 300 (M+H$^+$).

Example 70

4-(piperazin-1-yl)-7-(thiophen-2-yl)-1H-imidazo[4,5-c]pyridine

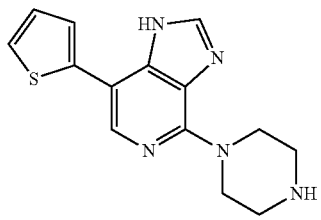 [SMILES: c1csc(-c2cnc(N3CCNCC3)c3nc[nH]c23)c1]

The HCl salt of the title compound was prepared as described in Example 69, except that piperazine was substituted for N-methylpiperazine in step 5 of that route. $^1$H NMR (300 MHz, D$_2$O) δ: 8.25 (s, 1H), 7.71 (s, 1H), 7.48 (dd, J=5.1, 1.2 Hz, 1H), 7.29 (dd, J=3.9, 1.2 Hz, 1H), 7.11 (dd, J=5.1, 3.9 Hz, 1H), 4.29 (t, J=5.4 Hz, 4H), 3.42 (t, J=5.4 Hz, 4H). MS m/z: 286 (M+H$^+$).

Example 71

4-(4-Methylpiperazin-1-yl)-7-(thiophen-3-yl)-1H-imidazo[4,5-c]pyridine

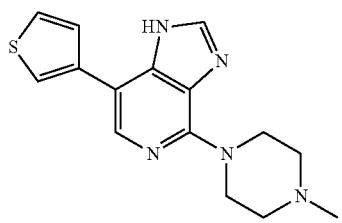 [SMILES: CN1CCN(c2ncc(-c3ccsc3)c3[nH]cnc23)CC1]

The HCl salt of the title compound was prepared as described in Example 69, except that thiophene-3-boronic acid was substituted for thiophene-2-boronic acid in step 8 of that route. $^1$H NMR (300 MHz, D$_2$O) δ: 8.25 (s, 1H), 7.70 (s, 1H), 7.59 (dd, J=3.0, 1.2 Hz, 1H), 7.51 (dd, J=5.1, 3.0 Hz, 1H), 7.24 (dd, J=5.1, 1.2 Hz, 1H), 4.93 (d, J=15.0 Hz, 2H), 3.80-3.63 (m, 4H), 3.40-3.20 (m, 2H), 2.89 (s, 3H). MS m/z: 300 (M+H$^+$).

Example 72

4-(piperazin-1-yl)-7-(thiophen-3-yl)-1H-imidazo[4,5-c]pyridine

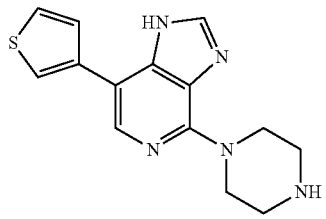

The HCl salt of the title compound was prepared as described in Example 71, except that piperazine was substituted for N-methylpiperazine in step 5 of that route. $^1$H NMR (300 MHz, D$_2$O) δ: 8.23 (s, 1H), 7.67 (s, 1H), 7.56 (dd, J=3.0, 1.2 Hz, 1H), 7.49 (dd, J=5.1, 3.0 Hz, 1H), 7.22 (dd, J=5.1, 1.2 Hz, 1H), 4.26 (t, J=5.4 Hz, 4H), 3.41 (t, J=5.4 Hz, 4H). MS m/z: 286 (M+H$^+$).

SCHEME 15

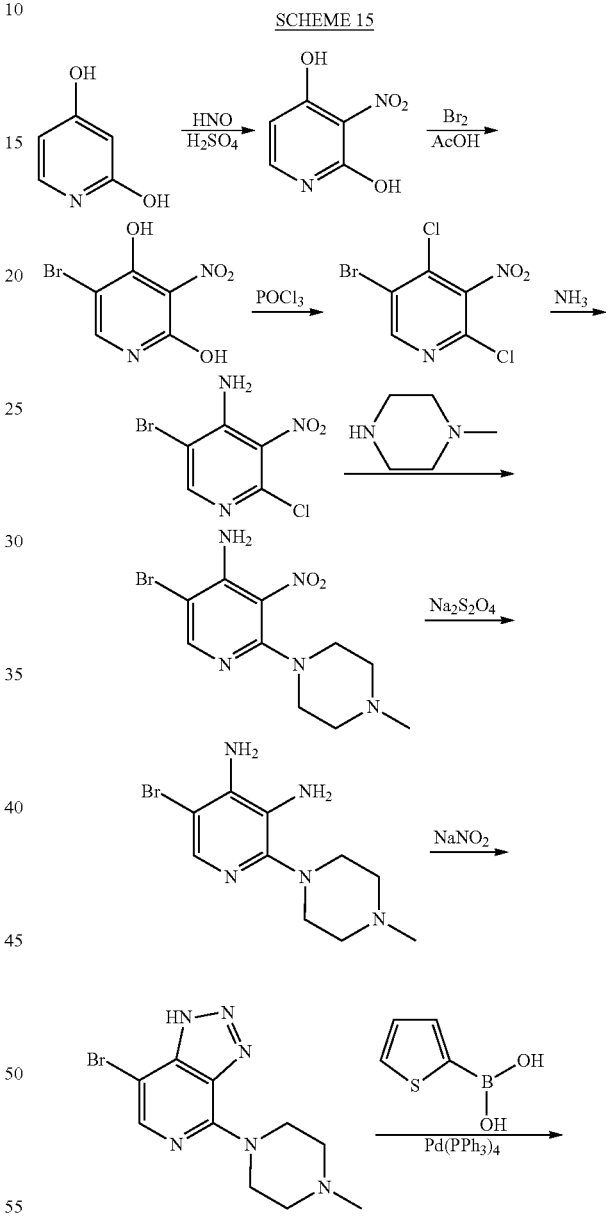

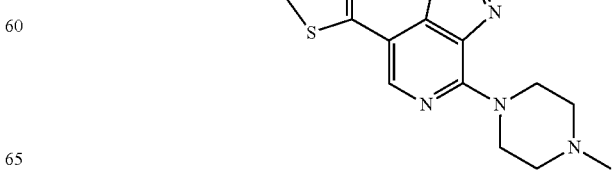

Example 73

4-(4-Methylpiperazin-1-yl)-7-(thiophen-2-yl)-1H-[1,2,3]triazolo[4,5-c]pyridine

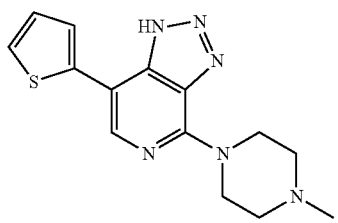 [SMILES: CN1CCN(c2ncc(-c3cccs3)c3[nH]nnc23)CC1]

Step 1-6

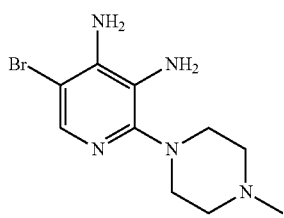 [SMILES: CN1CCN(c2ncc(Br)c(N)c2N)CC1]

5-Bromo-2-(4-methylpiperazin-1-yl)pyridine-3,4-diamine

The title compound was prepared as described in Example 69 steps 1-6.

Step 7

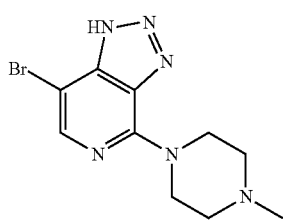 [SMILES: CN1CCN(c2ncc(Br)c3[nH]nnc23)CC1]

7-Bromo-4-(4-methylpiperazin-1-yl)-1H-[1,2,3]triazolo[4,5-c]pyridine

A 250 mL round bottom flask was charged with 5-bromo-2-(4-methylpiperazin-1-yl)pyridine-3,4-diamine (1.2 g, 4.2 mmol) and CH$_3$COOH (10 mL). To the above was added dropwise a solution of NaNO$_2$ (0.30 g, 4.3 mmol) in water (1 mL) at 10° C. The resulting mixture was stirred at 10° C. for 1 h. Work-up: the reaction mixture was basified to pH 8 by saturated aqueous Na$_2$CO$_3$ and extracted with ethyl acetate (30 mL×3). The combined organic layers were dried over anhydrous Na$_2$SO$_4$ and concentrated in vacuo. The residue was purified by flash column chromatography on silica gel with 10% MeOH in CH$_2$Cl$_2$, to afford 1.1 g (88%) of the product as a white solid. MS m/z: 297 (M+H$^+$).

Step 8

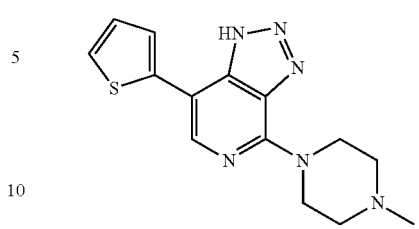

4-(4-Methylpiperazin-1-yl)-7-(thiophen-2-yl)-1H-[1,2,3]triazolo[4,5-c]pyridine

The HCl salt of the title compound was prepared as described in Example 69 step 8, except that 7-bromo-4-(4-methylpiperazin-1-yl)-1H-[1,2,3]triazolo[4,5-c]pyridine was substituted for 7-bromo-4-(4-methylpiperazin-1-yl)-1H-imidazo[4,5-c]pyridine. $^1$H NMR (300 MHz, D$_2$O) δ: 7.62 (s, 1H), 7.47 (m, 1H), 7.33 (m, 1H), 7.10 (dd, J=5.1, 3.6 Hz, 1H), 5.10 (d, 2H), 3.80-3.65 (m, 4H), 3.40-3.20 (m, 2H), 2.91 (s, 3H). MS m/z: 301 (M+H$^+$).

Example 74

4-(piperazin-1-yl)-7-(thiophen-2-yl)-1H-[1,2,3]triazolo[4,5-c]pyridine

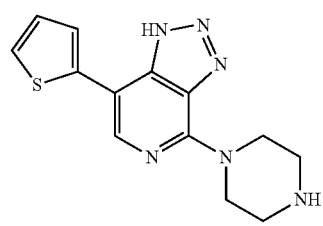 [SMILES: c1csc(-c2cnc(N3CCNCC3)c3nn[nH]c23)c1]

The HCl salt of the title compound was prepared as described in Example 73, except that piperazine was substituted for N-methylpiperazine in step 5 of that route. $^1$H NMR (300 MHz, D$_2$O) δ: 7.63 (s, 1H), 7.47 (dd, J=5.1, 0.9 Hz, 1H), 7.33 (dd, J=3.9, 0.9 Hz, 1H), 7.09 (dd, J=5.1, 3.9 Hz, 1H), 4.44 (t, J=5.4 Hz, 4H), 3.49 (t, J=5.4 Hz, 4H). MS m/z: 287 (M+H$^+$).

Example 75

4-(4-Methylpiperazin-1-yl)-7-(thiophen-3-yl)-1H-[1,2,3]triazolo[4,5-c]pyridine

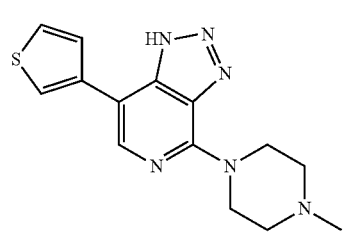 [SMILES: CN1CCN(c2ncc(-c3ccsc3)c3[nH]nnc23)CC1]

The HCl salt of the title compound was prepared as described in Example 73, except that thiophene-3-boronic acid was substituted for thiophene-2-boronic acid in step 8 of that route. $^1$H NMR (300 MHz, D$_2$O) δ: 7.72-7.69 (m, 2H), 7.52 (dd, J=5.1, 3.0 Hz, 1H), 7.31 (dd, J=5.1, 1.2 Hz, 1H), 5.12 (d, J=14.4 Hz, 2H), 3.81-3.69 (m, 4H), 3.40-3.20 (m, 2H), 2.91 (s, 3H). MS m/z: 301 (M+H$^+$).

Example 76

4-(piperazin-1-yl)-7-(thiophen-3-yl)-1H-[1,2,3]triazolo[4,5-c]pyridine

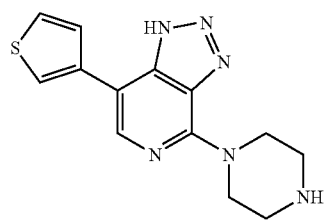 [SMILES: c1cc(-c2cnc(N3CCNCC3)c3nn[nH]c23)cs1]

The HCl salt of the title compound was prepared as described in Example 75, except that piperazine was substituted for N-methylpiperazine in step 5 of that route. $^1$H NMR (300 MHz, D$_2$O) δ: 7.71-7.69 (m, 2H), 7.52 (dd, J=5.1, 3.0 Hz, 1H), 7.29 (dd, J=5.1, 0.9 Hz, 1H), 4.46 (t, J=5.1 Hz, 4H), 3.49 (t, J=5.1 Hz, 4H). MS m/z: 287 (M+H$^+$).

SCHEME 16

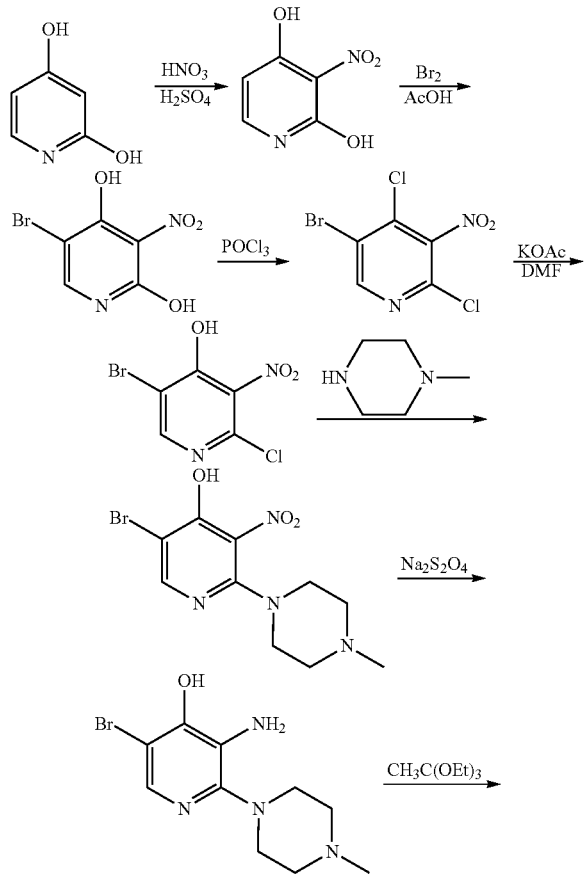

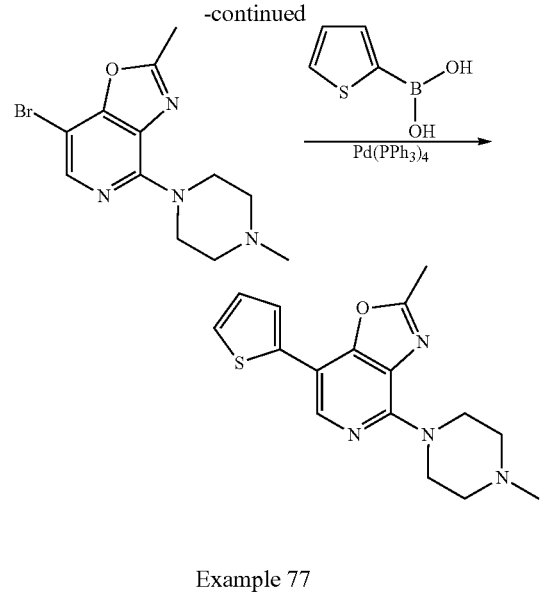

Example 77

2-Methyl-4-(4-methylpiperazin-1-yl)-7-(thiophen-2-yl)oxazolo[4,5-c]pyridine

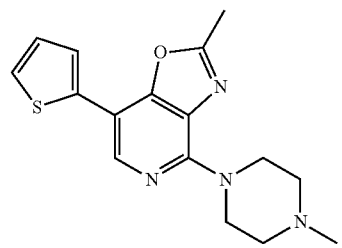 [SMILES: Cc1nc2c(N3CCN(C)CC3)ncc(-c3cccs3)c2o1]

The title compound was prepared as described in Example 69, except that potassium acetate was substituted for ammonia in step 4 (Reference: US2003/225131 A1 Example 4.A), and triethyl orthoacetate for triethyl orthoformate in step 7 of that route. $^1$H NMR (300 MHz, CDCl$_3$) δ: 8.30 (s, 1H), 7.50 (dd, J=3.6, 1.2 Hz, 1H), 7.28 (dd, J=5.1, 1.2 Hz, 1H), 7.12 (dd, J=5.1, 3.6 Hz, 1H), 4.12 (t, J=5.1 Hz, 4H), 2.66 (s, 3H), 2.56 (t, J=5.1 Hz, 4H), 2.36 (s, 3H). MS m/z: 315 (M+H$^+$).

Example 78

2-Methyl-4-(piperazin-1-yl)-7-(thiophen-2-yl)oxazolo[4,5-c]pyridine

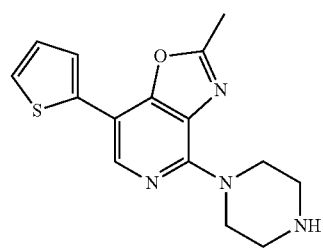 [SMILES: Cc1nc2c(N3CCNCC3)ncc(-c3cccs3)c2o1]

The HCl salt of the title compound was prepared as described in Example 77, except that piperazine was substituted for N-methylpiperazine in step 5 of that route. ¹H NMR (300 MHz, D₂O) δ: 7.85 (s, 1H), 7.44 (d, J=4.8 Hz, 1H), 7.40 (d, J=3.6 Hz, 1H), 7.05 (t, J=4.2 Hz, 1H), 4.16 (t, J=5.1 Hz, 4H), 3.42 (t, J=5.1 Hz, 4H), 2.60 (s, 3H). MS m/z: 301 (M+H⁺).

Example 79

2-Methyl-4-(4-methylpiperazin-1-yl)-7-(thiophen-3-yl)oxazolo[4,5-c]pyridine

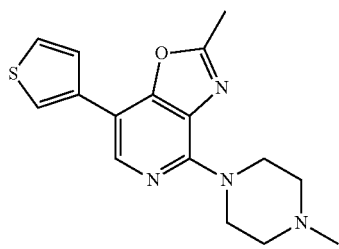 [SMILES: Cc1nc2c(N3CCN(C)CC3)ncc(-c3ccsc3)c2o1]

The title compound was prepared as described in Example 77, except that thiophene-3-boronic acid was substituted for thiophene-2-boronic acid in step 8 of that route. ¹H NMR (300 MHz, CDCl₃) δ: 8.32 (s, 1H), 7.70 (dd, J=3.0, 1.2 Hz, 1H), 7.55 (dd, J=5.1, 1.2 Hz, 1H), 7.42 (dd, J=5.1, 3.0 Hz, 1H), 4.11 (t, J=5.1 Hz, 4H), 2.66 (s, 3H), 2.57 (t, J=5.1 Hz, 4H), 2.36 (s, 3H). MS m/z: 315 (M+H⁺).

Example 80

2-Methyl-4-(piperazin-1-yl)-7-(thiophen-3-yl)oxazolo[4,5-c]pyridine

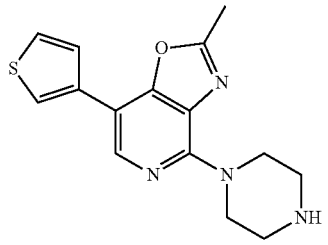 [SMILES: Cc1nc2c(N3CCNCC3)ncc(-c3ccsc3)c2o1]

The HCl salt of the title compound was prepared as described in Example 79, except that piperazine was substituted for N-methylpiperazine in step 5 of that route. ¹H NMR (300 MHz, D₂O) δ: 7.89 (s, 1H), 7.70 (dd, J=3.0, 1.2 Hz, 1H), 7.41 (dd, J=5.4, 2.7 Hz, 1H), 7.27 (dd, J=5.1, 1.2 Hz, 1H), 4.19 (t, J=5.2 Hz, 4H), 3.42 (t, J=5.2 Hz, 4H), 2.60 (s, 3H). MS m/z: 301 (M+H⁺).

SCHEME 17

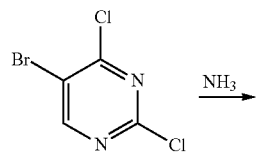

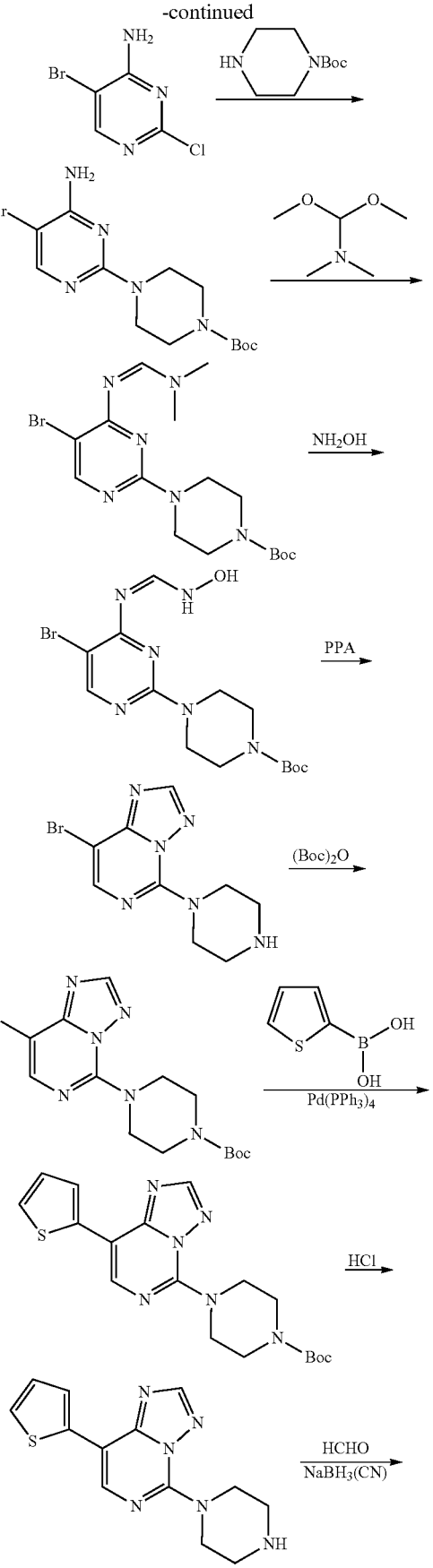

117

-continued

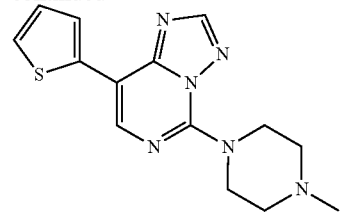 [SMILES: CN1CCN(c2ncc(-c3cccs3)c3ncnn23)CC1]

Example 81

5-(4-Methylpiperazin-1-yl)-8-(thiophen-2-yl)-[1,2,4]triazolo[1,5-c]pyrimidine

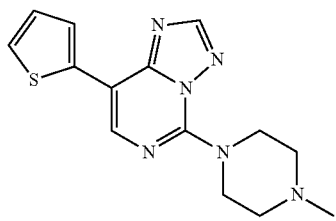

Step 1

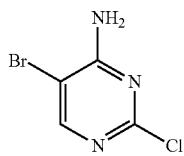

5-Bromo-2-chloropyrimidin-4-amine

A 100 mL round bottom flask was charged with 5-bromo-2,4-dichloropyrimidine (10.0 g, 44 mmol), concentrated ammonium hydroxide (100 mL) and THF (150 mL). The resulting mixture was magnetically stirred at room temperature for 12 h. Work-up: the reaction mixture was diluted with water (100 mL) and then extracted with EtOAc (50 mL×3). The combined organic layers were dried over anhydrous Na$_2$SO$_4$ and concentrated in vacuo. The residue was purified by flash column chromatography on silica gel to afford 11 g (quantitative) of the product as a white solid. MS m/z: 208 (M+H$^+$).

Step 2

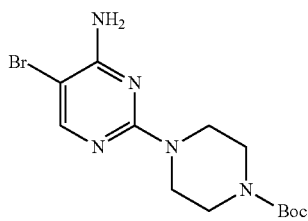 [SMILES: CC(C)(C)OC(=O)N1CCN(c2ncc(Br)c(N)n2)CC1]

118 tert-Butyl 4-(4-amino-5-bromopyrimidin-2-yl)piperazine-1-carboxylate

A 100 mL round bottom flask was charged with 5-bromo-2-chloropyrimidin-4-amine (8.0 g, 40 mmol), N,N-diisopropylethylamine (16.0 g, 120 mmol) and tert-butyl piperazine-1-carboxylate (11.0 g, 60 mmol). The resulting mixture was heated at reflux overnight. Work-up: the solvent was evaporated. The residue was re-crystallized from ethanol to afford 9.0 g (65%) of the product as a white solid. MS m/z: 358 (M+H$^+$).

Step 3

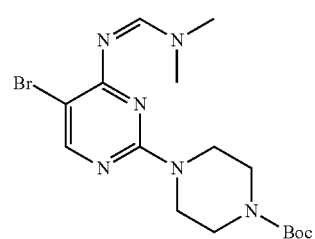 [SMILES: CN(C)/C=N\c1nc(N2CCN(C(=O)OC(C)(C)C)CC2)ncc1Br]

tert-Butyl 4-(5-bromo-4-(((dimethylamino)methylene)amino)pyrimidin-2-yl)piperazine-1-carboxylate A 100 mL round bottom flask was charged with tert-butyl 4-(4-amino-5-bromopyrimidin-2-yl)piperazine-1-carboxylate (2.0 g, 5.6 mmol), N,N-dimethylformamide dimethyl acetal (0.9 g, 7.3 mmol) and toluene (60 mL). The resulting mixture was heated at reflux for 12 h. Work-up: the solvent was evaporated to dryness to afford the product, which was used in the next step without further purification.

Step 4

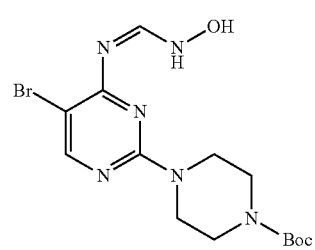 [SMILES: CC(C)(C)OC(=O)N1CCN(c2ncc(Br)c(/N=C\NO)n2)CC1]

tert-Butyl 4-(5-bromo-4-(((hydroxyamino)methylene)amino)pyrimidin-2-yl)piperazine-1-carboxylate A 100 mL round bottom flask was charged with tert-butyl 4-(5-bromo-4-(((dimethylamino)methylene)amino)pyrimidin-2-yl)piperazine-1-carboxylate (2.0 g) and methanol (30 mL). To the above solution was added hydroxylamine hydrochloride (0.5 g, 7.3 mmol) in one portion. The resulting mixture was stirred at room temperature for 12 h. Work-up: the solvent was evaporated. The resulting crystalline solid was washed with water and collected by filtration. The solid was washed with ethanol (100 mL) and dried, to afford 1.0 g (80%) of the product as a white solid.

Step 5

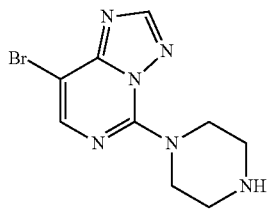 [SMILES: Brc1cnc(N2CCNCC2)n2ncnc12]

8-Bromo-5-(piperazin-1-yl)-[1,2,4]triazolo[1,5-c]pyrimidine

A 100 mL round bottom flask was charged with tert-butyl 4-(5-bromo-4-(((hydroxyamino)methylene)amino)pyrimidin-2-yl)piperazine-1-carboxylate (1.1 g) and polyphosphoric acid (20 g). The resulting mixture was stirred at 100° C. overnight. Work-up: the reaction mixture was carefully diluted with saturated aqueous KOH (300 mL) and then extracted with CH$_2$Cl$_2$ (100 mL×3). The combined organic layers were dried over anhydrous Na$_2$SO$_4$ and concentrated in vacuo. The residue was purified by flash column chromatography on silica gel to afford 0.3 g (39%) of the product as a white solid. MS m/z: 283 (M+H$^+$).

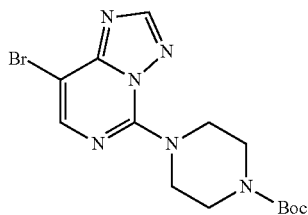 [SMILES: CC(C)(C)OC(=O)N1CCN(c2ncc(Br)c3ncnn23)CC1]

Step 6 tert-Butyl 4-(8-bromo-[1,2,4]triazolo[1,5-c]pyrimidin-5-yl)piperazine-1-carboxylate A 100 mL round bottom flask was charged with 8-bromo-5-(piperazin-1-yl)-[1,2,4]triazolo[1,5-c]pyrimidine (0.6 g, 2 mmol), di-(tert-butyl) dicarbonate (1.4 g, 6 mmol), triethylamine (0.63 g, 6 mmol) and CH$_2$Cl$_2$ (20 mL). The resulting solution was stirred at room temperature overnight. Work-up: the reaction mixture was mixed with water (20 mL) and extracted with CH$_2$Cl$_2$ (20 mL×2). The combined organic layers were dried over anhydrous Na$_2$SO$_4$ and concentrated in vacuo. The residue was purified by flash column chromatography on silica gel to afford 0.4 g (49%) of the product as a yellow solid.

Step 7

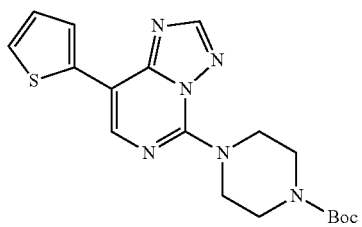 [SMILES: CC(C)(C)OC(=O)N1CCN(c2ncc(-c3cccs3)c3ncnn23)CC1]

tert-Butyl 4-(8-(thiophen-2-yl)-[1,2,4]triazolo[1,5-c]pyrimidin-5-yl)piperazine-1-carboxylate A 50 mL round bottom flask was charged with tert-butyl 4-(8-bromo-[1,2,4]triazolo[1,5-c]pyrimidin-5-yl)piperazine-1-carboxylate (0.6 g, 1.57 mmol), thiophene-2-boronic acid (0.35 g, 2.74 mmol), tetrakis(triphenylphosphine)palladium(0) (0.25 g, 0.21 mmol), Cs$_2$CO$_3$ (2 g, 6.36 mmol), 1,4-dioxane (20 mL) and water (5 mL). After the air was purged by bubbling N$_2$ into the solution, the resulting mixture was stirred at 100° C. under N$_2$ overnight. Work-up: the reaction mixture was diluted with water and extracted with CH$_2$Cl$_2$ (50 mL×3). The combined organic layers were dried over anhydrous Na$_2$SO$_4$ and concentrated in vacuo. The residue was purified by flash column chromatography on silica gel to afford 0.5 g (82%) of the product as a white solid.

Step 8

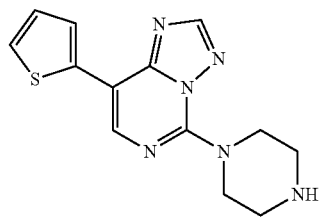 [SMILES: c1csc(-c2cnc(N3CCNCC3)n3ncnc23)c1]

5-(piperazin-1-yl)-8-(thiophen-2-yl)-[1,2,4]triazolo[1,5-c]pyrimidine

A 50 mL round bottom flask was charged with tert-butyl 4-(8-(thiophen-2-yl)-[1,2,4]triazolo[1,5-c]pyrimidin-5-yl)piperazine-1-carboxylate (0.5 g, 1.3 mmol) and THF (15 mL). To the above solution was added concentrated HCl (2 mL) dropwise. The resulting mixture was stirred for 0.5 h at room temperature. The precipitate was collected by filtration and dried, to afford 0.33 g (79%) of the HCl salt of the product as a white solid. $^1$H NMR (300 MHz, DMSO-d$_6$) δ: 8.68 (s, 1H), 8.46 (s, 1H), 7.97 (dd, J=3.9, 0.9 Hz, 1H), 7.64 (dd, J=5.1, 0.9 Hz, 1H), 7.20 (dd, J=5.1, 3.9 Hz, 1H), 4.26 (t, J=4.8 Hz, 4H), 3.32 (br, 4H). MS m/z: 287 (M+H$^+$).

Step 9

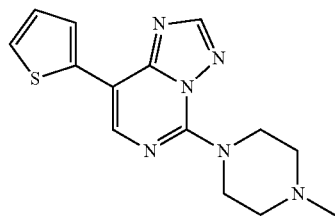 [SMILES: CN1CCN(c2ncc(-c3cccs3)c3ncnn23)CC1]

5-(4-Methylpiperazin-1-yl)-8-(thiophen-2-yl)-[1,2,4]triazolo[1,5-c]pyrimidine

A 100 mL round bottom flask was charged with 5-(piperazin-1-yl)-8-(thiophen-2-yl)-[1,2,4]-triazolo[1,5-c]pyrimidine HCl salt (0.25 g, 0.77 mmol), CH$_2$Cl$_2$ (1 mL), MeOH (10 mL), 40% aqueous formaldehyde (2 mL) and NaBH$_3$(CN) (0.073 g, 1.16 mmol). The resulting solution was stirred at room temperature for 1.5 h. Work-up: the reaction mixture was diluted with water and extracted with CH$_2$Cl$_2$ (50 mL×3).

The combined organic layers were dried over anhydrous Na$_2$SO$_4$ and concentrated in vacuo. The residue was purified by flash column chromatography on silica gel to afford 0.2 g (86%) of the product as a white solid. It was converted into the corresponding HCl salt by treating with methanolic HCl solution. $^1$H NMR (300 MHz, DMSO-d$_6$) δ: 8.71 (s, 1H), 8.49 (s, 1H), 7.98 (dd, J=3.6, 1.2 Hz, 1H), 7.65 (dd, J=5.1, 1.2 Hz, 1H), 7.21 (dd, J=5.1, 3.6 Hz, 1H), 4.99 (d, J=15.3 Hz, 2H), 3.67-3.53 (m, 4H), 3.32-3.16 (m, 2H), 2.81 (d, J=4.8 Hz, 3H). MS m/z: 301 (M+H$^+$).

Example 82

5-(piperazin-1-yl)-8-(thiophen-2-yl)-[1,2,4]triazolo[1,5-c]pyrimidine

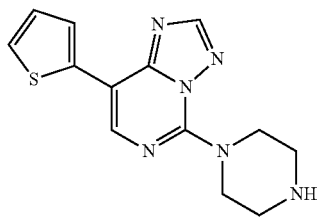

The HCl salt of the title compound was prepared as described in Example 81 step 8. $^1$H NMR (300 MHz, DMSO-d$_6$) δ: 8.68 (s, 1H), 8.46 (s, 1H), 7.97 (dd, J=3.9, 0.9 Hz, 1H), 7.64 (dd, J=5.1, 0.9 Hz, 1H), 7.20 (dd, J=5.1, 3.9 Hz, 1H), 4.26 (t, J=4.8 Hz, 4H), 3.32 (br, 4H). MS m/z: 287 (M+H$^+$).

Example 83

2-Methyl-5-(4-methylpiperazin-1-yl)-8-(thiophen-2-yl)-[1,2,4]triazolo[1,5-c]pyrimidine

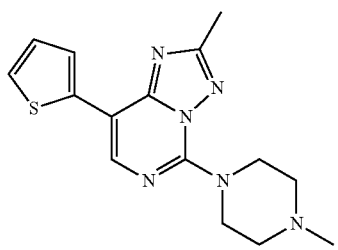 [SMILES: Cc1nc2c(-c3cccs3)cnc(N3CCN(C)CC3)n2n1]

The HCl salt of the title compound was prepared as described in Example 81, except that N,N-dimethylacetamide dimethyl acetal was substituted for N,N-dimethylformamide dimethyl acetal in step 3 of that route. $^1$H NMR (300 MHz, DMSO-d$_6$) δ: 8.43 (s, 1H), 7.95 (dd, J=3.6, 1.2 Hz, 1H), 7.63 (dd, J=5.1, 1.2 Hz, 1H), 7.19 (dd, J=5.1, 3.6 Hz, 1H), 4.97 (d, J=14.4 Hz, 2H), 3.65-3.53 (m, 4H), 3.28-3.16 (m, 2H), 2.80 (d, J=4.8 Hz, 3H), 2.56 (s, 3H). MS m/z: 315 (M+H$^+$).

Example 84

2-Methyl-5-(piperazin-1-yl)-8-(thiophen-2-yl)-[1,2,4]triazolo[1,5-c]pyrimidine

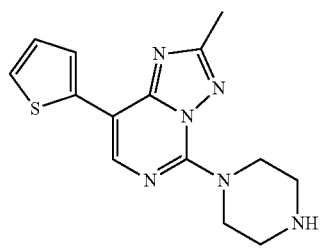 [SMILES: Cc1nc2c(-c3cccs3)cnc(N3CCNCC3)n2n1]

The HCl salt of the title compound was prepared as described in Example 83 step 8. $^1$H NMR (300 MHz, DMSO-d$_6$) δ: 8.40 (s, 1H), 7.94 (dd, J=3.6, 1.2 Hz, 1H), 7.61 (dd, J=5.1, 1.2 Hz, 1H), 7.18 (dd, J=5.1, 3.6 Hz, 1H), 4.25 (t, J=5.0 Hz, 4H), 3.27 (br, 4H), 2.55 (s, 3H). MS m/z: 301 (M+H$^+$).

Example 85

2-Methyl-5-(4-methylpiperazin-1-yl)-8-(thiophen-3-yl)-[1,2,4]triazolo[1,5-c]pyrimidine

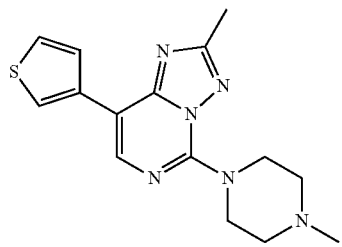 [SMILES: Cc1nc2c(-c3ccsc3)cnc(N3CCN(C)CC3)n2n1]

The HCl salt of the title compound was prepared as described in Example 83, except that thiophene-3-boronic acid was substituted for thiophene-2-boronic acid in step 7 of that route. $^1$H NMR (300 MHz, DMSO-d$_6$) δ: 8.49 (s, 1H), 8.42 (dd, J=3.3, 0.9 Hz, 1H), 7.88 (dd, J=5.1, 0.9 Hz, 1H), 7.67 (dd, J=5.1, 3.3 Hz, 1H), 4.94 (d, J=13.8 Hz, 2H), 3.66-3.50 (m, 4H), 3.27-3.14 (m, 2H), 2.77 (d, J=4.5 Hz, 3H), 2.55 (s, 3H). MS m/z: 315 (M+H$^+$).

Example 86

2-Methyl-5-(piperazin-1-yl)-8-(thiophen-3-yl)-[1,2,4]triazolo[1,5-c]pyrimidine

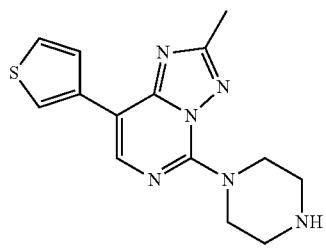 [SMILES: Cc1nc2c(-c3ccsc3)cnc(N3CCNCC3)n2n1]

The HCl salt of the title compound was prepared as described in Example 85 step 8. ¹H NMR (300 MHz, DMSO-d₆) δ: 8.49 (s, 1H), 8.42 (dd, J=3.3, 1.2 Hz, 1H), 7.88 (dd, J=5.1, 1.2 Hz, 1H), 7.68 (dd, J=5.1, 3.3 Hz, 1H), 4.21 (t, J=5.0 Hz, 4H), 3.28 (br, 4H), 2.54 (s, 3H). MS m/z: 301 (M+H⁺).

Example 87

5-(4-Methylpiperazin-1-yl)-8-(thiophen-2-yl)tetrazolo[1,5-c]pyrimidine

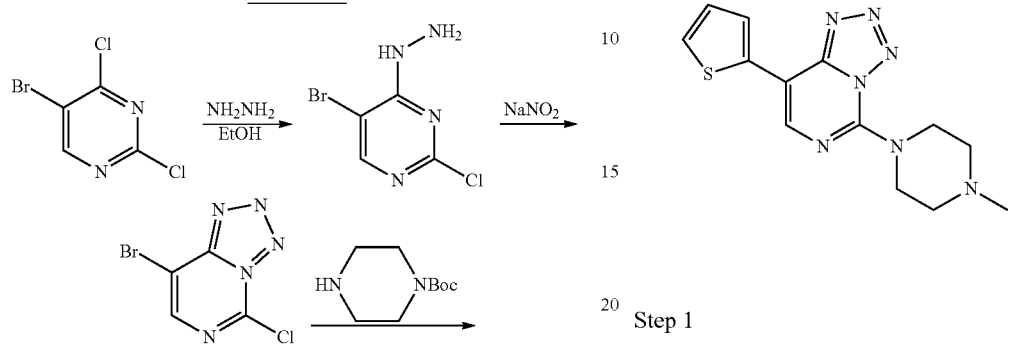

SCHEME 18

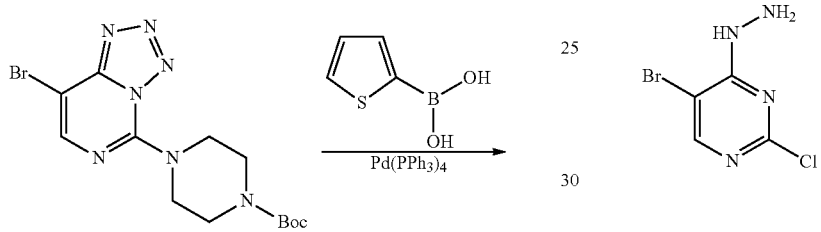

Step 1

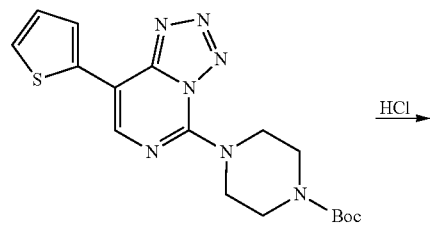

5-Bromo-2-chloro-4-hydrazinylpyrimidine

A 500 mL round bottom flask was charged with 5-bromo-2,4-dichloropyrimidine (13.5 g, 59.2 mmol), hydrazine hydrate (8.8 mL, 181 mmol) and absolute ethanol (300 mL). The resulting solution was refluxed under N₂ for 12 h. Work-up: the resulting crystalline solid was collected by filtration. The solid was washed with ethanol (100 mL), and dried to afford 17 g (quantitative) of the product as a yellow solid, which was used in the next step without further purification.

Step 2

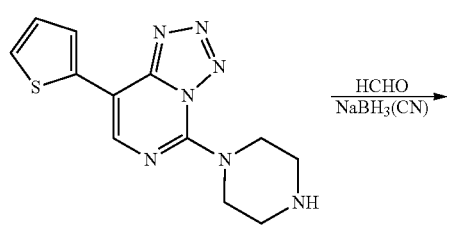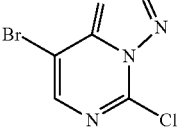

8-Bromo-5-chlorotetrazolo[1,5-c]pyrimidine

A 250 mL round bottom flask was charged with 5-bromo-2-chloro-4-hydrazinylpyrimidine (17 g, crude, 59.2 mmol) and 3 M HCl (600 mL). To the above was added dropwise a solution of NaNO₂ (8 g, 0.1 mol) in water (15 mL) at 10° C. The resulting mixture was stirred at 10° C. for 1 h. Work-up: the resulting crystalline solid was collected by filtration. The solid was washed with ethanol (20 mL), and dried to afford 10 g (72%) of the product as a red solid.

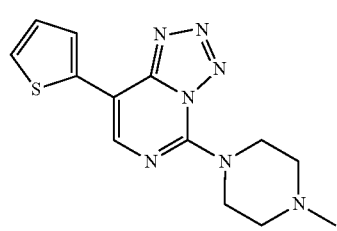 [SMILES: CN1CCN(c2ncc(-c3cccs3)c3nnnn23)CC1]

Step 3

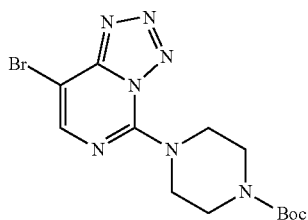 [SMILES: CC(C)(C)OC(=O)N1CCN(c2ncc(Br)c3nnnn23)CC1]

tert-Butyl 4-(8-bromotetrazolo[1,5-c]pyrimidin-5-yl)piperazine-1-carboxylate

A 250 mL round bottom flask was charged with 8-bromo-5-chlorotetrazolo[1,5-c]pyrimidine (10 g, 42.7 mmol), tert-butyl piperazine-1-carboxylate (11.9 g, 64 mmol), triethylamine (13 g, 0.13 mol) and ethanol (200 mL). The resulting mixture was heated at 30° C. for 2 h under $N_2$ and then cooled to room temperature. The mixture was concentrated under reduced pressure to dryness. The residue was diluted with water (20 mL) and extracted with dichloromethane (20 mL×3). The combined organic layers were washed with brine (20 mL), dried over anhydrous $Na_2SO_4$ and concentrated in vacuo, to afford 15.4 g (94%) of the product as an off-white solid.

Step 4

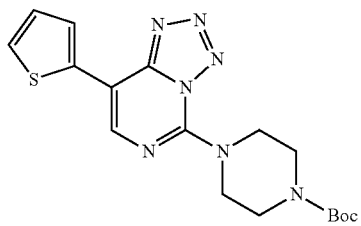 [SMILES: CC(C)(C)OC(=O)N1CCN(c2ncc(-c3cccs3)c3nnnn23)CC1]

tert-Butyl 4-(8-(thiophen-2-yl)tetrazolo[1,5-c]pyrimidin-5-yl)piperazine-1-carboxylate A 500 mL round bottom flask was charged with tert-butyl 4-(8-bromotetrazolo[1,5-c]pyrimidin-5-yl)piperazine-1-carboxylate (5.5 g, 14.3 mmol), thiophene-2-boronic acid (2.5 g, 21.5 mmol), tetrakis(triphenylphosphine)palladium(0) (2.0 g, 1.43 mmol), potassium tert-butoxide (2.4 g, 21.5 mmol), 1,4-dioxane (200 mL) and water (50 mL). After the air was purged by bubbling $N_2$ into the solution, the resulting mixture was stirred at 80° C. under $N_2$ for 10 h. Work-up: the reaction mixture was diluted with 0.1 M HCl (20 mL) and washed with EtOAc (150 mL×3). The aqueous layer was then basified with solid $NaHCO_3$ and extracted with $CH_2Cl_2$ (150 mL×3). The combined $CH_2Cl_2$ layers were dried over anhydrous $Na_2SO_4$ and concentrated in vacuo. The residue was purified by flash column chromatography on silica gel with 1-10% MeOH in $CH_2Cl_2$ to afford 0.70 g (12%) of the product, and 0.45 g (8.7%) of tert-Butyl 4-(4-amino-5-(thiophen-2-yl)pyrimidin-2-yl)piperazine-1-carboxylate.

Step 5

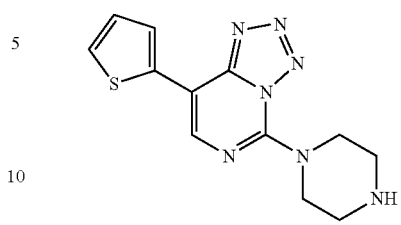

5-(piperazin-1-yl)-8-(thiophen-2-yl)tetrazolo[1,5-c]pyrimidine

A 50 mL round bottom flask was charged with tert-butyl 4-(8-(thiophen-2-yl)tetrazolo[1,5-c]pyrimidin-5-yl)piperazine-1-carboxylate (0.70 g, 1.8 mmol) and 3.3 M methanolic HCl (5 mL). The suspension was stirred at 25° C. for 4 h under $N_2$. Reaction progress was monitored by TLC (MeOH/$CH_2Cl_2$=1:20). Work-up: the resulting crystalline solid was collected by filtration. The solid was washed with ethyl ether (10 mL×3), and dried to afford 47 mg (8%) of the HCl salt of the product as a white solid. $^1H$ NMR (300 MHz, $CD_3OD$) δ: 8.54 (s, 1H), 7.42 (dd, J=5.1, 1.2 Hz, 1H), 7.39 (dd, J=3.6, 1.2 Hz, 1H), 7.08 (dd, J=5.1, 3.6 Hz, 1H), 4.12 (t, J=5.4 Hz, 4H), 3.33 (m, 4H). MS m/z: 288 (M+H$^+$).

Step 6

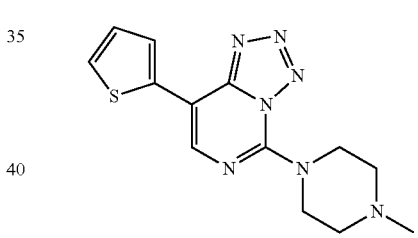

5-(4-Methylpiperazin-1-yl)-8-(thiophen-2-yl)tetrazolo[1,5-c]pyrimidine

A 100 mL round bottom flask was charged with 5-(piperazin-1-yl)-8-(thiophen-2-yl)tetrazolo[1,5-c]pyrimidine hydrochloride (0.16 g, 0.49 mmol), $CH_2Cl_2$ (20 mL), methanol (10 mL), 40% aqueous formaldehyde (2 mL) and $NaBH_3(CN)$ (0.1 g, 1.7 mmol). The resulting solution was stirred at room temperature for 0.5 h. Work-up: the reaction mixture was diluted with saturated aqueous $NaHCO_3$ and extracted with $CH_2Cl_2$ (50 mL×3). The combined organic layers were dried over anhydrous $Na_2SO_4$ and concentrated in vacuo. The residue was purified by flash column chromatography on silica gel with 1-10% MeOH in $CH_2Cl_2$ to afford 24 mg (16%) of the product as a white solid. $^1H$ NMR (300 MHz, $CD_3OD$) δ: 8.55 (s, 1H), 7.42 (dd, J=5.1, 1.2 Hz, 1H), 7.39 (dd, J=3.6, 1.2 Hz, 1H), 7.08 (dd, J=5.1, 3.6 Hz, 1H), 3.70-3.40 (br, 4H), 3.30-3.10 (br, 4H), 2.96 (s, 3H). MS m/z: 302 (M+H$^+$).

Example 88

5-(piperazin-1-yl)-8-(thiophen-2-yl)tetrazolo[1,5-c]pyrimidine

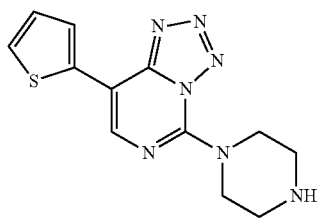 [SMILES: c1csc(-c2cnc(N3CCNCC3)n3nnnc23)c1]

The HCl salt of the title compound was prepared as described in Example 87 step 5. ¹H NMR (300 MHz, CD₃OD) δ: 8.54 (s, 1H), 7.42 (dd, J=5.1, 1.2 Hz, 1H), 7.39 (dd, J=3.6, 1.2 Hz, 1H), 7.08 (dd, J=5.1, 3.6 Hz, 1H), 4.12 (t, J=5.4 Hz, 4H), 3.33 (m, 4H). MS m/z: 288 (M+H+).

Example 89

5-(4-Methylpiperazin-1-yl)-8-(thiophen-3-yl)tetrazolo[1,5-c]pyrimidine

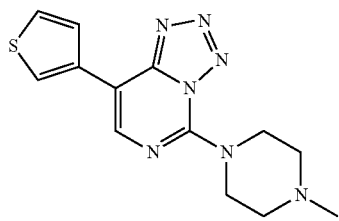 [SMILES: CN1CCN(c2ncc(-c3ccsc3)c3nnnn23)CC1]

The HCl salt of the title compound was prepared as described in Example 87, except that thiophene-3-boronic acid was substituted for thiophene-2-boronic acid in step 4 of that route. ¹H NMR (300 MHz, CD₃OD) δ: 8.49 (s, 1H), 7.72 (dd, J=3.0, 1.2 Hz, 1H), 7.50 (dd, J=5.1, 3.0 Hz, 1H), 7.41 (dd, J=5.1, 1.2 Hz, 1H), 4.85-4.83 (m, 2H), 3.66 (d, J=12.6 Hz, 2H), 3.55-3.45 (m, 2H), 3.30-3.15 (m, 2H), 2.98 (s, 3H). MS m/z: 302 (M+H+).

Example 90

5-(piperazin-1-yl)-8-(thiophen-3-yl)tetrazolo[1,5-c]pyrimidine

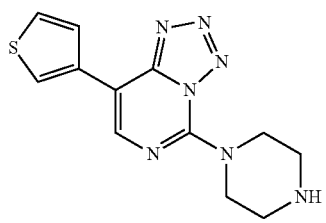 [SMILES: c1cc(-c2cnc(N3CCNCC3)n3nnnc23)cs1]

The HCl salt of the title compound was prepared as described in Example 89 step 5. ¹H NMR (300 MHz, CD₃OD) δ: 8.47 (s, 1H), 7.76 (dd, J=3.0, 1.5 Hz, 1H), 7.51 (dd, J=5.1, 3.0 Hz, 1H), 7.42 (dd, J=5.1, 1.5 Hz, 1H), 4.16 (t, J=5.4 Hz, 4H), 3.41 (t, J=5.4 Hz, 4H). MS m/z: 288 (M+H+).

The following compounds can generally be made using the methods known in the art and/or as shown above. It is expected that these compounds when made will have activity similar to those that have been made in the examples above.

The following compounds are represented herein using the Simplified Molecular Input Line Entry System, or SMILES. SMILES is a modern chemical notation system, developed by David Weininger and Daylight Chemical Information Systems, Inc., that is built into all major commercial chemical structure drawing software packages. Software is not needed to interpret SMILES text strings, and an explanation of how to translate SMILES into structures can be found in Weininger, D., *J. Chem. Inf. Comput. Sci.* 1988, 28, 31-36. All SMILES strings used herein, as well as numerous IUPAC names, were generated using CambridgeSoft's ChemDraw ChemBioDraw Ultra 11.0.

CN1CCN(CC1)C3=NC=C(C=2C=CSC=2)N4C=NN=C34
CN1CCN(CC1)C3=NC=C(C2=CC=C(C=C2)Br)N4C=NN=C34
CN1CCN(CC1)C3=NC=C(C2=CC=CC(=C2)Br)N4C=NN=C34
CN1CCN(CC1)C3=NC=C(C2=CC=C(C=C2)C(F)(F)F)N4C=NN=C34
CN1CCN(CC1)C3=NC=C(C2=CC=C(Br)S2)N4C=NN=C34
CN1CCN(CC1)C3=NC=C(C=2C=C(Br)SC=2)N4C=NN=C34
CN1CCN(CC1)C3=NC=C(C2=CC=C(C(F)(F)F)S2)N4C=NN=C34
CN1CCN(CC1)C3=NC=C(C=2C=C(C(F)(F)F)SC=2)N4C=NN=C34
CC4=CC=C(C1=CN=C(C2=NN=CN12)N3CCN(C)CC3)S4
CC1=CC(=CS1)C2=CN=C(C3=NN=CN23)N4CCN(C)CC4
CC1=CC=C(C=C1)C2=CN=C(C3=NN=CN23)N4CCN(C)CC4
CC=1C=CC=C(C=1)C2=CN=C(C3=NN=CN23)N4CCN(C)CC4
CN1CCN(CC1)C3=NC=C(C2=CC(=CS2)C1)N4C=NN=C34
CN1CCN(CC1)C3=NC=C(C2=CC(=CS2)Br)N4C=NN=C34
CN1CCN(CC1)C3=NC=C(C2=CC(=CS2)C(F)(F)F)N4C=NN=C34
CC=4C=C(C1=CN=C(C2=NN=CN12)N3CCN(C)CC3)SC=4
C1CN(CCN1)C3=NC=C(C=2C=CSC=2)N4C=NN=C34
C1CN(CCN1)C3=NC=C(C2=CC=C(C=C2)Br)N4C=NN=C34
C=1C=C(C=C(C=1)Br)C2=CN=C(C3=NN=CN23)N4CCNCC4
FC(F)(F)C1=CC=C(C=C1)C2=CN=C(C3=NN=CN23)N4CCNCC4
C1CN(CCN1)C3=NC=C(C2=CC=C(Br)S2)N4C=NN=C34
C1CN(CCN1)C3=NC=C(C=2C=C(Br)SC=2)N4C=NN=C34
FC(F)(F)C4=CC=C(C1=CN=C(C2=NN=CN12)N3CCNCC3)S4
FC(F)(F)C1=CC(=CS1)C2=CN=C(C3=NN=CN23)N4CCNCC4

CC4=CC=C(C1=CN=C(C2=NN=CN12)N3CCNCC3)S4
CC1=CC(=CS1)C2=CN=C(C3=NN=CN23)N4CCNCC4
CC1=CC=C(C=C1)C2=CN=C(C3=NN=CN23)N4CCNCC4
CC=1C=CC=C(C=1)C2=CN=C(C3=NN=CN23)N4CCNCC4
C1CN(CCN1)C3=NC=C(C2=CC(=CS2)C1)N4C=NN=C34
C1CN(CCN1)C3=NC=C(C2=CC(=CS2)Br)N4C=NN=C34
FC(F)(F)C=4C=C(C1=CN=C(C2=NN=CN12)N3CCNCC3)SC=4
CC=4C=C(C1=CN=C(C2=NN=CN12)N3CCNCC3)SC=4

The activity of the compounds in Examples 1-90 as H$_4$R inhibitors is illustrated in the following assay. The other compounds listed above, which have not yet been made and/or tested, are predicted to have activity in these assays as well.

BIOLOGICAL ACTIVITY ASSAY

In vitro Histamine Receptor Cell-Based Assays

The cell-based assays utilize an aequorin dependent bioluminescence signal. Doubly-transfected, stable CHO-K1 cell lines expressing human H$_4$, or H$_1$, mitochondrion-targeted aequorin, and (H$_4$ only) human G protein Gα16 are obtained from Perkin-Elmer. Cells are maintained in F12 (Ham's) growth medium, containing 10% (vol./vol.) fetal bovine serum, penicillin (100 IU/mL), streptomycin (0.1 mg/mL), zeocin (0.25 mg/mL) and geneticin (0.40 mg/mL). Cell media components are from Invitrogen, Inc. One day prior to assay, the growth medium is replaced with the same, excluding zeocin and geneticin. In some assays, cells previously frozen at "ready to use density" are thawed and immediately available for loading with coelenterazine-h dye as described below.

For assay preparation, growth medium is aspirated, and cells are rinsed with calcium-free, magnesium-free phosphate-buffered saline, followed by two to three minute incubation in Versene (Invitrogen, Inc.) at 37° C. Assay medium (DMEM:F12 [50:50], phenol-red free, containing 1 mg/mL protease-free bovine serum albumin) is added to collect the released cells, which are then centrifuged. The cell pellet is re-suspended in assay medium, centrifuged once more, and re-suspended in assay medium to a final density of 5×10$^6$ cells/mL. Coelenterazine-h dye (500 μM in ethanol) is added to a final concentration of 5 μM, and mixed immediately. The conical tube containing the cells is then wrapped with foil to protect the light-sensitive dye. The cells are incubated for four hours further at room temperature (approximately 21° C.) with end-over-end rotation to keep them in suspension.

Just before assay, the dye-loaded cells are diluted to 1.5×10$^6$ cells/mL (H$_4$ receptor) or 0.75×10$^6$ cells/mL (H$_1$ receptor) with additional assay medium. Cells are dispensed to 1536 well micro-titer plates at 3 μL/well. To assay receptor antagonism 60 nl of 100× concentration test compounds in 100% dimethyl sulfoxide (DMSO) are dispensed to the wells, one compound per well in concentration response array by passive pin transfer, and the plates are incubated for 15 minutes at room temperature. Assay plates are then transferred to a Lumilux bioluminescence plate reader (Perkin-Elmer) equipped with an automated 1536 disposable tip pipette. The pipette dispenses 3 μL/well of agonist (histamine, at twice the final concentration, where final concentration is a previously determined EC$_{80}$) in assay medium, with concurrent bioluminescence detection. Potential agonist activity of test compounds is measured by separate assays that measure response to test compounds alone, without added histamine agonist. CCD image capture on the Lumilux includes a 5 second baseline read and generally a 40 second read per plate after agonist (or test compound only in agonist mode assay) addition. A decrease in bioluminescence signal (measured either as area-under-the-curve, or maximum signal amplitude minus minimum signal amplitude) correlates with receptor antagonism in a dose dependent manner. The negative control is DMSO lacking any test compound. For antagonist assays, the positive controls are JNJ7777120 (1-[(5-Chloro-1H-indol-2-yl)carbonyl]-4-methyl-piperazine, 10 μM final concentration, H$_4$ receptor) and diphenhydramine (2-Diphenylmethoxy-N,N-dimethylethylamine, 10 μM final concentration, H$_1$ receptor). For agonist assays, the positive control is histamine (10 μM final concentration). Efficacy is measured as a percentage of positive control activity.

Examples were tested in at least an antagonist assay with an H$_4$ positive control. Selected compounds were also tested in an agonist assay. In the antagonist assay, certain compounds had an EC$_{50}$ of ≤10 μM, and others had an EC$_{50}$ of >10 μM. In the agonist assay, certain compounds had an EC$_{50}$<10 μM, others had an EC$_{50}$>10 μM but <100 μM, others had no activity to 10 μM, and others had no activity to 100 μM. In certain embodiments, desirable compounds are selective H$_4$ antagonists.

Other compounds disclosed herein may be similarly tested as well by one of skill in the art, and it is expected that many of these compounds when tested will be active and will have utility.

IN VIVO ASSAY

Assessment of H$_4$ Antagonism—Model of Allergic Rhinits in Balb/C mice.
Animals Female BALB/c mice, 6-12 weeks of age, were obtained from Jackson Laboratories (Bar Harbor, Me.). All experimental animals used in this work were under a protocol approved by the Institutional Animal Care and Use Committee of the National Jewish Medical and Research Center, Denver, Colo.

Induction and Measurement of Allergic Rhinitis

The assay protocol is similar to that described in Miyahara, S. et al. (2005), *J Allergy Clin Immunol.*, 116:1020-1027. The role of the H4 receptor in this model has been validated [Shiraishi, Y. et al. (2009), *J Allergy Clin Immunol.*, 123:S56]. Briefly, mice received intraperitoneal injections of 20 μg ovalbumin (OVA, Grade V; Sigma-Aldrich, St. Louis, Mo.), previously emulsified in 2.25 mg of alum (AlumImuject; Pierce, Rockford, Ill.) in a total volume of 100 μL (sensitization phase). Injections occurred on days 0 and 14. Starting on day 28 onward (challenge phase), mice received daily intranasal instillation of OVA (25 mg/ml in phosphate-buffered saline), 15 μl in each nostril without anesthesia. Installations occurred for 6 days to evoke allergic nasal inflammation and congestion. Compounds were tested for the ability to prevent induction of nasal inflammation and congestion by intranasal instillation 2.5 hours prior to OVA instillation. Instillations of compounds were performed using 10 (0.1% weight/volume [1 mg/ml]) in each nostril without anesthesia, in formulation vehicle: either (a) unbuffered saline, [pH approximately 6.0], 0.2% volume/volume Tween-80 (Sigma-Aldrich, St. Louis, Mo.), or (b) 50 mM sodium acetate [pH 5.0], 100 mM sodium chloride, 0.2% volume/volume Tween-80. On day 4 (early phase) and day 7 (late phase) after starting OVA challenges, respiratory frequency (RF) was measured in conscious animals by single chamber restrained whole-body plethysmography (WBP) [Buxco Research Systems, Troy, New York].

Because mice are obligate nasal breathers, OVA induced nasal inflammation and congestion results in decreased breathing frequency. Compounds that block OVA-induced nasal inflammation and congestion prevent the decrease in RF compared to positive control (instillation with formulation vehicle only prior to OVA challenge). The assay negative control measures baseline RF, where challenge is performed with phosphate-buffered saline lacking OVA. After whole-body plethysmography on day 7, nasal airflow impedance was measured as described ($R_{NA}$, see Methods section for Miyahara S. et al. [above] in the online supplemental material at the Journal of Allergy and Clinical Immunology: www.jacionline.org), using a custom-designed ventilator (Flexivent; Scireq, Montreal, Quebec, Canada). After airflow impedance measurement, the study was terminated and animals were euthanized.

Certain compounds have been tested at a concentration of 0.1% w/v in the above assay and have been found to have activity that is statistically significant compared to positive control. Certain other compounds tested at this concentration were either weakly active, or inactive (i.e., statistically indistinguishable from positive control). Other compounds disclosed herein may be similarly tested as well by one of skill in the art, and it is expected that many of these compounds when tested will be active and will have utility.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A compound of structural Formula (IX)

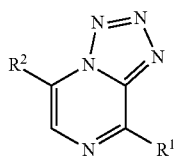

(IX)

or a pharmaceutically acceptable salt thereof, wherein:
$R^1$ is a monocyclic 4- to 7-membered nonaromatic heterocycloalkyl, which may be optionally substituted with a substituent chosen from amino and lower alkyl; and
$R^2$ is chosen from monocyclic 5- to 7-membered nonaromatic heterocycloalkyl, phenyl and monocyclic 5- to 6-membered heteroaryl, any of which may be optionally substituted with one to three substituents chosen from halogen, lower alkyl, lower haloalkyl, lower alkoxy, lower haloalkoxy, cyano, lower amino, hydroxy, and nitro.

2. The compound as recited in claim 1, having structural Formula (X)

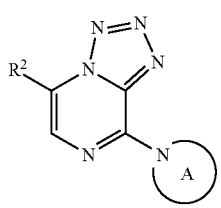

(X)

or a pharmaceutically acceptable salt thereof, wherein:
A is a monocylic 4- to 7-membered nonaromatic heterocycloalkyl which is attached through a ring nitrogen to the ocore and which may be optionally substituted with a substituent chosen from amino and lower alkyl; and
$R^2$ is chosen from phenyl, furan, thiophene, pyrrole, pyrroline, pyrrolidine, oxazole, thiazole, imidazole, pyrazole, imidazoline, imidazolidine, pyrazoline, pyrazolidine, isoxazole, isothiazole, oxadiazole, thiadiazole, triazole, pyran, pyridine, piperidine, morpholine, thiomorpholine, piperazine, pyridazine, pyrimidine, and pyrazine, any of which may be optionally substituted with one to three substituents chosen from halogen, lower alkyl, lower haloalkyl, lower alkoxy, lower haloalkoxy, cyano, lower amino, hydroxy, and nitro.

3. The compound as recited in claim 2, having structural Formula (XI)

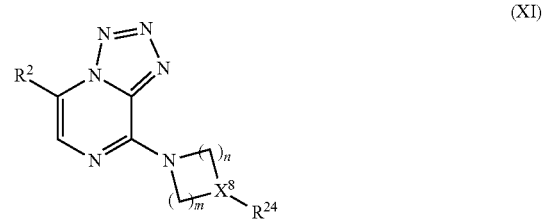

(XI)

or a pharmaceutically acceptable salt thereof, wherein:
$X^8$ is chosen from CH and N;
m and n are each an integer chosen from 1 and 2;
$R^2$ is chosen from phenyl, furan, thiophene, and thiazole, any of which may be optionally substituted with one to three substituents chosen from halogen, lower alkyl, lower haloalkyl, lower alkoxy, lower haloalkoxy, cyano, lower amino, hydroxy, and nitro; and
$R^{24}$ is chosen from hydrogen, amino, and lower alkyl.

4. The compound as recited in claim 3, or a pharmaceutically acceptable salt thereof, wherein $R^2$ is thiophene, optionally substituted with one to three substituents chosen from halogen, lower alkyl, lower haloalkyl, lower alkoxy, lower haloalkoxy, cyano, lower amino, hydroxy, and nitro.

5. The compound as recited in claim 3, or a pharmaceutically acceptable salt thereof, wherein $R^2$ is thiophene, optionally substituted with one to three halogen substituents.

6. The compound as recited in claim 3, or a pharmaceutically acceptable salt thereof, wherein $R^2$ is thiophene.

7. The compound as recited in claim 3, or a pharmaceutically acceptable salt thereof, wherein:
$X^8$ is CH;
m and n are each 1; and
$R^{24}$ is chosen from hydrogen, amino, and lower alkyl.

8. The compound as recited in claim 7, or a pharmaceutically acceptable salt thereof, wherein $R^{24}$ is amino.

9. The compound as recited in claim 8, or a pharmaceutically acceptable salt thereof, wherein $R^{24}$ is $NHCH_3$.

10. The compound as recited in claim 3, or a pharmaceutically acceptable salt thereof, wherein:
$X^8$ is N;
m and n are each 2; and
$R^{24}$ is chosen from hydrogen and lower alkyl.

11. The compound as recited in claim 10, or a pharmaceutically acceptable salt thereof, wherein $R^{24}$ is chosen from hydrogen and methyl.

12. The compound as recited in claim 11, or a pharmaceutically acceptable salt thereof, wherein $R^{24}$ is methyl.

13. A compound as recited in claim 1, chosen from:

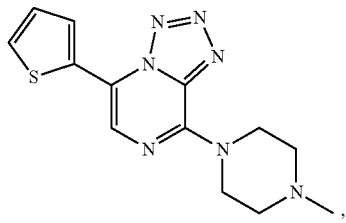

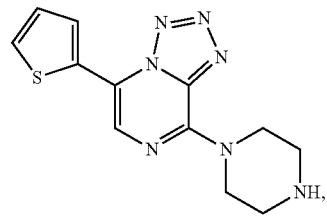

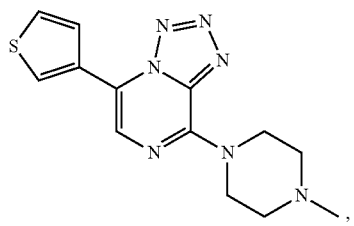

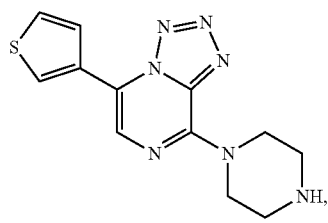

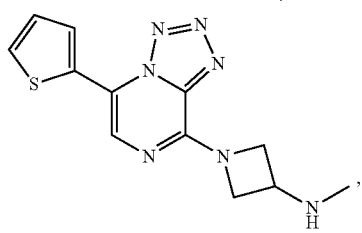

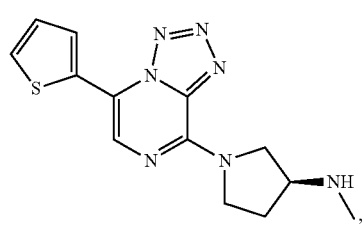

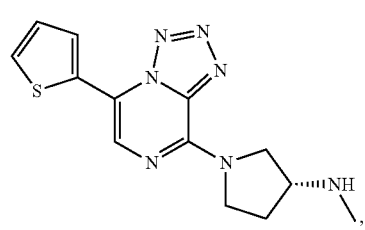

-continued

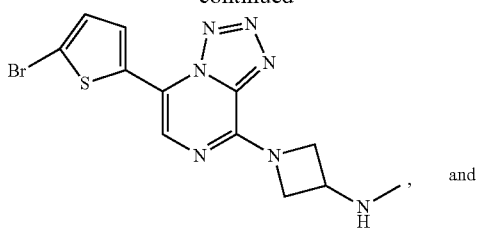

and

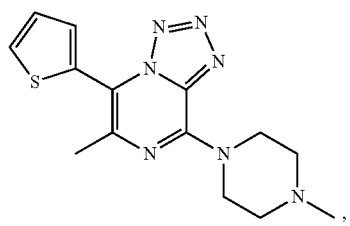

or a pharmaceutically acceptable salt thereof.

14. A pharmaceutical composition comprising a compound as recited in claim 1, or a pharmaceutically acceptable salt thereof, together with a pharmaceutically acceptable carrier.

15. A pharmaceutical composition as recited in claim 14, wherein the compound is chosen from:

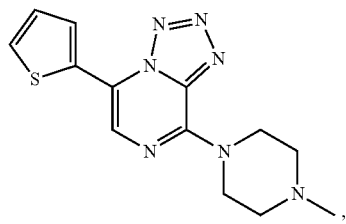

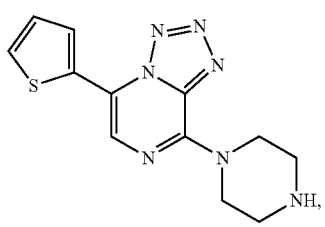

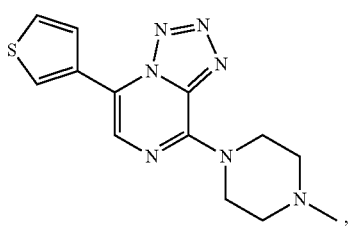

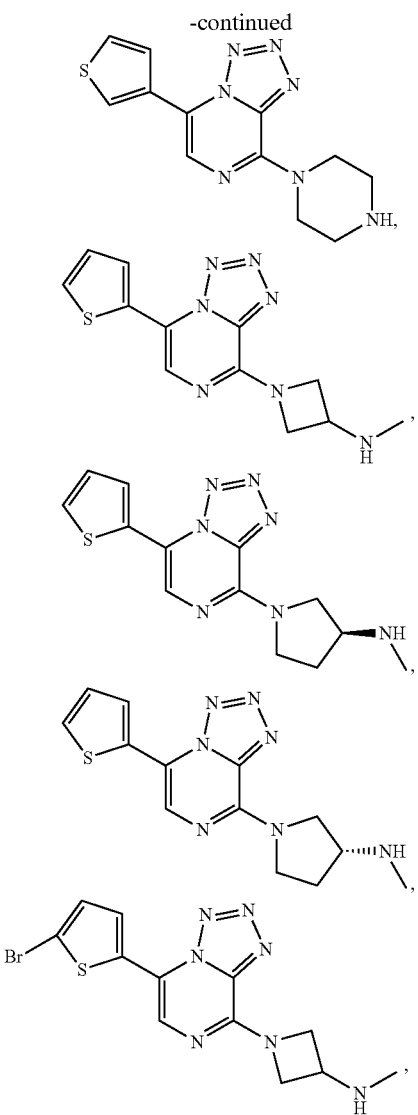
and
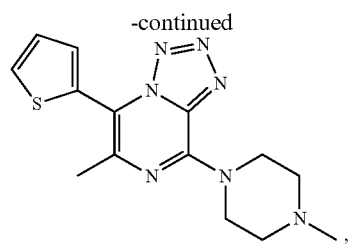
or a pharmaceutically acceptable salt thereof, together with a pharmaceutically acceptable carrier.
16. The compound
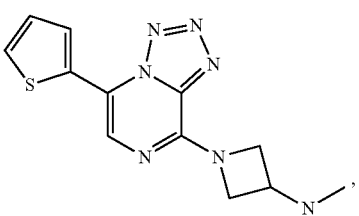
or a pharmaceutically acceptable salt thereof.
17. A pharmaceutical composition comprising
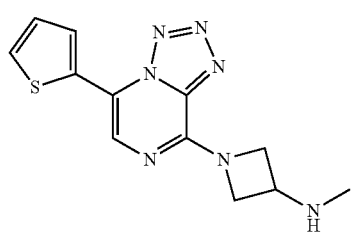 [SMILES: CNC1CN(c2ncc(-c3cccs3)n3nnnc23)C1]
or a pharmaceutically acceptable salt thereof, together with a pharmaceutically acceptable carrier.
* * * * *